(12) United States Patent
Gerlach et al.

(10) Patent No.: US 7,671,074 B2
(45) Date of Patent: Mar. 2, 2010

(54) SULFONYLGUANIDINE COMPOUNDS AND PHARMACEUTICAL USES THEREOF

(75) Inventors: Matthias Gerlach, Brachttal (DE); Heinz Uragg, Stolberg (DE); Michael Haurand, Aachen (DE); Claudia Katharina Puetz, Dueren (DE); Corinna Sundermann, Aachen (DE); Boris Chizh, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/742,946

(22) Filed: May 1, 2007

(65) Prior Publication Data

US 2008/0085900 A1  Apr. 10, 2008

Related U.S. Application Data

(60) Division of application No. 10/402,382, filed on Mar. 31, 2003, now abandoned, which is a continuation of application No. PCT/EP01/11245, filed on Oct. 1, 2001.

(30) Foreign Application Priority Data

Sep. 30, 2000 (DE) ................. 100 48 716
Mar. 12, 2001 (DE) ................. 101 12 068

(51) Int. Cl.
*A61K 31/44* (2006.01)
(52) U.S. Cl. ................................. 514/357
(58) Field of Classification Search ........... 514/357
See application file for complete search history.

(56) References Cited

U.S. PATENT DOCUMENTS

| 4,900,740 A | 2/1990 | Muller et al. |
| 4,904,299 A * | 2/1990 | Shapiro ............... 504/221 |
| 6,100,428 A | 8/2000 | Bhat et al. |
| 6,518,423 B1 * | 2/2003 | Kaneko et al. ........... 544/34 |

FOREIGN PATENT DOCUMENTS

| DE | 1 518 852 A | 6/1969 |
| EP | 0195673 | 9/1986 |
| GB | 565566 | 11/1944 |
| JP | 45 017 680 | 6/1970 |
| JP | 6-9541 | 1/1994 |
| WO | WO 92/14456 * | 9/1992 |
| WO | WO 98/34113 | 8/1998 |
| WO | WO 99/20599 | 4/1999 |
| WO | WO 00/15611 | 3/2000 |

OTHER PUBLICATIONS

Wolff, Manfred E. "Burger's Medicinal Chemistry, 5ed, Part I", John Wiley & Sons, 1995, pp. 975-977.*

(Continued)

*Primary Examiner*—San-ming Hui
(74) *Attorney, Agent, or Firm*—Crowell & Moring LLP

(57) ABSTRACT

Sulfonylguanidine compounds corresponding to the tautomeric formulas I and Ia, a method for producing them, pharmaceutical compositions containing them, and methods of using them to prepare medicaments and for treating various medical conditions. The sulfonylguanidine compounds have an affinity for the gabapentin binding site and can be used to treat conditions such as pain, epilepsy, migraine and others.

18 Claims, 40 Drawing Sheets

OTHER PUBLICATIONS

The Merck Manual of Diagnosis and Therapy (17th ED) (1999), p. 1358, 1376-1377.*
Janka et al. Theraple der Gegenwart (1974), 113(12), 2163-4, 2166-8, Abstract in English.*
The structure and registry No. 27031-08-9.*
Denk et al. Arzneimittel-Forschung (1973), 23(2), 187-91, German, English abstract.*
Carrara et al. Therapie (1959), 14, 864-6.*
Beers, M., The Merck Manual of Diagnosis and Therapy (17th ED) (1999), p. 168-169. 257-259.*
Janka et al, Effect of Sulfaguanol (Enterocura) on the Carbohydrate Metabolism of Diabetics and Individuals with Healthy Metabolism, 1974, Therapie der Gegenwart, 113, pp. 2163-2168 (English translation.).*
Denk et al, Pharmacokinetics of Sulfaguanol-Multiple Dose Kinetics of Oral Use in Humans, 1973, Arzneim.-Forsch. (Drug Res.), 23 (2), pp. 187-191 (English translation.).*
Carrara et al, Antidiabetic Sulfamide with Slow-Release Chemical Structure. I) Chemical Study, 1959, Therapie, XIV, pp. 864-866 (English translation.).*
Yu. A. Baskakov, et al., 6001 Chemical Abstracts, Columbus, Ohio, vol. 53, No. 8, Apr. 25, 1959, XP-002185314.
A. Barghon, et al., 6001 Chemical Abstracts, Columbus, Ohio, vol. 53, No. 8, Apr. 25, 1959, XP-002185315.
Database Crossfire Beilstein, Database accession Nos. BRN 2899488, 2951283 and 2903865, XP-002185322.
Database Crossfire Beilstein, Database accession Nos. BRN 4170152 and 867787, XP-002185324.
Kozakiewicz, Irena, 6001 Chemical Abstracts, Columbus, Ohio, vol. 119, No. 3, Jul. 19, 1993, XP-002185317.
Ian M. Eggleston, et al., 6001 Chemical Abstracts, Columbus, Ohio, vol. 115, No. 23, Dec. 9, 1991, XP-002185318.
E. Fisher, et al., 6001 Chemical Abstracts, Columbus, Ohio, vol. 101, No. 11, Sep. 10, 1984, XP-002185319.
Robert J. Galbreath, et al., 6001 Chemical Abstracts, Columbus, Ohio, vol. 53, No. 21, Nov. 10, 1959, XP-002185320.
Alfreda Dansi, et al., 6001 Chemical Abstracts, Columbus, Ohio, vol. 55, No. 5, Mar. 6, 1961, XP-002185321.
Kimura, et al., 6001 Chemical Abstracts, Columbus, Ohio, vol. 121, No. 15, Oct. 10, 1994, XP-002185316. Abstract of JP 6-9541.
Chemical Abstracts Service, Columbus, Ohio, Database accession No. 129:175973 XP002185323. Abstract of WO/9834113.
Khim.-Farm. Zh., 1971 5(3), S. 12-16.
German Communication dated May 8, 2001.
International Search Report dated Jan. 11, 2002.
Scott, F. L., "Nitrogen Systems. Part VI. Some Nucleophillic Displacements on 1-Ammonocarbonopyrazoles", Chemistry and Industry, 1956, 547-548; ISSN: 0009-3068.

* cited by examiner

SULFONYLGUANIDINE COMPOUNDS AND PHARMACEUTICAL USES THEREOF

CROSS REFERENCE TO RELATED APPLICATIONS

This application is a divisional of U.S. patent application Ser. No. 10/402,382, filed Mar. 31, 2003 which is a continuation of International patent application Serial No. PCT/EP01/11245, filed Oct. 1, 2001, designating the United States of America, and published in German as WO 02/30881, the entire disclosures of which are incorporated herein by reference. Priority is claimed based on Federal Republic of Germany patent application nos. DE 100 48 716.5 and DE 101 12 068.0, filed Sep. 30, 2000 and Mar. 12, 2001, respectively.

BACKGROUND OF THE INVENTION

The present invention relates to sulfonylguanidine compounds, processes for their production, pharmaceutical compositions containing these compounds, and the use of sulfonylguanidines for the production of medicaments and for treating pain and other medical conditions.

The cyclic GABA analogue gabapentin is a clinically proven antiepileptic. Gabapentin additionally exhibits further interesting, medically relevant properties, in particular as an analgesic. New classes of structures that have an affinity for the gabapentin binding site are therefore of interest. In connection with the aforementioned medical indications there is a further need of substances that are similar in their properties to gabapentin, for example as regards analgesic effect.

The treatment of chronic and non-chronic pain conditions is very important in medicine. There is a wide need for highly effective pain treatments. The urgent need for a patient-oriented and targeted treatment of chronic and non-chronic pain conditions, which is understood to be the successful and satisfactory treatment of pain on the part of the patient, is documented in the large number of scientific studies that have recently appeared in the field of applied analgesia and in basic research relating to nociception.

Conventional opioids such as morphine are highly effective in treating severe to extremely severe pain. Their use is however limited by the known side effects such as for example respiratory depression, vomiting, sedation, constipation and development of tolerance. Also, they are less effective in treating neuropathic or incidental pain afflicting in particular tumor patients.

SUMMARY OF THE INVENTION

An object of the invention was accordingly to provide new methods of treating pain and other medical conditions.

Another object of the invention was to provide new compounds that have an affinity for the gabapentin binding site and/or corresponding physiological activities, for example with regard to analgesia, but also other GBP indications.

The present invention accordingly provides for the use of a sulfonylguanidine according to the general tautomeric formulas I and Ia,

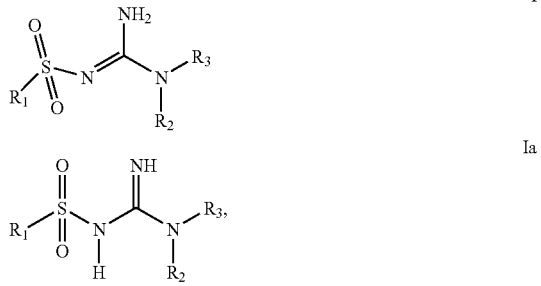

wherein $R^1$ is selected from $C_{1-10}$-alkyl that is branched or unbranched, saturated or unsaturated, singly or multiply substituted or unsubstituted; $C_{3-8}$-cycloalkyl or bicyclic alkylene, in each case saturated or unsaturated, singly or multiply substituted or unsubstituted; aryl or heteroaryl, in each case unsubstituted or singly or multiply substituted; or aryl, $C_{3-9}$-cycloalkyl or heteroaryl, bonded via saturated or unsaturated $C_{1-3}$-alkyl, in each case unsubstituted or singly or multiply substituted;

$R^2$ is selected from $C_{1-10}$-alkyl that is branched or unbranched, saturated or unsaturated, singly or multiply substituted or unsubstituted; $C_{3-8}$-cycloalkyl that is saturated or unsaturated, singly or multiply substituted or unsubstituted; aryl or heteroaryl, in each case unsubstituted or singly or multiply substituted; or aryl, $C_{3-9}$-cycloalkyl or heteroaryl, bonded via saturated or unsaturated $C_{1-3}$-alkyl, $S(O)_2$ or NH, in each case unsubstituted or singly or multiply substituted; or $NR^4R^5$, where $R^4$, $R^5$ independently of one another are selected from H; $C_{1-18}$-alkyl that is branched or unbranched, saturated or unsaturated, singly or multiply substituted or unsubstituted; $C_{3-8}$-cycloalkyl that is saturated or unsaturated, singly or multiply substituted or unsubstituted; aryl or heteroaryl, in each case unsubstituted or singly or multiply substituted; or aryl, $C_{3-9}$-cycloalkyl or heteroaryl, bonded via saturated or unsaturated $C_{1-3}$-alkyl, in each case unsubstituted or singly or multiply substituted; or $SO_2R^6$, where $R^6$ is selected from $C_{1-18}$-alkyl that is branched or unbranched, saturated or unsaturated, singly or multiply substituted or unsubstituted; $C_{3-8}$-cycloalkyl that is saturated or unsaturated, singly or multiply substituted or unsubstituted; aryl or heteroaryl, in each case unsubstituted or singly or multiply substituted; or aryl, $C_{3-9}$-cycloalkyl or heteroaryl, bonded via saturated or unsaturated $C_{1-3}$-alkyl, in each case unsubstituted or singly or multiply substituted;

or $R^4$ and $R^5$ together form: $-CH_2CH_2OCH_2CH_2-$; $-CH_2CH_2N(R^7)CH_2CH_2$, where $R^7$ is selected from $C_{1-18}$-alkyl that is branched or unbranched, saturated or unsaturated, singly or multiply substituted or unsubstituted; $C_{3-8}$-cycloalkyl that is saturated or unsaturated, singly or multiply substituted or unsubstituted; aryl or heteroaryl, in each case unsubstituted or singly or multiply substituted; or aryl, $C_{3-9}$-cycloalkyl or heteroaryl, bonded via saturated or unsaturated $C_{1-3}$-alkyl, in each case unsubstituted or singly or multiply substituted;

$R^3$ is selected from H, $C_{1-10}$-alkyl that is branched or unbranched, saturated or unsaturated, singly or multiply substituted or unsubstituted; $C_{3-8}$-cycloalkyl that is saturated or unsaturated, singly or multiply substituted or unsubstituted; aryl or heteroaryl, in each case unsubstituted or singly or multiply substituted; or aryl, $C_{3-9}$-cycloalkyl or heteroaryl, bonded via saturated or unsaturated $C_{1-3}$-alkyl, in each case unsubstituted or singly or multiply substituted;

or $R^2$ and $R^3$ together form

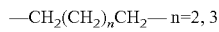
—CH$_2$(CH$_2$)$_n$CH$_2$— n=2, 3

—CH$_2$CH$_2$OCH$_2$CH$_2$— or

—CH$_2$CH$_2$N(R$^8$)CH$_2$CH$_2$— where $R^8$ is selected from $C_{1-18}$-alkyl that is branched or unbranched, saturated or unsaturated, singly or multiply substituted or unsubstituted; $C_{3-8}$-cycloalkyl or bicyclic alkylene that is saturated or unsaturated, singly or multiply substituted or unsubstituted; aryl or heteroaryl, in each case unsubstituted or singly or multiply substituted; or aryl, $C_{3-9}$-cycloalkyl or heteroaryl, bonded via saturated or unsaturated $C_{1-3}$-alkyl, in each case unsubstituted or singly or multiply substituted;

optionally in the form of their racemates, their pure stereoisomers, in particular enantiomers or diastereomers, or in the form of mixtures of the stereoisomers, in particular of the enantiomers or diastereomers, in an arbitrary mixture ratio; in the represented form or in the form of their acids or bases or in the form of their salts, in particular of the physiologically compatible salts, or in the form of their solvates, in particular the hydrates; in both tautomeric forms according to formulas I and Ia, exclusively in one of the tautomeric forms according to formulas I or Ia or also in mixtures of both forms according to formulas I and Ia, in which the preferred tautomeric form may vary from compound to compound depending on the state of aggregation or on the chosen solvent;

for the production of a medicament and for treating pain, neuropathic, chronic or acute pain, epilepsy and/or migraine, or for the production of a medicament and for the treatment of hyperalgesia and allodynia, in particular thermal hyperalgesia, mechanical hyperalgesia and allodynia and cold-induced allodynia, or inflammatory or post-operative pain, or for the production of a medicament and for the treatment of hot flashes, post-menopausal symptoms, amyotropic lateral sclerosis (ALS), reflex sympathetic dystrophy (RSD), spastic paralysis, restless leg syndrome, acquired nystagmus; psychiatric or neuropathological disorders such as bipolar disorders, anxiety, panic attacks, mood fluctuations, manic behavior, depression, manic-depressive behavior; painful diabetic neuropathy, symptoms and pain due to multiple sclerosis or Parkinson's disease, neurodegenerative diseases such as Alzheimer's disease, Huntington's disease, Parkinson's disease and epilepsy; gastrointestinal lesions; erythromelalgic or post-poliomyelitic pain, trigeminal or post-herpetic neuralgia; or as an anticonvulsant, analgesic or anxiolytic.

In one embodiment of the invention the following applies as regards the employed sulfonylguanidines according to the general tautomeric formulas I and Ia:

$R^1$ is selected from $C_{1-10}$-alkyl that is branched or unbranched, saturated or unsaturated, singly or multiply substituted or unsubstituted; $C_{3-8}$-cycloalkyl or bicyclic alkylene, in each case saturated or unsaturated, singly or multiply substituted or unsubstituted; phenyl that is unsubstituted or singly or multiply substituted.

In a further embodiment of the invention the following applies as regards the employed sulfonylguanidines according to the general tautomeric formulas I and Ia:

$R^2$ is selected from $C_{1-10}$-alkyl that is branched or unbranched, saturated or unsaturated, singly or multiply substituted or unsubstituted; $C_{3-8}$-cycloalkyl that is saturated or unsaturated, singly or multiply substituted or unsubstituted; aryl or heteroaryl, in each case unsubstituted or singly or multiply substituted; or aryl, $C_{3-9}$-cycloalkyl or heteroaryl, bonded via saturated or unsaturated $C_{1-3}$-alkyl, in each case unsubstituted or singly or multiply substituted.

In another embodiment of the invention the following applies as regards the employed sulfonylguanidines according to the general tautomeric formulas I and Ia, $R^3$ is selected from H or CH$_3$.

In yet a further embodiment of the invention the following applies as regards the employed sulfonylguanidines according to the general tautomeric formulas I and Ia:

$R^2$ and $R^3$ together form

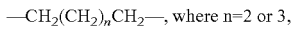
—CH$_2$(CH$_2$)$_n$CH$_2$—, where n=2 or 3,

—CH$_2$CH$_2$OCH$_2$CH$_2$—, or

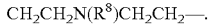
CH$_2$CH$_2$N(R$^8$)CH$_2$CH$_2$—.

In a particularly preferred embodiment of the invention the following applies as regards the employed sulfonylguanidines according to the general tautomeric formulas I and Ia:

$R^1$ is selected from $C_{3-8}$-cycloalkyl or bicyclic alkylene, in each case saturated or unsaturated, singly or multiply substituted or unsubstituted; aryl or heteroaryl, in each case unsubstituted or singly or multiply substituted; or aryl, $C_{3-8}$-cycloalkyl or heteroaryl, bonded via saturated or unsaturated $C_{1-4}$-alkyl, in each case unsubstituted or singly or multiply substituted;

$R^2$ is selected from $C_{1-10}$-alkyl that is branched or unbranched, saturated or unsaturated, singly or multiply substituted or unsubstituted; $C_{3-8}$-cycloalkyl that is saturated or unsaturated, singly or multiply substituted or unsubstituted; aryl or heteroaryl, in each case unsubstituted or singly or multiply substituted; or aryl, $C_{3-9}$-cycloalkyl or heteroaryl, bonded via saturated or unsaturated $C_{1-3}$-alkyl, in each case unsubstituted or singly or multiply substituted; and $R^3$ is selected from H, $C_{1-10}$-alkyl that is branched or unbranched, saturated or unsaturated, singly or multiply substituted or unsubstituted.

These substances bind to the gabapentin binding site and exhibit a pronounced analgesic action.

Within the context of the present invention, alkyl radicals and cycloalkyl radicals are understood to be saturated and unsaturated (but not aromatic), branched, unbranched and cyclic hydrocarbons that may be unsubstituted or singly or multiply substituted. In this connection $C_{1-2}$-alkyl denotes C1- or C2-alkyl, $C_{1-3}$-alkyl denotes C1-, C2- or C3-alkyl, $C_{1-4}$-alkyl denotes C1-, C2-, C3- or C4-alkyl, $C_{1-5}$-alkyl denotes C1-, C2-, C3-, C4 or C5-alkyl, $C_{1-6}$-alkyl denotes C1-, C2-, C3-, C4-, C5- or C6-alkyl, $C_{1-7}$-alkyl denotes C1-, C2-, C3-, C4-, C5-, C6- or C7-alkyl, $C_{1-8}$-alkyl denotes C1-, C2-, C3-, C4-, C5-, C6-, C7 or C8-alkyl, $C_{1-10}$-alkyl denotes C1-, C2-, C3-, C4-, C5-, C6-, C7-, C8-, C9- or C10-alkyl and $C_{1-18}$-alkyl denotes C1-, C2-, C3-, C4-, C5-, C6-, C7-, C8-, C9-, C10-, C11-, C12-, C13-, C14-, C15-, C16-, C17- or C18-alkyl. In addition $C_{3-4}$-cycloalkyl denotes C3- or C4-cycloalkyl, $C_{3-5}$-cycloalkyl denotes C3-, C4- or C5-cycloalkyl, $C_{3-6}$-cycloalkyl denotes C3-, C4-, C5- or C6-cycloalkyl, $C_{3-7}$-cycloalkyl denotes C3-, C4-, C5-, C6- or C7-cycloalkyl, $C_{3-8}$-cycloalkyl denotes C3-, C4-, C5-, C6-, C7- or C8-cycloalkyl, $C_{4-5}$-cycloalkyl denotes C4- or C5-cycloalkyl, $C_{4-6}$-cycloalkyl denotes C4-, C5- or C6-cycloalkyl, $C_{4-7}$-cycloalkyl denotes C4-, C5-, C6- or C7-cycloalkyl, $C_{5-6}$-cycloalkyl denotes C5- or C6-cycloalkyl and $C_{5-7}$-cycloalkyl denotes C5-, C6- or C7-cycloalkyl. With regard to cycloalkyl, the term also includes saturated cycloalkyls in which 1 or 2 carbon atoms are replaced by a heteroatom, i.e. S, N or O. The term cycloalkyl however also includes in particular singly or multiply, preferably singly, unsaturated cycloalkyls without a heteroatom in the ring as long as the cycloalkyl does not form an aromatic system. The alkyl or cycloalkyl radicals are preferably methyl, ethyl, vinyl (ethenyl), propyl, allyl(2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, but also adamantyl, $CHF_2$, $CF_3$ or $CH_2OH$ as well as pyrazolinone, oxopyrazolinone, [1,4]dioxane or dioxolane.

In connection with alkyl and cycloalkyl, the term "substituted" within the context of the present invention denotes—unless expressly defined otherwise—the substitution of at least one (optionally also several) hydrogen atom(s) by F, Cl, Br, I, $NH_2$, SH or OH, wherein the terms "multiply substituted" and "substituted" in the case of multiple substitution denote that the substitution takes place on different as well as on the same atoms multiply with the same or different substituents, for example triple substitution on the same C atom as in the case of $CF_3$, or at different positions as in the case of —CH(OH)—CH=CH—$CHCl_2$. Particularly preferred substituents in this connection are F, Cl and OH. With regard to cycloalkyl, the hydrogen atom may also be replaced by $OC_{1-3}$-alkyl or $C_{1-3}$-alkyl (in each case singly or multiply substituted or unsubstituted), in particular methyl, ethyl, n-propyl, i-propyl, $CF_3$, methoxy or ethoxy.

The term $(CH_2)_{3-6}$ is understood to denote —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, and the term $(CH_2)_{1-4}$ is understood to denote —$CH_2$—, —$CH_2$—$CH_2$—, —$CH_2$—$CH_2$—$CH_2$— and —$CH_2$—$CH_2$—$CH_2$—$CH_2$—, and the term $(CH_2)_{4-5}$ is understood to denote —$CH_2$—$CH_2$—$CH_2$—$CH_2$— and —$CH_2$—$CH_2$—$CH_2$—$CH_2$—$CH_2$—, etc.

The term "aryl radical" is understood to mean ring systems with at least one aromatic ring but without heteroatoms in even only one of the rings. Examples are phenyl, naphthyl, fluoranthenyl, fluorenyl, tetralinyl or indenyl, in particular 9H-fluorenyl or anthracenyl radicals, which may be unsubstituted or singly or multiply substituted.

The term heteroaryl radical is understood to mean heterocyclic ring systems with at least one unsaturated ring that may contain one or more heteroatoms from the group comprising nitrogen, oxygen and/or sulfur, and which may also be singly or multiply substituted. Examples of the group of heteroaryls that may be mentioned include furan, benzofuran, thiophene, benzothiophene, pyrrole, pyridine, pyrimidine, pyrazine, quinoline, isoquinoline, phthalazine, benzo[1,2,5]thiadiazole, benzothiazole, indole, benzotriazole, benzodioxolane, benzodioxane, carbazole, indole and quinazoline.

In connection with aryl and heteroaryl, the term substituted is understood to mean the substitution of the aryl or heteroaryl group by $R^{23}$, $OR^{23}$, a halogen, preferably F and/or Cl, a $CF_3$, a CN, an $NO_2$, an $NR^{24}R^{25}$, a $C_{1-6}$-alkyl (saturated), a $C_{1-6}$-alkoxy, a $C_{3-8}$-cycloalkoxy, a $C_{3-8}$-cycloalkyl or a $C_{2-6}$-alkylene.

In this connection the radical $R^{23}$ denotes H, a $C_{1-10}$-alkyl, preferably a $C_{1-6}$-alkyl, an aryl or heteroaryl radical, or an aryl or heteroaryl radical bonded via $C_{1-3}$-alkyl that is saturated or unsaturated, or a $C_{1-3}$-alkylene group, wherein these aryl and heteroaryl radicals may not themselves be substituted by aryl or heteroaryl radicals;

the radicals $R^{24}$ and $R^{25}$, which may be identical or different, denote H, a $C_{1-10}$-alkyl, preferably a $C_{1-6}$-alkyl, an aryl, a heteroaryl radical, or an aryl or heteroaryl radical bonded via a $C_{1-3}$-alkyl that is saturated or unsaturated, or a $C_{1-3}$-alkylene group, wherein these aryl and heteroaryl radicals may not themselves be substituted by aryl or heteroaryl radicals, or the radicals $R^{24}$ and $R^{25}$ together denote —$CH_2CH_2OCH_2CH_2$—, —$CH_2CH_2NR^{26}CH_2CH_2$— or $(CH_2)_{3-6}$ and the radical $R^{26}$ denotes H, a $C_{1-10}$-alkyl, preferably a $C_{1-6}$-alkyl, an aryl or heteroaryl radical, or an aryl or heteroaryl radical bonded via a $C_{1-3}$-alkyl that is saturated or unsaturated, or a $C_{1-3}$-alkylene group, wherein these aryl and heteroaryl radicals may not themselves be substituted by aryl or heteroaryl radicals.

The term salt is understood to mean any form of the active constituent according to the invention in which this adopts an ionic form or is charged and is coupled to a counterion (a cation or anion), and is present in solution. The term is also understood to include complexes of the active constituent with other molecules and ions, in particular complexes that are complexed via ionic interactions. In particular the term is understood to mean physiologically compatible salts with cations or bases and physiologically compatible salts with anions or acids.

The term physiologically compatible salts with cations or bases is understood within the context of the present invention to mean salts of at least one of the compounds according to the invention—generally of a (deprotonated) acid—as an anion with at least one, preferably inorganic cation, that are physiological compatible, especially when used in humans and/or mammals. Particularly preferred are the salts of alkali and alkaline earth metals, but also with $NH_4^+$, and in particular (mono) or (di)sodium, (mono) or (di)potassium, magnesium or calcium salts.

The term physiologically compatible salt with anions or acids is understood within the context of the present invention to mean salts of at least one of the compounds according to the invention—generally protonated, for example on the nitrogen atom—as a cation with at least one anion, that are physiologically compatible, especially when used in humans and/or mammals. In the context of the present invention the term is particularly understood to denote the salt formed with a physiologically compatible acid, namely salts of the respective active constituent with inorganic or organic acids, that are physiologically compatible, especially when used in humans and/or mammals. Examples of physiologically compatible salts of specific acids are salts of: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydro-1$\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid. The hydrochloride salt is particularly preferred.

All the substances listed hereinbefore and specified for use displace gabapentin from its binding site, which has also not yet been experimentally determined. This implies however that the substances according to the invention bind at the same binding site or receptor and act physiologically via the same receptor, presumably with the same activity profile as gabapentin. This assumption that the same activity is also exerted at the same binding site is demonstrated by the analgesic effect.

Thus, the compounds according to the invention not only displace gabapentin from its binding site but—like gabapentin—also have a marked analgesic effect. Accordingly, the invention provides for the use of the aforementioned and defined sulfonylguanidines in the previously mentioned medical indications in which gabapentin is active, i.e. in particular in the treatment of pain, epilepsy or migraine, but specifically also in neuropathic pain including hyperalgesia and allodynia, and other conditions for which the use of gabapentin is indicated.

Gabapentin is a known antiepileptic having an anticonvulsive action. In addition to this gabapentin is also used in various other medical conditions, and inter alia is prescribed by physicians for the treatment of migraine and bipolar disorders as well as hot flashes (e.g. in the post menopause) (M. Schrope, Modern Drug Discovery, September 2000, p. 11). Other medical conditions in which gabapentin exhibits a therapeutic potential have been identified in human studies and in clinical practice (J. S. Bryans, D. J. Wustrow; "3-Substituted GABA Analogs with Central Nervous System Activity: A Review" in Med. Res. Rev. (1999), pp. 149-177). The action of gabapentin is listed in detail in this review article. For example, gabapentin is effective in the treatment of chronic pain and behavioral disturbances. In particular the following properties of gabapentin are listed: anticonvulsive and antiepileptic actions, the use to treat chronic, neuropathic pain, in particular thermal hyperalgesia, mechanical allodynia, and cold-induced allodynia. In addition gabapentin is effective against neuropathy triggered by nerve damage, and in particular is also successful in treating neuropathic pain as well as inflammatory and post-operative pain. Gabapentin is also useful as an antipsychotic agent, in particular as an anxiolytic. Further proven indications for use include: amyotrophic lateral sclerosis (ALS), reflex sympathetic dystrophy (RSD), spastic palsy, restless leg syndrome, treatment of symptoms and pain caused by multiple sclerosis, acquired nystagmus, treatment of the symptoms of Parkinson's disease, painful diabetic neuropathy and psychiatric disorders, for example bipolar disorders, mood fluctuations, manic behavior. Gabapentin has also been successfully used to treat erythromelalgic pain, post-poliomyelitic pain, trigeminal neuralgia and post-herpetic neuralgia (Bryans and Wustrow (1999), etc.). The general efficacy of gabapentin in neurodegenerative conditions is generally known and is also demonstrated by the examples given in the aforementioned review article. Such neurodegenerative conditions include for example Alzheimer's disease, Huntington's disease, Parkinson's disease and epilepsy. The effectiveness of gabapentin in gastrointestinal disorders is also known.

In a preferred embodiment of the invention the following applies as regards the employed sulfonylguanidines according to the general tautomeric formulas I and Ia:

$R^1$ is selected from aryl or heteroaryl, in each case unsubstituted or singly or multiply substituted; or aryl or heteroaryl bonded via saturated or unsaturated $C_{1-3}$-alkyl, in each case unsubstituted or singly or multiply substituted;

preferably, $R^1$ is selected from aryl or heteroaryl that is unsubstituted or singly or multiply substituted, preferably with $NO_2$, $NH_2$, F, Cl, Br, I, OH or SH; or —NHC(O)—$C_{1-4}$-alkyl, —$C_{1-4}$-alkyl, —$OC_{1-4}$-alkyl, —$N(C_{1-4}$-alkyl$)_2$, where the $C_{1-4}$-alkyl group is in each case branched or unbranched, saturated or unsaturated, singly or multiply substituted or unsubstituted;

in particular, $R^1$ is selected from phenyl or naphthyl, especially phenyl, that is unsubstituted or singly or multiply substituted, preferably by F, Cl, Br, I, OH, $NO_2$, $NH_2$; $C_{1-4}$-alkyl, O—$C_{1-4}$-alkyl, in particular $CH_3$, $C_2H_5$, tert.-butyl, i-propyl, methoxy, $OCF_3$ or ethoxy, in each case branched or unbranched, saturated or unsaturated, singly or multiply substituted or unsubstituted; preferably substituted in the meta or para position and in particular in the para position.

In another preferred embodiment of the invention the following applies as regards the employed sulfonylguanidines according to the general tautomeric formulas I and Ia:

$R^2$ is selected from aryl or heteroaryl bonded via saturated or unsaturated $C_{1-3}$-alkyl, in particular $CH_2$, in each case unsubstituted or singly or multiply substituted;

preferably, $R^2$ is selected from heteroaryl bonded via saturated or unsaturated $C_{1-3}$-alkyl, in particular —$CH_2$—, in each case unsubstituted or singly or multiply substituted;

in particular, $R^2$ is selected from pyridinyl, thiophenyl, furanyl or pyrimidinyl, preferably pyridinyl, bonded via saturated or unsaturated $C_{1-3}$-alkyl, in particular —$CH_2$—, in each case unsubstituted or singly or multiply, preferably singly substituted, in particular by F, Cl, Br, I, OH, $NO_2$, SH, $NH_2$, $C_{1-4}$-alkyl, O—$C_{1-4}$-alkyl, preferably substituted in the para position.

In another preferred embodiment of the invention the following applies as regards the employed sulfonylguanidines according to the general tautomeric formulas I and Ia:

$R^3$ is selected from H or $C_{1-4}$-alkyl, preferably H or $CH_3$, in particular H.

In a preferred embodiment of the invention, the sulfonylguanidines employed are selected from the group consisting of:

N-{amino-[pyridin-2-yl-methyl)-amino]-methylene}-4-methylbenzenesulfonamide (1)

N-[amino-(benzylaminomethylene)]-4-methylbenzene-sulfonamide (2)

N-(aminomorpholin-4-yl-methylene)-4-methylbenzene-sulfonamide (3)

N-(aminocyclohexylaminomethylene)-4-methylbenzene-sulfonamide (4)

N-(aminophenylaminomethylene)-4-methylbenzene-sulfonamide (5)

N-[(amino-4-methoxybenzylamino)-methylene]-4-methylbenzene-sulfonamide (6)

N-[amino-(naphthalin-2-yl-amino)-methylene]-4-methyl-benzenesulfonamide (7)

N-[amino-(4-methylpiperazin-1-yl-amino)-methylene]-4-methylbenzenesulfonamide (8)

N-[amino-(N'-pyridin-2-yl-hydrazino)-methylene]-4-methylbenzenesulfonamide (9)

N-[aminopropylaminomethylene]-4-methylbenzene-sulfonamide (10)

N-(aminobutylaminomethylene)-4-methylbenzene-sulfonamide (11)

N-[aminobutylaminomethylene]-4-methylbenzene-sulfonamide (12)

N-[aminobutylaminomethylene]-4-methylbenzene-sulfonamide (13)

N-[aminophenethylaminomethylene]-4-methylbenzene-sulfonamide (14)

N-[amino-sec-butylaminomethylene]-4-methylbenzene-sulfonamide (15)

N-[amino-(N'-tosyl-2-yl-hydrazino)-4-methylbenzene-sulfonamide (16)

N-[amino-(2H-pyrazol-3-yl-amino)-methylene]-4-methylbenzenesulfonamide (17)

N-(aminopyrrolidin-1-yl-methylene)-4-methylbenzenesulfonamide (18)
N-[amino-(naphthalin-1-yl-amino)-methylene]-4-methylbenzenesulfonamide (19)
N-[amino-(morpholin-4-yl-amino)-methylene]-4-methylbenzenesulfonamide (20)
N-{amino-[(pyridin-2-yl-methyl)-amino]-methylene}-4-chlorobenzenesulfonamide (21)
N-{amino-[(pyridin-4-yl-methyl)-amino]-methylene}-4-methylbenzenesulfonamide (22)
N-{amino-[(pyridin-3-yl-methyl)-amino]-methylene}-4-methylbenzenesulfonamide (23)
N-[amino-(pyridin-3-yl-amino)-methylene]-4-methylbenzenesulfonamide (24)
N-(aminopyrrolidin-1-yl-methylene)-4-chlorobenzenesulfonamide (25)
N-(aminopyrrolidin-1-yl-methylene)-benzenesulfonamide (26)
N-(aminopyrrolidin-1-yl-methylene)-2-nitrobenzene-sulfonamide (27)
N-[amino-(morpholin-4-yl-amino)-methylene]-4-chlorobenzenesulfonamide (28)
N-[amino-(morpholin-4-yl-amino)-methylene]-benzenesulfonamide (29)
Naphthalene-1-sulfonic acid amino-(morpholin-4-yl-amino)-methylene amide (30)
N-{amino-[(pyridin-2-yl-methyl)-amino]-methylene}-C-phenylmethanesulfonamide (31)
N-{amino[(pyridin-2-yl-methyl)-amino]-methylene}-4-bromobenzenesulfonamide (32)
N-{amino[(pyridin-2-yl-methyl)-amino]-methylene}-3,4-dichlorobenzenesulfonamide (33)
N-{amino[(pyridin-2-yl-methyl)-amino]-methylene}-4-isopropylbenzenesulfonamide (34)
N-{amino[(pyridin-2-yl-methyl)-amino]-methylene}-4-iodobenzenesulfonamide (35)
N-{amino[(pyridin-2-yl-methyl)-amino]-methylene}-benzenesulfonamide (36)
Naphthalene-2-sulfonic acid amino-[(pyridin-2-yl-methyl)-amino]-methylene amide (37)
1-methyl-1H-imidazole-4-sulfonic acid amino-[(pyridin-2-yl-methyl)-amino]-methylene amide (38)
N-[4-({amino-[(pyridin-2-yl-methyl)-amino]-methylene}-sulfamoyl)-phenyl]-acetamide (39)
N-{amino[(pyridin-2-yl-methyl)-amino]-methylene}-4-fluorobenzenesulfonamide (40)
N-{amino[(pyridin-2-yl-methyl)-amino]-methylene}-2,4,6-trimethylbenzenesulfonamide (41)
N-{amino[(pyridin-2-yl-methyl)-amino]-methylene}-4-propylbenzenesulfonamide (42)
N-{amino[(pyridin-2-yl-methyl)-amino]-methylene}-4-methoxybenzenesulfonamide (43)
Naphthalene-1-sulfonic acid amino-[(pyridin-2-yl-methyl)-amino]-methylene amide (44)
N-{amino[(pyridin-2-yl-methyl)-amino]-methylene}-3-methylbenzenesulfonamide (45)
Thiophene-2-sulfonic acid amino-[(pyridin-2-yl-methyl)-amino]-methylene amide (46)
Quinoline-8-sulfonic acid amino-[(pyridin-2-yl-methyl)-amino]-methylene amide (47)
5-chloro-3-methylbenzo[b]thiophene-2-sulfonic acid amino-[(pyridin-2-yl-methyl)-amino]-methylene amide (48)
N-{amino[(pyridin-2-yl-methyl)-amino]-methylene}-4-tert.-butylbenzenesulfonamide (49)
N-{amino[(pyridin-2-yl-methyl)-amino]-methylene}-4-butylbenzenesulfonamide (50)
N-{amino[(pyrimidin-2-yl-methyl)-amino]-methylene}-4-tert.-butylbenzenesulfonamide (51)
N-{amino[(furan-2-yl-methyl)-amino]-methylene}-4-butylbenzenesulfonamide (52)
N-{amino[(furan-2-yl-methyl)-amino]-methylene}-4-methylbenzenesulfonamide (53)
N-{amino[(furan-2-yl-methyl)-amino]-methylene}-4-isopropylbenzenesulfonamide (54)
N-{amino[(furan-2-yl-methyl)-amino]-methylene}-4-propylbenzenesulfonamide (55)
N-{amino[(furan-2-yl-methyl)-amino]-methylene}-4-tert.-butylbenzenesulfonamide (56)
N-{amino[(thiophen-2-yl-methyl)-amino]-methylene}-4-butylbenzenesulfonamide (57)
N-{amino[(thiophen-2-yl-methyl)-amino]-methylene}-4-propylbenzenesulfonamide (58)
N-{amino[(thiophen-2-yl-methyl)-amino]-methylene}-4-isopropylbenzenesulfonamide (59)
N-{amino[(thiophen-2-yl-methyl)-amino]-methylene}-4-tert.-butylbenzenesulfonamide (60)
N-{amino[(thiophen-2-yl-methyl)-amino]-methylene}-4-chlorobenzenesulfonamide (61)
N-{amino[(thiophen-2-yl-methyl)-amino]-methylene}-4-methylbenzenesulfonamide (62), and
N-{amino[(furan-2-yl-methyl)-amino]-methylene}-4-chlorobenzenesulfonamide (63)

optionally in the form of their racemates, their pure stereoisomers, in particular enantiomers or diastereomers, or in the form of mixtures of the stereoisomers, in particular of the enantiomers or diastereomers, in an arbitrary mixture ratio; in the represented form or in the form of their acids or their bases; or in the form of their salts, in particular the physiologically compatible salts, preferably the hydrochloride or sodium salt; or in the form of their solvates, in particular the hydrates; in both tautomeric forms according to formulas I and Ia, exclusively in one of the tautomeric forms according to formulas I or Ia or also in mixtures of both forms according to formulas I and Ia wherein the preferred tautomeric form may vary from compound to compound depending for example on the state of aggregation or on the chosen solvent.

Preferred compounds according to the invention are selected from the group consisting of:
N-{amino-[pyridin-2-yl-methyl)-amino]-methylene}-4-methylbenzenesulfonamide (1)
N-[amino-(benzylaminomethylene)]-4-methylbenzenesulfonamide (2) N-(aminomorpholin-4-yl-methylene)-4-methylbenzene-sulfonamide (3)
N-(aminocyclohexylaminomethylene)-4-methylbenzenesulfonamide (4)
N-(aminophenylaminomethylene)-4-methylbenzene-sulfonamide (5)
N-[(amino-4-methoxybenzylamino)-methylene]-4-methylbenzene-sulfonamide (6)
N-[amino-(naphthalin-2-yl-amino)-methylene]-4-methylbenzenesulfonamide (7)
N-[amino-(4-methylpiperazin-1-yl-amino)-methylene]-4-methylbenzenesulfonamide (8)
N-[amino-(N'-pyridin-2-yl-hydrazino)-methylene]-4-methylbenzenesulfonamide (9)
N-[aminopropylaminomethylene]-4-methylbenzene-sulfonamide (10)
N-(aminobutylaminomethylene)-4-methylbenzene-sulfonamide (11)
N-[aminobutylaminomethylene]-4-methylbenzene-sulfonamide (12)
N-[aminobutylaminomethylene]-4-methylbenzene-sulfonamide (13)

N-[aminophenethylaminomethylene]-4-methylbenzenesulfonamide (14)
N-[amino-sec-butylaminomethylene]-4-methylbenzenesulfonamide (15)
N-[amino-(N'-tosyl-2-yl-hydrazino)-4-methylbenzenesulfonamide (16)
N-[amino-(2H-pyrazol-3-yl-amino)-methylene]-4-methylbenzenesulfonamide (17)
N-(aminopyrrolidin-1-yl-methylene)-4-methylbenzenesulfonamide (18)
N-[amino-(naphthalin-1-yl-amino)-methylene]-4-methyl-benzenesulfonamide (19)
N-[amino-(morpholin-4-yl-amino)-methylene]-4-methyl-benzenesulfonamide (20)
N-{amino-[(pyridin-2-yl-methyl)-amino]-methylene}-4-chlorobenzenesulfonamide (21)
N-{amino-[(pyridin-4-yl-methyl)-amino]-methylene}-4-methylbenzenesulfonamide (22)
N-{amino-[(pyridin-3-yl-methyl)-amino]-methylene}-4-methylbenzenesulfonamide (23)
N-[amino-(pyridin-3-yl-amino)-methylene]-4-methyl-benzenesulfonamide (24)
N-(aminopyrrolidin-1-yl-methylene)-4-chlorobenzenesulfonamide (25)
N-(aminopyrrolidin-1-yl-methylene)-benzenesulfonamide (26)
N-(aminopyrrolidin-1-yl-methylene)-2-nitrobenzene-sulfonamide (27)
N-[amino-(morpholin-4-yl-amino)-methylene]-4-chlorobenzenesulfonamide (28)
N-[amino-(morpholin-4-yl-amino)-methylene]-benzenesulfonamide (29)
Naphthalene-1-sulfonic acid amino-(morpholin-4-yl-amino)-methylene amide (30)
N-{amino[(pyridin-2-yl-methyl)-amino]-methylene}-4-bromobenzenesulfonamide (32)
N-{amino[(pyridin-2-yl-methyl)-amino]-methylene}-3,4-dichlorobenzenesulfonamide (33)
N-{amino[(pyridin-2-yl-methyl)-amino]-methylene}-4-isopropylbenzenesulfonamide (34)
N-{amino[(pyridin-2-yl-methyl)-amino]-methylene}-4-iodobenzenesulfonamide (35)
N-{amino[(pyridin-2-yl-methyl)-amino]-methylene}-benzenesulfonamide (36)
Naphthalene-2-sulfonic acid amino-[(pyridin-2-yl-methyl)-amino]-methylene amide (37)
N-[4-({amino-[(pyridin-2-yl-methyl)-amino]-methylene}-sulfamoyl)-phenyl]-acetamide (39)
N-{amino[(pyridin-2-yl-methyl)-amino]-methylene}-4-fluorobenzenesulfonamide (40)
N-{amino[(pyridin-2-yl-methyl)-amino]-methylene}-2,4,6-trimethylbenzenesulfonamide (41)
N-{amino[(pyridin-2-yl-methyl)-amino]-methylene}-4-propylbenzenesulfonamide (42)
N-{amino[(pyridin-2-yl-methyl)-amino]-methylene}-4-methoxybenzenesulfonamide (43)
Naphthalene-1-sulfonic acid amino-[(pyridin-2-yl-methyl)-amino]-methylene amide (44)
N-{amino[(pyridin-2-yl-methyl)-amino]-methylene}-3-methylbenzenesulfonamide (45)
Thiophene-2-sulfonic acid amino-[(pyridin-2-yl-methyl)-amino]-methylene amide (46)
Quinoline-8-sulfonic acid amino-[(pyridin-2-yl-methyl)-amino]-methylene amide (47)
5-chloro-3-methylbenzo[b]thiophene-2-sulfonic acid amino-[(pyridin-2-yl-methyl)-amino]-methylene amide (48)
N-{amino[(pyridin-2-yl-methyl)-amino]-methylene}-4-tert.-butylbenzenesulfonamide (49)
N-{amino[(pyridin-2-yl-methyl)-amino]-methylene}-4-butylbenzenesulfonamide (50)
N-{amino[(furan-2-yl-methyl)-amino]-methylene}-4-butylbenzenesulfonamide (52)
N-{amino[(furan-2-yl-methyl)-amino]-methylene}-4-methylbenzenesulfonamide (53)
N-{amino[(furan-2-yl-methyl)-amino]-methylene}-4-isopropylbenzenesulfonamide (54)
N-{amino[(furan-2-yl-methyl)-amino]-methylene}-4-propylbenzenesulfonamide (55)
N-{amino[(furan-2-yl-methyl)-amino]-methylene}-4-tert.-butylbenzenesulfonamide (56)
N-{amino[(thiophen-2-yl-methyl)-amino]-methylene}-4-butylbenzenesulfonamide (57)
N-{amino[(thiophen-2-yl-methyl)-amino]-methylene}-4-propylbenzenesulfonamide (58)
N-{amino[(thiophen-2-yl-methyl)-amino]-methylene}-4-isopropylbenzenesulfonamide (59)
N-{amino[(thiophen-2-yl-methyl)-amino]-methylene}-4-tert.-butylbenzenesulfonamide (60)
N-{amino[(thiophen-2-yl-methyl)-amino]-methylene}-4-chlorobenzenesulfonamide (61)
N-{amino[(thiophen-2-yl-methyl)-amino]-methylene}-4-methylbenzenesulfonamide (62), and
N-{amino[(furan-2-yl-methyl)-amino]-methylene}-4-chlorobenzenesulfonamide (63), especially
N-{amino-[(pyridin-2-yl-methyl)-amino]-methylene}-4-chlorobenzenesulfonamide (21)
N-{amino-[(pyridin-4-yl-methyl)-amino]-methylene}-4-methylbenzenesulfonamide (22)
N-{amino-[(pyridin-3-yl-methyl)-amino]-methylene}-4-methylbenzenesulfonamide (23)
N-{amino[(pyridin-2-yl-methyl)-amino]-methylene}-4-bromobenzenesulfonamide (32)
N-{amino[(pyridin-2-yl-methyl)-amino]-methylene}-3,4-dichlorobenzenesulfonamide (33)
N-{amino[(pyridin-2-yl-methyl)-amino]-methylene}-4-isopropylbenzenesulfonamide (34)
N-{amino[(pyridin-2-yl-methyl)-amino]-methylene}-4-iodobenzenesulfonamide (35)
N-{amino[(pyridin-2-yl-methyl)-amino]-methylene}-benzenesulfonamide (36)
Naphthalene-2-sulfonic acid amino-[(pyridin-2-yl-methyl)-amino]-methylene amide (37)
N-[4-({amino-[(pyridin-2-yl-methyl)-amino]-methylene}-sulfamoyl)-phenyl]-acetamide (39)
N-{amino[(pyridin-2-yl-methyl)-amino]-methylene}-4-fluorobenzenesulfonamide (40)
N-{amino[(pyridin-2-yl-methyl)-amino]-methylene}-2,4,6-trimethylbenzenesulfonamide (41)
N-{amino[(pyridin-2-yl-methyl)-amino]-methylene}-4-propylbenzenesulfonamide (42)
N-{amino[(pyridin-2-yl-methyl)-amino]-methylene}-4-methoxybenzenesulfonamide (43)
Naphthalene-1-sulfonic acid amino-[(pyridin-2-yl-methyl)-amino]-methylene amide (44)
N-{amino[pyridin-2-yl-methyl)-amino]-methylene}-3-methylbenzenesulfonamide (45)
Thiophene-2-sulfonic acid amino-[(pyridin-2-yl-methyl)-amino]-methylene amide (46)
Quinoline-8-sulfonic acid amino-[(pyridin-2-yl-methyl)-amino]-methylene amide (47)

5-chloro-3-methylbenzo[b]thiophene-2-sulfonic acid amino-[(pyridin-2-yl-methyl)-amino]-methylene amide (48)

N-{amino[(pyridin-2-yl-methyl)-amino]-methylene}-4-tert.-butylbenzenesulfonamide (49)

N-{amino[(pyridin-2-yl-methyl)-amino]-methylene}-4-butylbenzenesulfonamide (50)

N-{amino[(furan-2-yl-methyl)-amino]-methylene}-4-butylbenzenesulfonamide (52)

N-{amino[(furan-2-yl-methyl)-amino]-methylene}-4-methylbenzenesulfonamide (53)

N-{amino[(furan-2-yl-methyl)-amino]-methylene}-4-isopropylbenzenesulfonamide (54)

N-{amino[(furan-2-yl-methyl)-amino]-methylene}-4-propylbenzenesulfonamide (55)

N-{amino[(furan-2-yl-methyl)-amino]-methylene}-4-tert.-butylbenzenesulfonamide (56)

N-{amino[(thiophen-2-yl-methyl)-amino]-methylene}-4-butylbenzenesulfonamide (57)

N-{amino[(thiophen-2-yl-methyl)-amino]-methylene}-4-propylbenzenesulfonamide (58)

N-{amino[(thiophen-2-yl-methyl)-amino]-methylene}-4-isopropylbenzenesulfonamide (59)

N-{amino[(thiophen-2-yl-methyl)-amino]-methylene}-4-tert.-butylbenzenesulfonamide (60)

N-{amino[(thiophen-2-yl-methyl)-amino]-methylene}-4-chlorobenzenesulfonamide (61)

N-{amino[(thiophen-2-yl-methyl)-amino]-methylene}-4-methylbenzenesulfonamide (62), and N-{amino[(furan-2-yl-methyl)-amino]-methylene}-4-chlorobenzenesulfonamide (63), optionally in the form of their racemates, their pure stereoisomers, in particular enantiomers or diastereomers, or in the form of mixtures of the stereoisomers, in particular of the enantiomers or diastereomers, in an arbitrary mixture ratio; in the represented form or in the form of their acids or their bases; or in the form of their salts, in particular the physiologically compatible salts, preferably the hydrochloride or sodium salt; or in the form of their solvates, in particular the hydrates; in both tautomeric forms according to formulas I and Ia, exclusively in one of the tautomeric forms according to formulas I or Ia or also in mixtures of both forms according to formulas I and Ia wherein the preferred tautomeric form may vary from compound to compound depending for example on the state of aggregation or on the chosen solvent.

Further compounds from which are selected compounds that are preferably used according to the invention, optionally in the form or their racemates, their pure stereoisomers, in particular enantiomers or diastereomers, or in the form of mixtures of the stereoisomers, in particular of the enantiomers or diastereomers, in an arbitrary mixture ratio; in the represented form or in the form of their acids or bases or in the form of their salts, in particular of the physiologically compatible salts, preferably the hydrochloride or sodium salt; or in the form of their solvates, in particular the hydrates; in both tautomeric forms according to formulas I and Ia, exclusively in one of the tautomeric forms according to formulas I or Ia or also in mixtures of both forms according to formulas I and Ia, in which the preferred tautomeric form may vary from compound to compound for example depending on the state of aggregation or on the chosen solvent, are shown as structural formulas of FIGS. 1-40.

In this connection it is furthermore preferred if the sulfonylguanidine used according to the invention is present entirely or substantially entirely in the tautomeric form according to formula I.

The present invention preferably also provides sulfonylguanidines used according to the invention that are present entirely or substantially entirely in the tautomeric form according to formula Ia.

The invention moreover provides the sulfonylguanidines according to the general tautomeric formulas I and Ia,

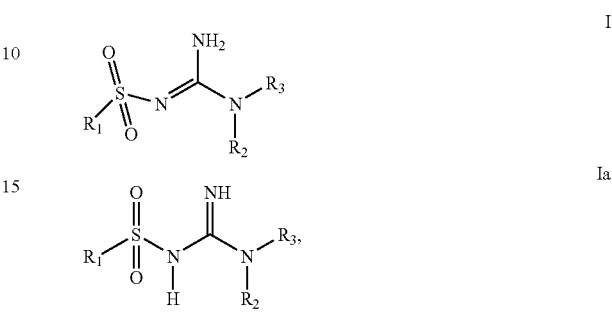

wherein $R^1$ is selected from $C_{1-10}$-alkyl that is branched or unbranched, saturated or unsaturated, singly or multiply substituted or unsubstituted; $C_{3-8}$-cycloalkyl or bicyclic alkylene, in each case saturated or unsaturated, singly or multiply substituted or unsubstituted; aryl or heteroaryl, in each case unsubstituted or singly or multiply substituted; or aryl, $C_{3-9}$-cycloalkyl or heteroaryl, bonded via saturated or unsaturated $C_{1-14}$-alkyl, in particular $C_{1-3}$-alkyl, in each case unsubstituted or singly or multiply substituted;

$R^2$ is selected from $C_{1-10}$-alkyl that is branched or unbranched, saturated or unsaturated, singly or multiply substituted or unsubstituted; $C_{3-8}$-cycloalkyl that is saturated or unsaturated, singly or multiply substituted or unsubstituted; aryl or heteroaryl, in each case unsubstituted or singly or multiply substituted; or aryl, $C_{3-9}$-cycloalkyl or heteroaryl, bonded via saturated or unsaturated $C_{1-3}$-alkyl, $S(O)_2$ or NH, in each case unsubstituted or singly or multiply substituted; or $NR^4R^5$, where $R^4$, $R^5$ independently of one another are selected from H; $C_{1-18}$-alkyl that is branched or unbranched, saturated or unsaturated, singly or multiply substituted or unsubstituted; $C_{3-8}$-cycloalkyl that is saturated or unsaturated, singly or multiply substituted or unsubstituted; aryl or heteroaryl, in each case unsubstituted or singly or multiply substituted; or aryl, $C_{3-9}$-cycloalkyl or heteroaryl, bonded via saturated or unsaturated $C_{1-3}$-alkyl, in each case unsubstituted or singly or multiply substituted; or $SO_2R^6$, where $R^6$ is selected from $C_{1-18}$-alkyl that is branched or unbranched, saturated or unsaturated, singly or multiply substituted or unsubstituted; $C_{3-8}$-cycloalkyl that is saturated or unsaturated, singly or multiply substituted or unsubstituted; aryl or heteroaryl, in each case unsubstituted or singly or multiply substituted; or aryl, $C_{3-9}$-cycloalkyl or heteroaryl, bonded via saturated or unsaturated $C_{1-3}$-alkyl, in each case unsubstituted or singly or multiply substituted;

or $R^4$ and $R^5$ together form —$CH_2CH_2OCH_2CH_2$—;

—$CH_2CH_2N(R^7)CH_2CH_2$, where $R^7$ is selected from $C_{1-18}$-alkyl that is branched or unbranched, saturated or unsaturated, singly or multiply substituted or unsubstituted; $C_{3-8}$-cycloalkyl that is saturated or unsaturated, singly or multiply substituted or unsubstituted; aryl or heteroaryl, in each case unsubstituted or singly or multiply substituted; or aryl, $C_{3-9}$-cycloalkyl or heteroaryl, bonded via saturated or unsaturated $C_{1-3}$-alkyl, in each case unsubstituted or singly or multiply substituted;

$R^3$ is selected from H, $C_{1-10}$-alkyl that is branched or unbranched, saturated or unsaturated, singly or multiply substituted or unsubstituted; $C_{3-8}$-cycloalkyl that is saturated or unsaturated, singly or multiply substituted or unsubstituted; aryl or heteroaryl, in each case unsubstituted or singly or multiply substituted; or aryl, $C_{3-9}$-cycloalkyl or heteroaryl, bonded via saturated or unsaturated $C_{1-3}$-alkyl, in each case unsubstituted or singly or multiply substituted;

or $R^2$ and $R^3$ together form $—CH_2(CH_2)_nCH_2—$, where n=2 or 3, $—CH_2CH_2OCH_2CH_2—$, or $—CH_2CH_2N(R^8)CH_2CH_2—$ where $R^8$ is selected from $C_{1-18}$-alkyl that is branched or unbranched, saturated or unsaturated, singly or multiply substituted or unsubstituted; $C_{3-8}$-cycloalkyl or bicyclic alkylene that is saturated or unsaturated, singly or multiply substituted or unsubstituted; aryl or heteroaryl, in each case unsubstituted or singly or multiply substituted; or aryl, $C_{3-9}$-cycloalkyl or heteroaryl, bonded via saturated or unsaturated $C_{1-3}$-alkyl, in each case unsubstituted or singly or multiply substituted;

optionally in the form of their racemates, their pure stereoisomers, in particular enantiomers or diastereomers, or in the form of mixtures of the stereoisomers, in particular of the enantiomers or diastereomers, in an arbitrary mixture ratio; in the represented form or in the form of their acids or bases or in the form of their salts, in particular of the physiologically compatible salts, or in the form of their solvates, in particular the hydrates; in both tautomeric forms according to formulas I and Ia, exclusively in one of the tautomeric forms according to formulas I or Ia or also in mixtures of both forms according to formulas I and Ia, in which the preferred tautomeric form may vary from compound to compound depending on the state of aggregation or on the chosen solvent.

In one embodiment of the invention the following applies as regards the sulfonylguanidines according to the invention of the general tautomeric formulas I and Ia:

$R^1$ is selected from $C_{1-10}$-alkyl that is branched or unbranched, saturated or unsaturated, singly or multiply substituted or unsubstituted; $C_{3-8}$-cycloalkyl or bicyclic alkylene, in each case saturated or unsaturated, singly or multiply substituted or unsubstituted; phenyl that is unsubstituted or singly or multiply substituted.

In another embodiment of the invention the following applies as regards the sulfonylguanidines according to the invention of the general tautomeric formulas I and Ia:

$R^2$ is selected from $C_{1-10}$-alkyl that is branched or unbranched, saturated or unsaturated, singly or multiply substituted or unsubstituted; $C_{3-8}$-cycloalkyl that is saturated or unsaturated, singly or multiply substituted or unsubstituted; aryl or heteroaryl, in each case unsubstituted or singly or multiply substituted; or aryl, $C_{3-9}$-cycloalkyl or heteroaryl, bonded via saturated or unsaturated $C_{1-3}$-alkyl, in each case unsubstituted or singly or multiply substituted, In yet a further embodiment of the invention the following applies as regards the sulfonylguanidines according to the invention of the general tautomeric formulas I and Ia:

$R^3$ is selected from H or $CH_3$.

In a further embodiment of the invention the following applies as regards the sulfonylguanidines according to the invention of the general tautomeric formulas I and Ia:

$R^2$ and $R^3$ together form $—CH_2(CH_2)_nCH_2—$, where n=2 or 3, $—CH_2CH_2OCH_2CH_2—$, or $—CH_2CH_2N(R^8)CH_2CH_2—$.

In a particularly preferred embodiment of the invention the following applies as regards the sulfonylguanidines according to the invention of the general tautomeric formulas I and Ia:

$R^1$ is selected from aryl or heteroaryl, in each case unsubstituted or singly or multiply substituted;

$R^2$ is selected from aryl or heteroaryl, in each case unsubstituted or singly or multiply substituted and bonded via saturated or unsaturated $C_{1-3}$-alkyl, and $R^3$ is hydrogen, with the exception of compounds in which $R^2$ denotes phenyl bonded via $CH_2$ and $R^1$ denotes phenyl substituted or unsubstituted by methyl or $NH_2$, also with a condensed-on ring system.

In a preferred embodiment of the invention the following applies as regards the sulfonylguanidines according to the invention of the general tautomeric formulas I and Ia:

$R^1$ is selected from aryl or heteroaryl that is unsubstituted or singly or multiply substituted with $NO_2$, $NH_2$, F, Cl, Br, I, OH or SH; or $—NHC(O)—C_{1-4}$-alkyl, $—C_{1-4}$-alkyl, $—OC_{1-4}$-alkyl, $—N(C_{1-4}$-alkyl$)_2$, where the $C_{1-4}$-alkyl group is in each case branched or unbranched, saturated or unsaturated, singly or multiply substituted or unsubstituted;

in particular, $R^1$ is selected from phenyl or naphthyl, in particular phenyl, that is unsubstituted or singly or multiply substituted by F, Cl, Br, I, OH, $NO_2$, $NH_2$; $C_{1-4}$-alkyl, $O—C_{1-4}$-alkyl, in particular $CH_3$, $C_2H_5$, i-propyl, tert.-butyl, methoxy, $OCF_3$ or ethoxy, in each case branched or unbranched, saturated or unsaturated, singly or multiply substituted or unsubstituted; preferably substituted in the meta or para position and in particular in the para position.

In a preferred embodiment of the invention the following applies as regards the sulfonylguanidines according to the invention of the general tautomeric formulas I and Ia:

$R^2$ is selected from heteroaryl bonded via saturated or unsaturated $C_{1-3}$-alkyl, in particular $—CH_2—$, in each case unsubstituted or singly or multiply substituted;

in particular, $R^2$ is selected from pyridinyl, thiophenyl, furanyl or pyrimidinyl, preferably pyridinyl, bonded via saturated or unsaturated $C_{1-3}$-alkyl, in particular $—CH_2—$, in each case unsubstituted or singly or multiply, preferably singly substituted, in particular by F, Cl, Br, I, OH, $NO_2$, SH, $NH_2$, $C_{1-4}$-alkyl, $O—C_{1-4}$-alkyl, preferably substituted in the para position.

In one embodiment of the invention the sulfonylguanidines according to the invention are selected from the following group:

N-{amino-[pyridin-2-yl-methyl)-amino]-methylene}-4-methylbenzenesulfonamide (1)

N-[amino-(benzylaminomethylene)]-4-methylbenzene-sulfonamide (2)

N-(aminomorpholin-4-yl-methylene)-4-methylbenzene-sulfonamide (3)

N-(aminocyclohexylaminomethylene)-4-methylbenzene-sulfonamide (4)

N-(aminophenylaminomethylene)-4-methylbenzene-sulfonamide (5)

N-[(amino-4-methoxybenzylamino)-methylene]-4-methylbenzene-sulfonamide (6)

N-[amino-(naphthalin-2-yl-amino)-methylene]-4-methyl-benzenesulfonamide (7)
N-[amino-(4-methylpiperazin-1-yl-amino)-methylene]-4-methylbenzenesulfonamide (8)
N-[amino-(N'-pyridin-2-yl-hydrazino)-methylene]-4-methylbenzenesulfonamide (9)
N-[aminopropylaminomethylene]-4-methylbenzene-sulfonamide (10)
N-(aminobutylaminomethylene)-4-methylbenzene-sulfonamide (11)
N-[aminobutylaminomethylene]-4-methylbenzene-sulfonamide (12)
N-[aminobutylaminomethylene]-4-methylbenzene-sulfonamide (13)
N-[aminophenethylaminomethylene]-4-methylbenzene-sulfonamide (14)
N-[amino-sec-butylaminomethylene]-4-methylbenzene-sulfonamide (15)
N-[amino-(N'-tosyl-2-yl-hydrazino)-4-methylbenzene-sulfonamide (16)
N-[amino-(2H-pyrazol-3-yl-amino)-methylene]-4-methylbenzenesulfonamide (17)
N-(aminopyrrolidin-1-yl-methylene)-4-methylbenzene-sulfonamide (18)
N-[amino-(naphthalin-1-yl-amino)-methylene]-4-methyl-benzenesulfonamide (19)
N-[amino-(morpholin-4-yl-amino)-methylene]-4-methyl-benzenesulfonamide (20)
N-{amino-[(pyridin-2-yl-methyl)-amino]-methylene}-4-chlorobenzenesulfonamide (21)
N-{amino-[(pyridin-4-yl-methyl)-amino]-methylene}-4-methylbenzenesulfonamide (22)
N-{amino-[(pyridin-3-yl-methyl)-amino]-methylene}-4-methylbenzenesulfonamide (23)
N-[amino-(pyridin-3-yl-amino)-methylene]-4-methyl-benzenesulfonamide (24)
N-(aminopyrrolidin-1-yl-methylene)-4-chlorobenzene-sulfonamide (25)
N-(aminopyrrolidin-1-yl-methylene)-benzenesulfona-mide (26)
N-(aminopyrrolidin-1-yl-methylene)-2-nitrobenzene-sulfonamide (27)
N-[amino-(morpholin-4-yl-amino)-methylene]-4-chlorobenzenesulfonamide (28)
N-[amino-(morpholin-4-yl-amino)-methylene]-benzene-sulfonamide (29)
Naphthalene-1-sulfonic acid amino-(morpholin-4-yl-amino)-methylene amide (30)
N-{amino-[(pyridin-2-yl-methyl)-amino]-methylene}-C-phenylmethanesulfonamide (31)
N-{amino[(pyridin-2-yl-methyl)-amino]-methylene}-4-bromobenzenesulfonamide (32)
N-{amino[(pyridin-2-yl-methyl)-amino]-methylene}-3,4-dichlorobenzenesulfonamide (33)
N-{amino[(pyridin-2-yl-methyl)-amino]-methylene}-4-isopropylbenzenesulfonamide (34)
N-{amino[(pyridin-2-yl-methyl)-amino]-methylene}-4-iodobenzenesulfonamide (35)
N-{amino[(pyridin-2-yl-methyl)-amino]-methylene}-benzenesulfonamide (36)
Naphthalene-2-sulfonic acid amino-[(pyridin-2-yl-methyl)-amino]-methylene amide (37)
1-methyl-1H-imidazole-4-sulfonic acid amino-[(pyridin-2-yl-methyl)-amino]-methylene amide (38)
N-[4-({amino-[(pyridin-2-yl-methyl)-amino]-methyl-ene}-sulfamoyl)-phenyl]-acetamide (39)
N-{amino[(pyridin-2-yl-methyl)-amino]-methylene}-4-fluorobenzenesulfonamide (40)
N-{amino[(pyridin-2-yl-methyl)-amino]-methylene}-2,4,6-trimethylbenzenesulfonamide (41)
N-{amino[(pyridin-2-yl-methyl)-amino]-methylene}-4-propylbenzenesulfonamide (42)
N-{amino[(pyridin-2-yl-methyl)-amino]-methylene}-4-methoxybenzenesulfonamide (43)
Naphthalene-1-sulfonic acid amino-[(pyridin-2-yl-methyl)-amino]-methylene amide (44)
N-{amino[(pyridin-2-yl-methyl)-amino]-methylene}-3-methylbenzenesulfonamide (45)
Thiophene-2-sulfonic acid amino-[(pyridin-2-yl-methyl)-amino]-methylene amide (46)
Quinoline-8-sulfonic acid amino-[(pyridin-2-yl-methyl)-amino]-methylene amide (47)
5-chloro-3-methylbenzo[b]thiophene-2-sulfonic acid amino-[(pyridin-2-yl-methyl)-amino]-methylene amide (48)
N-{amino[(pyridin-2-yl-methyl)-amino]-methylene}-4-tert.-butylbenzenesulfonamide (49)
N-{amino[(pyridin-2-yl-methyl)-amino]-methylene}-4-butylbenzenesulfonamide (50)
N-{amino[(pyrimidin-2-yl-methyl)-amino]-methylene}-4-tert.-butylbenzenesulfonamide (51)
N-{amino[(furan-2-yl-methyl)-amino]-methylene}-4-butylbenzenesulfonamide (52)
N-{amino[(furan-2-yl-methyl)-amino]-methylene}-4-methylbenzenesulfonamide (53)
N-{amino[(furan-2-yl-methyl)-amino]-methylene}-4-isopropylbenzenesulfonamide (54)
N-{amino[(furan-2-yl-methyl)-amino]-methylene}-4-propylbenzenesulfonamide (55)
N-{amino[(furan-2-yl-methyl)-amino]-methylene}-4-tert.-butylbenzenesulfonamide (56)
N-{amino[(thiophen-2-yl-methyl)-amino]-methylene}-4-butylbenzenesulfonamide (57)
N-{amino[(thiophen-2-yl-methyl)-amino]-methylene}-4-propylbenzenesulfonamide (58)
N-{amino[(thiophen-2-yl-methyl)-amino]-methylene}-4-isopropylbenzenesulfonamide (59)
N-{amino[(thiophen-2-yl-methyl)-amino]-methylene}-4-tert.-butylbenzenesulfonamide (60)
N-{amino[(thiophen-2-yl-methyl)-amino]-methylene}-4-chlorobenzenesulfonamide (61)
N-{amino[(thiophen-2-yl-methyl)-amino]-methylene}-4-methylbenzenesulfonamide (62)
N-{amino[(furan-2-yl-methyl)-amino]-methylene}-4-chlorobenzenesulfonamide (63)

optionally in the form of their racemates, their pure stereoisomers, in particular enantiomers or diastereomers, or in the form of mixtures of the stereoisomers, in particular of the enantiomers or diastereomers, in an arbitrary mixture ratio; in the represented form or in the form of their acids or their bases; or in the form of their salts, in particular the physiologically compatible salts, preferably the hydrochloride or sodium salt; or in the form of their solvates, in particular the hydrates; in both tautomeric forms according to formulas I and Ia, exclusively in one of the tautomeric forms according to formulas I or Ia or also in mixtures of both forms according to formulas I and Ia, wherein the preferred tautomeric form may vary from compound to compound depending for example on the state of aggregation or on the chosen solvent.

In a particularly preferred embodiment of the invention the sulfonylguanidines according to the invention are selected from the following group:

N-{amino-[pyridin-2-yl-methyl)-amino]-methylene}-4-methylbenzenesulfonamide (1)
N-[amino-(benzylaminomethylene)]-4-methylbenzenesulfonamide (2)
N-[(amino-4-methoxybenzylamino)-methylene]-4-methylbenzene-sulfonamide (6)
N-[aminophenethylaminomethylene]-4-methylbenzenesulfonamide (14)
N-{amino-[(pyridin-2-yl-methyl)-amino]-methylene}-4-chlorobenzenesulfonamide (21)
N-{amino-[(pyridin-4-yl-methyl)-amino]-methylene}-4-methylbenzenesulfonamide (22)
N-{amino-[(pyridin-3-yl-methyl)-amino]-methylene}-4-methylbenzenesulfonamide (23)
N-{amino[(pyridin-2-yl-methyl)-amino]-methylene}-4-bromobenzenesulfonamide (32)
N-{amino[(pyridin-2-yl-methyl)-amino]-methylene}-3,4-dichlorobenzenesulfonamide (33)
N-{amino[(pyridin-2-yl-methyl)-amino]-methylene}-4-isopropylbenzenesulfonamide (34)
N-{amino[(pyridin-2-yl-methyl)-amino]-methylene}-4-iodobenzenesulfonamide (35)
N-{amino[(pyridin-2-yl-methyl)-amino]-methylene}-benzenesulfonamide (36)
Naphthalene-2-sulfonic acid amino-[(pyridin-2-yl-methyl)-amino]-methylene amide (37)
1-methyl-1H-imidazole-4-sulfonic acid amino-[(pyridin-2-yl-methyl)-amino]-methylene amide (38)
N-[4-({amino-[(pyridin-2-yl-methyl)-amino]-methylene}-sulfamoyl)-phenyl]-acetamide (39)
N-{amino[(pyridin-2-yl-methyl)-amino]-methylene}-4-fluorobenzenesulfonamide (40)
N-{amino[(pyridin-2-yl-methyl)-amino]-methylene}-2,4,6-trimethylbenzenesulfonamide (41)
N-{amino[(pyridin-2-yl-methyl)-amino]-methylene}-4-propylbenzenesulfonamide (42)
N-{amino[(pyridin-2-yl-methyl)-amino]-methylene}-4-methoxybenzenesulfonamide (43)
Naphthalene-1-sulfonic acid amino-[(pyridin-2-yl-methyl)-amino]-methylene amide (44)
N-{amino[(pyridin-2-yl-methyl)-amino]-methylene}-3-methylbenzenesulfonamide (45)
Thiophene-2-sulfonic acid amino-[(pyridin-2-yl-methyl)-amino]-methylene amide (46)
Quinoline-8-sulfonic acid amino-[(pyridin-2-yl-methyl)-amino]-methylene amide (47)
5-chloro-3-methylbenzo[b]thiophene-2-sulfonic acid amino-[(pyridin-2-yl-methyl)-amino]-methylene amide (48)
N-{amino[(pyridin-2-yl-methyl)-amino]-methylene}-4-tert.-butylbenzenesulfonamide (49)
N-{amino[(pyridin-2-yl-methyl)-amino]-methylene}-4-butylbenzenesulfonamide (50)
N-{amino[(pyrimidin-2-yl-methyl)-amino]-methylene}-4-tert.-butylbenzenesulfonamide (51)
N-{amino[(furan-2-yl-methyl)-amino]-methylene}-4-butylbenzenesulfonamide (52)
N-{amino[(furan-2-yl-methyl)-amino]-methylene}-4-methylbenzenesulfonamide (53)
N-{amino[(furan-2-yl-methyl)-amino]-methylene}-4-isopropylbenzenesulfonamide (54)
N-{amino[(furan-2-yl-methyl)-amino]-methylene}-4-propylbenzenesulfonamide (55)
N-{amino[(furan-2-yl-methyl)-amino]-methylene}-4-tert.-butylbenzenesulfonamide (56)
N-{amino[(thiophen-2-yl-methyl)-amino]-methylene}-4-butylbenzenesulfonamide (57)
N-{amino[(thiophen-2-yl-methyl)-amino]-methylene}-4-propylbenzenesulfonamide (58)
N-{amino[(thiophen-2-yl-methyl)-amino]-methylene}-4-isopropylbenzenesulfonamide (59)
N-{amino[(thiophen-2-yl-methyl)-amino]-methylene}-4-tert.-butylbenzenesulfonamide (60)
N-{amino[(thiophen-2-yl-methyl)-amino]-methylene}-4-chlorobenzenesulfonamide (61)
N-{amino[(thiophen-2-yl-methyl)-amino]-methylene}-4-methylbenzenesulfonamide (62), and
N-{amino[(furan-2-yl-methyl)-amino]-methylene}-4-chlorobenzenesulfonamide (63)

optionally in the form of their racemates, their pure stereoisomers, in particular enantiomers or diastereomers, or in the form of mixtures of the stereoisomers, in particular of the enantiomers or diastereomers, in an arbitrary mixture ratio; in the represented form or in the form of their acids or their bases; or in the form of their salts, in particular the physiologically compatible salts, preferably the hydrochloride or sodium salt; or in the form of their solvates, in particular the hydrates; in both tautomeric forms according to formulas I and Ia, exclusively in one of the tautomeric forms according to formulas I or Ia or also in mixtures of both forms according to formulas I and Ia, wherein the preferred tautomeric form may vary from compound to compound depending for example on the state of aggregation or on the chosen solvent.

Further compounds which are preferred according to the invention are selected in the form of their racemates, enantiomers, diastereomers, in particular mixtures of their enantiomers or diastereomers or of an individual enantiomer or diastereomer, optionally in the form of their racemates, their pure stereoisomers, in particular enantiomers or diastereomers, or in the form of mixtures of these stereoisomers, in particular the enantiomers or diastereomers, in an arbitrary mixture ratio, in the represented form or in the form of their acids or their bases, or in the form of their salts, in particular in the form of the physiologically compatible salts, preferably the hydrochloride or sodium salt, or in the form of their solvates, in particular the hydrates, in both tautomeric forms according to formulas I and Ia, exclusively in one of the tautomeric forms according to formulas I or Ia, or also in mixtures of both forms according to formulas I and Ia, wherein the preferred tautomeric form may vary from compound to compound depending for example on the state of aggregation or the chosen solvent, from the group of compounds shown as structural formulas in FIGS. 1-40.

In this connection, it is furthermore preferred if the sulfonylguanidine according to the invention is present entirely or substantially entirely in the tautomeric form according to formula I.

The present invention similarly preferably provides sulfonylguanidines according to the invention that are present invention entirely or substantially entirely in the tautomeric form according to formula Ia.

The sulfonylguanidines according to the invention are toxicologically harmless, with the result that they are suitable as a pharmaceutically active constituent in medicaments. The invention accordingly also provides medicaments containing at least one sulfonylguanidine according to the invention, as well as optionally suitable additives and/or auxiliary substances and/or optionally further active constituents.

The same applies to the sulfonylguanidines used according to the invention in the aforementioned medical conditions, since also the sulfonylguanidines used according to the invention are naturally toxicologically harmless, with the result that they are suitable for use as a pharmaceutical active constituent in medicaments. The invention furthermore also provides medicaments containing at least one of the sulfonylguanidines used according to the invention, as well as optionally suitable additives and/or auxiliary substances and/or optionally further active constituents.

The pharmaceutical compositions according to the invention contain in addition to at least one sulfonylguanidine according to the invention or used according to the invention, optionally suitable additives and/or auxiliary substances, i.e. also carrier materials, fillers, solvents, diluents, colourants and/or binders, and may be administered as liquid medicament forms in the form of injection solutions, droplets or juices, or as semi-solid medicament forms in the form of granules, tablets, pellets, patches, capsules, plasters or aerosols. The choice of the auxiliary substances, etc., as well as the amounts thereof to be used depend on whether the medicament is to be administered orally, perorally, parenterally, intravenously, intraperitoneally, intradermally, intramuscularly, intranasally, buccally, rectally or topically, for example to the skin, the mucous membranes or the eyes. For oral administration, preparations in the form of tablets, sugar-coated pills, capsules, granules, drops, juices and syrups are suitable, while for parenteral, topical and inhalative application, solutions, suspensions, readily reconstitutable dry preparations as well as sprays are suitable. Sulfonylguanidines according to the invention in a depth form, in dissolved form or in a plaster, optionally with the addition of agents promoting skin penetration, are suitable percutaneous application preparations. Orally or percutaneously usable preparation forms may provide for a delayed release of the sulfonylguanidines according to the invention used according to the invention. In principle further active constituents known to the person skilled in the art may be added to the medicaments according to the invention.

The amount of active constituent to be administered to the patient varies depending on the patient's weight, type of application, medical indication and the severity of the condition. Normally 0.005 to 1000 mg/kg, preferably 0.05 to 5 mg/kg of at least one sulfonylguanidine according to the invention used according to the invention are applied.

In a preferred form of the medicament, a contained sulfonylguanidine according to the invention used according to the invention is present as a pure diastereomer and/or enantiomer, as a racemate, or as a non-equimolar or equimolar mixture of the diastereomers and/or enantiomers and/or exclusively in one of the tautomeric forms according to formulas I or Ia or also in mixtures of both forms according to formulas I and Ia.

The invention moreover provides for the use of a sulfonylguanidine according to the invention of the general tautomeric formulas I and Ia for the production of a medicament for treating pain, in particular neuropathic, chronic or acute pain, epilepsy and/or migraine, or for the production of a medicament for the treatment of hyperalgesia and allodynia, in particular thermal hyperalgesia, mechanical hyperalgesia and allodynia and cold-induced allodynia, or inflammatory or post-operative pain, or for the production of a medicament for the treatment of hot flashes, post-menopausal symptoms, amyotropic lateral sclerosis (ALS), reflex sympathetic dystrophy (RSD), spastic paralysis, restless leg syndrome, acquired nystagmus; psychiatric or neuropathological disorders such as bipolar disorders, anxiety, panic attacks, mood fluctuations, manic behavior, depression, manic-depressive behavior; painful diabetic neuropathy, symptoms and pain due to multiple sclerosis or Parkinson's disease, neurodegenerative diseases such as Alzheimer's disease, Huntington's disease, Parkinson's disease and epilepsy; gastrointestinal lesions; erythromelalgic or post-poliomyelitic pain, trigeminal or post-herpetic neuralgia; or as an anticonvulsant, analgesic or anxiolytic.

With each of the aforementioned compounds according to the invention, it may be preferred if the sulfonylguanidine that is used is present as a pure diastereomer and/or enantiomer, as a racemate or as a non-equimolar or equimolar mixture of the diastereomers and/or enantiomers and/or exclusively in one of the tautomeric forms according to formulas I or Ia or also in mixtures of both forms according to formulas I and Ia.

The invention additionally provides a process for treating a person or non-human mammal that requires treatment of medically relevant symptoms by administration of a therapeutically effective dose of a sulfonylguanidine according to the invention or used according to the invention, or of a medicament according to the invention. The invention relates in particular to suitable processes for treating pain, in particular neuropathic, chronic or acute pain, including migraine, hyperalgesia and allodynia, especially thermal hyperalgesia, mechanical hyperalgesia and allodynia and cold-induced allodynia, or for treating inflammatory or post-operative pain, epilepsy, hot flashes, post-menopausal symptoms, amyotropic lateral sclerosis (ALS), reflex sympathetic dystrophy (RSD), spastic paralysis, restless leg syndrome, acquired nystagmus; psychiatric or neuropathological disorders such as bipolar disorders, anxiety, panic attacks, mood fluctuations, manic behavior, depression, manic-depressive behavior; painful diabetic neuropathy, symptoms and pain due to multiple sclerosis or Parkinson's disease, neurodegenerative diseases such as Alzheimer's disease, Huntington's disease, Parkinson's disease and epilepsy; erythromelalgic or post-poliomyelitic pain, trigeminal or post-herpetic neuralgia.

The present invention moreover provides a process for the preparation of a sulfonylguanidine according to the invention as illustrated in the following description and examples.

Synthesis Procedure

The synthesis of the compounds according to the invention is carried out by reacting pyrazolesulfonic acid amides of the general formula II, which are synthesised by methods known in the literature (Larock, $2^{nd}$ Edition), with a wide range of various primary or secondary amines in the presence of methanesulfonic acid. $R^1$ to $R^3$ have in this connection the meanings given above for compounds of the formula I.

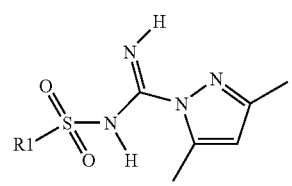

II

The reactions are preferably carried out in acetonitrile at a bath temperature of preferably 0° C. to 110° C., in particular at a bath temperature of 100° C. to 110° C.

The compounds of the formula I may also be converted in a manner known per se into their salts with physiologically compatible acids, preferably hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid and in particular hydrochloric acid. The salt formation is preferably carried out in a solvent, preferably diethyl ether, diisopropyl ether, acetic acid alkyl esters, acetone or 2-butanone, or a mixture of these solvents. Alternatively, trimethylsilane in aqueous solution is also suitable for the production of the hydrochlorides.

Salt Formation

The compounds of the formula I can be converted into their salts in a known manner with physiologically compatible acids, for example hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydro-1$\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid. The salt formation is preferably carried out in a solvent, for example diethyl ether, diisopropyl ether, alkyl esters of acetic acid, acetone and/or 2-butanone or also water. For the production of the hydrochlorides, trimethylchlorosilane in aqueous solution is moreover suitable.

The invention is described in further detail hereinafter with reference to examples and figures, without however being restricted thereto.

EXAMPLES

Figure 1:
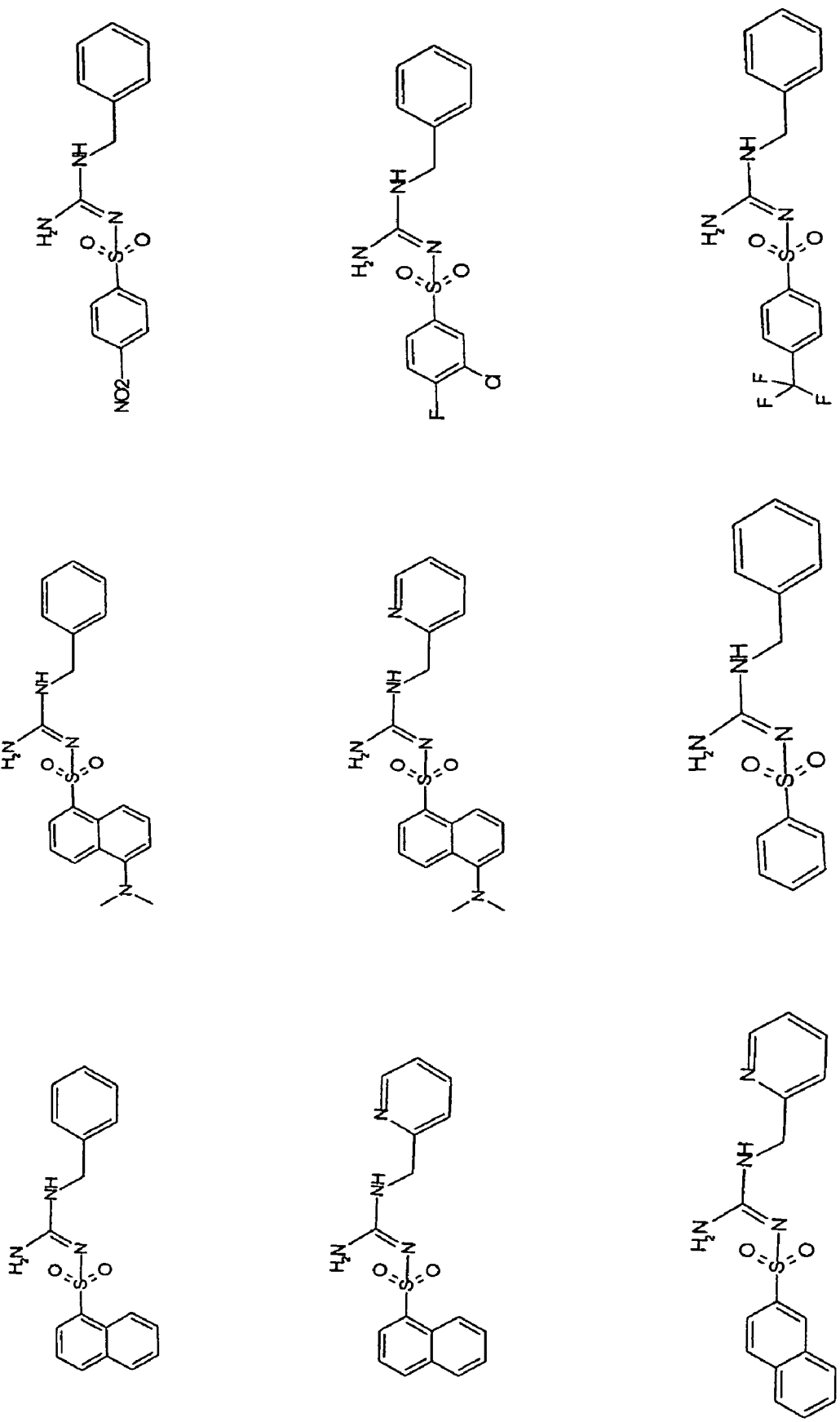
FIGS. 1-40 show further compounds produced according to the following processes, in particular according to the basic process 1, Example 0, which are shown as structural formulas in the figures. In the examples the compounds are compounds according to the invention and/or compounds that can be used according to the invention on account of their action structure.

The following examples illustrate compounds according to the invention as well as their preparation and investigations of the efficacy of the said compounds. The compounds were generally chosen in the tautomeric form according to formula I. However, it should be understood that the compounds may be present in one or other of the forms and accordingly this form of the compound does not or should not represent any restriction on the one or other tautomeric form.

The following details apply in general:

The chemicals and solvents used were commercially obtained from customary suppliers (Acros, Avocado, Aldrich, Fluka, Lancaster, Maybridge, Merck, Sigma, TCI etc.) or were synthesised.

The analysis was carried out by ESI mass spectrometry or HPLC.

An ESI-MS was recorded in each case for purposes of characterisation.

The following examples illustrate compounds that may be contained in substance databanks as well as the preparation thereof, and efficacy investigations carried out with the said compounds.

The following details apply in general:

The chemicals and solvents used were commercially obtained from customary suppliers (Acros, Avocado, Aldrich, Fluka, Lancaster, Maybridge, Merck, Sigma, TCI etc. or were synthesised).

The analysis was carried out by ESI mass spectrometry and/or $^1$H-NMR (Examples 1-21). For the Examples 22-30 according to the invention, only mass spectroscopy data are available.

Example 0

Basic Process 1

A small round-bottomed threaded glass tube (diameter 16 mm, length 125 mm) was provided manually with a stirrer and sealed on the Capper station (see block diagram) with a screw cap with septum. The tube was placed by the robot 1 in the stirrer block kept at 110° C. The robot 2 pipetted in the following reagents in succession:

1.) 0.5 ml of a solution containing methanesulfonic acid and pyrazolesulfonic acid amide, in each case 0.2 M, in acetonitrile 2.) 0.5 ml of a 1.0 M amine solution in acetonitrile.

The reaction mixture was stirred for 45 hours at 110° C. in one of the stirrer blocks. The reaction solution was then filtered out at the filtration station. The test tube was then rinsed twice, once with 1.5 ml of dichloromethane and once with 1.5 ml of water.

The rack with the samples was placed manually on the working-up station. The reaction mixture was shaken for 30 minutes. The reaction mixture was briefly centrifuged in a centrifuge to form the phase boundary. The phase boundary was optically detected and the organic phase was pipetted off. In the next stage a further 1.5 ml of dichloromethane was added to the aqueous phase, which was shaken, centrifuged, and the organic phase was pipetted off. The combined organic phases were dried over 2.4 g of MgSO$_4$ (granulated). The solvent was removed in a vacuum centrifuge. Each sample was analysed by ESI-MS and/or NMR.

The automated synthesis procedure ensures the identical treatment of all samples as well as balanced constant reaction conditions.

Example 1

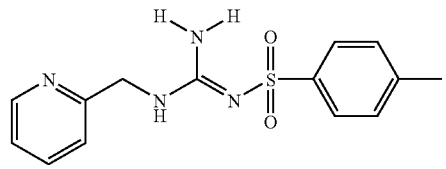

N-{amino-[pyridin-2-yl-methyl)-amino]-methylene}-4-methylbenzenesulfonamide (1)

The compound of Example I was prepared according to the accompanying synthesis procedure from 0.5 ml of N-[(3,5-dimethylpyrazol-1-yl)-iminomethyl]-4-methylbenzene-sulfonamide solution (0.2 M, acetonitrile) with 19 mg of methanesulfonic acid and 0.5 ml of 2-picolylamine solution (1.0

M, acetonitrile) and filed in a substance databank. Calculated mol. wt. 304.37; found mol. wt. (M+H) 305.2; 609.0 (Dimer)

Example 2

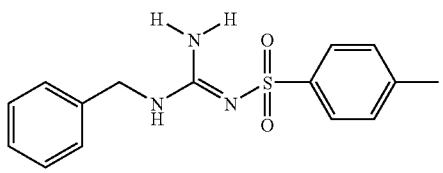

N-[amino-(benzylaminomethylene)]-4-methylbenzene-sulfonamide (2)

The compound of Example 2 was prepared according to the accompanying synthesis procedure from 0.5 ml of N-[(3,5-dimethylpyrazol-1-yl)-iminomethyl]-4-methylbenzene-sulfonamide solution (0.2 M, acetonitrile) with 19 mg of methanesulfonic acid and 0.5 ml of 2-benzylamine solution (1.0 M, acetonitrile) and filed in a substance databank. Calculated mol. wt. 303.38; found mol. wt. (M+H) 304.4; 607.9 (Dimer)

Example 3

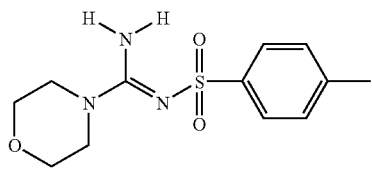

N-(aminomorpholin-4-yl-methylene)-4-methylbenzene-sulfonamide (3)

The compound of Example 3 was prepared according to the accompanying synthesis procedure from 0.5 ml of N-[(3,5-dimethylpyrazol-1-yl)-iminomethyl]-4-methylbenzene-sulfonamide solution (0.2 M, acetonitrile) with 19 mg of methanesulfonic acid and 0.5 ml of morpholine solution (1.0 M, acetonitrile) and filed in a substance databank. Calculated mol. wt. 283.35; found mol. wt. (M+H) 284.1

Example 4

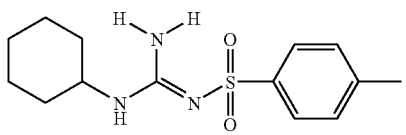

N-(aminocyclohexylaminomethylene)-4-methylbenzene-sulfonamide (4)

The compound of Example 4 was prepared according to the accompanying synthesis procedure from 0.5 ml of N-[(3,5-dimethylpyrazol-1-yl)-iminomethyl]-4-methylbenzene-sulfonamide solution (0.2 M, acetonitrile) with 19 mg of methanesulfonic acid and 0.5 ml of cyclohexylamine solution (1.0 M, acetonitrile) and filed in a substance databank. Calculated mol. wt. 295.40; found mol. wt. (M+H) 296.1; 591.5 (Dimer)

Example 5

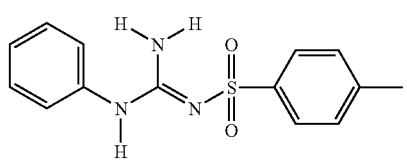

N-(aminophenylaminomethylene)-4-methylbenzene-sulfonamide (5)

The compound of Example 5 was prepared according to the accompanying synthesis procedure from 0.5 ml of N-[(3,5-dimethylpyrazol-1-yl)-iminomethyl]-4-methylbenzene-sulfonamide solution (0.2 M, acetonitrile) with 19 mg of methanesulfonic acid and 0.5 ml of aniline solution (1.0 M, acetonitrile) and filed in a substance databank. Calculated mol. wt. 289.35; found mol. wt. (M+H) 290.2; 579.0 (Dimer)

Example 6

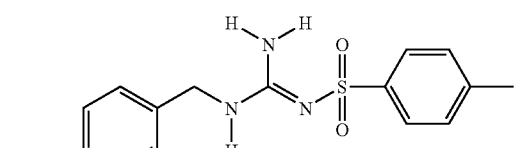

N-[(amino-4-methoxybenzylamino)-methylene]-4-methylbenzene-sulfonamide (6)

The compound of Example 6 was prepared according to the accompanying synthesis procedure from 0.5 ml of N-[(3,5-dimethylpyrazol-1-yl)-iminomethyl]-4-methylbenzene-sulfonamide solution (0.2 M, acetonitrile) with 19 mg of methanesulfonic acid and 0.5 ml of 4-methoxybenzylamine solution (1.0 M, acetonitrile) and filed in a substance databank. Calculated mol. wt. 333.41; found mol. wt. (M+H) 334.2; 667.0 (Dimer)

Example 7

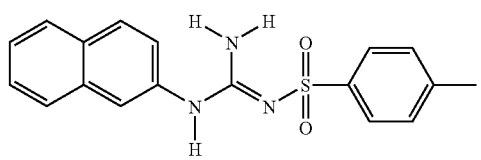

N-[amino-(naphthalin-2-yl-amino)-methylene]-4-methylbenzenesulfonamide (7)

The compound of Example 7 was prepared according to the accompanying synthesis procedure from 0.5 ml of N-[(3,5-dimethylpyrazol-1-yl)-iminomethyl]-4-methylbenzene-sulfonamide solution (0.2 M, acetonitrile) with 19 mg of methanesulfonic acid and 0.5 ml of 2-naphthylamine solution (1.0 M, acetonitrile) and filed in a substance databank. Calculated mol. wt. 339.41; found mol. wt. (M+H) 340.3; 679.1 (Dimer)

Example 8

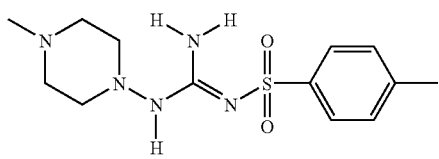

N-[amino-(4-methylpiperazin-1-yl-amino)-methylene]-4-methylbenzenesulfonamide (8)

The compound of Example 8 was prepared according to the accompanying synthesis procedure from 0.5 ml of N-[(3,5-dimethylpyrazol-1-yl)-iminomethyl]-4-methylbenzene-sulfonamide solution (0.2 M, acetonitrile) with 19 mg of methanesulfonic acid and 0.5 ml of N-amino-4-methylpiperazine solution (1.0 M, acetonitrile) and filed in a substance databank. Calculated mol. wt. 311.40; found mol. wt. (M+H) 312.2; 623.0 (Dimer)

Example 9

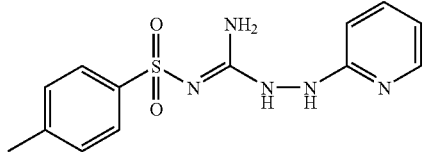

N-[amino-(N'-pyridin-2-yl-hydrazino)-methylene]-4-methylbenzenesulfonamide (9)

The compound of Example 9 was prepared according to the accompanying synthesis procedure from 0.5 ml of N-[(3,5-dimethylpyrazol-1-yl)-iminomethyl]-4-methylbenzene-sulfonamide solution (0.2 M, acetonitrile) with 19 mg of methanesulfonic acid and 0.5 ml of 2-hydrazinopyridine solution (1.0 M, acetonitrile) and filed in a substance databank. Calculated mol. wt. 305.36; found mol. wt. (M+H) 306.1; 621.6 (Dimer)

Example 10

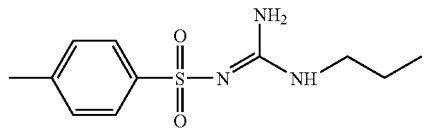

N-[aminopropylaminomethylene]-4-methylbenzenesulfonamide (10)

The compound of Example 10 was prepared according to the accompanying synthesis procedure from 0.5 ml of N-[(3,5-dimethylpyrazol-1-yl)-iminomethyl]-4-methylbenzene-sulfonamide solution (0.2 M, acetonitrile) with 19 mg of methanesulfonic acid and 0.5 ml of n-propylamine solution (1.0 M, acetonitrile) and filed in a substance databank. Calculated mol. wt. 255.34; found mol. wt. (M+H) 256.2; 511.0 (Dimer)

Example 11

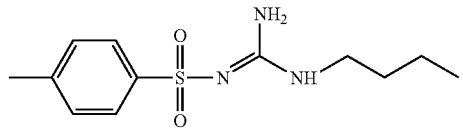

N-(aminobutylaminomethylene)-4-methylbenzenesulfonamide (11)

The compound of Example 11 was prepared according to the accompanying synthesis procedure from 0.5 ml of N-[(3,5-dimethylpyrazol-1-yl)-iminomethyl]-4-methylbenzene-sulfonamide solution (0.2 M, acetonitrile) with 19 mg of methanesulfonic acid and 0.5 ml of n-butylamine solution (1.0 M, acetonitrile) and filed in a substance databank. Calculated mol. wt. 269.36; found mol. wt. (M+H) 270.3; 539.1 (Dimer)

Example 12

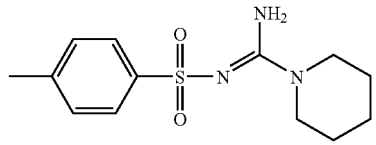

N-[aminobutylaminomethylene]-4-methylbenzenesulfonamide (12)

The compound of Example 12 was prepared according to the accompanying synthesis procedure from 0.5 ml of N-[(3, 5-dimethylpyrazol-1-yl)-iminomethyl]-4-methylbenzene-sulfonamide solution (0.2 M, acetonitrile) with 19 mg of methanesulfonic acid and 0.5 ml of piperidine solution (1.0 M, acetonitrile) and filed in a substance databank. Calculated mol. wt. 281.37; found mol. wt. (M+H) 282.2; 562.9 (Dimer)

Example 13

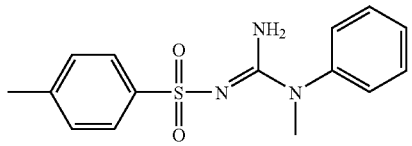

N-[aminobutylaminomethylene]-4-methylbenzene-sulfonamide (13)

The compound of Example 13 was prepared according to the accompanying synthesis procedure from 0.5 ml of N-[(3,5-dimethylpyrazol-1-yl)-iminomethyl]-4-methylbenzene-sulfonamide solution (0.2 M, acetonitrile) with 19 mg of methanesulfonic acid and 0.5 ml of N-methylaniline solution (1.0 M, acetonitrile) and filed in a substance databank. Calculated mol. wt. 303.38; found mol. wt. (M+H) 304.2

Example 14

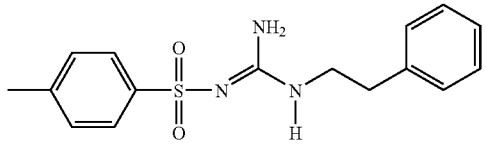

N-[aminophenethylaminomethylene]-4-methylben-zene-sulfonamide (14)

The compound of Example 14 was prepared according to the accompanying synthesis procedure from 0.5 ml of N-[(3,5-dimethylpyrazol-1-yl)-iminomethyl]-4-methylbenzene-sulfonamide solution (0.2 M, acetonitrile) with 19 mg of methanesulfonic acid and 0.5 ml of phenethylamine solution (1.0 M, acetonitrile) and filed in a substance databank. Calculated mol. wt. 317.41; found mol. wt. (M+H) 318.3; 635.1 (Dimer)

Example 15

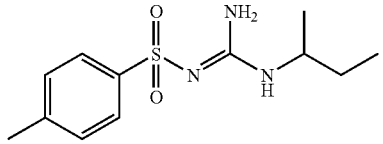

N-[amino-sec-butylaminomethylene]-4-methylben-zene-sulfonamide (15)

The compound of Example 15 was prepared according to the accompanying synthesis procedure from 0.5 ml of N-[(3,5-dimethylpyrazol-1-yl)-iminomethyl]-4-methylbenzene-sulfonamide solution (0.2 M, acetonitrile) with 19 mg of methanesulfonic acid and 0.5 ml of s-butylamine solution (1.0 M, acetonitrile) and filed in a substance databank. Calculated mol. wt. 269.36; found mol. wt. (M+H) 270.2; 539.1 (Dimer)

Example 16

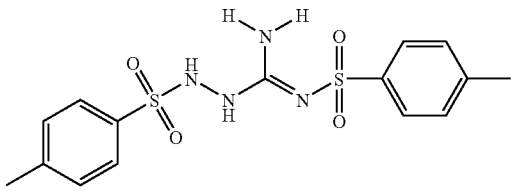

N-[amino-(N'-tosyl-2-yl-hydrazino)-4-methylben-zene-sulfonamide (16)

The compound of Example 16 was prepared according to the accompanying synthesis procedure from 0.5 ml of N-[(3,5-dimethylpyrazol-1-yl)-iminomethyl]-4-methylbenzene-sulfonamide solution (0.2 M, acetonitrile) with 19 mg of methanesulfonic acid and 0.5 ml of tosylhydrazide solution (1.0 M, acetonitrile) and filed in a substance databank. Calculated mol. wt. 382.46; found mol. wt. (M+H) 383.2; 764.9 (Dimer)

Example 17

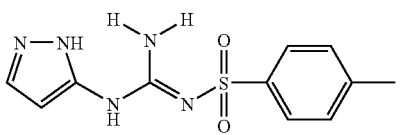

N-[amino-(2H-pyrazol-3-yl-amino)-methylene]-4-methylbenzenesulfonamide (17)

The compound of Example 17 was prepared according to the accompanying synthesis procedure from 0.5 ml of N-[(3,5-dimethylpyrazol-1-yl)-iminomethyl]-4-methylbenzene-sulfonamide solution (0.2 M, acetonitrile) with 19 mg of methanesulfonic acid and 0.5 ml of 2-aminopyrazole solution (1.0 M, acetonitrile) and filed in a substance databank. Calculated mol. wt. 279.32; found mol. wt. (M+H) 280.3; 559.0 (Dimer)

Example 18

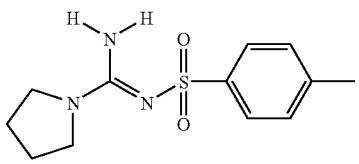

N-(aminopyrrolidin-1-yl-methylene)-4-methylben-zene-sulfonamide (18)

The compound of Example 18 was prepared according to the accompanying synthesis procedure from 0.5 ml of N-[(3,5-dimethylpyrazol-1-yl)-iminomethyl]-4-methylbenzene-sulfonamide solution (0.2 M, acetonitrile) with 19 mg of methanesulfonic acid and 0.5 ml of pyrrolidine solution (1.0

M, acetonitrile) and filed in a substance databank. Calculated mol. wt. 267.35; found mol. wt. (M+H) 268.2; 534.9 (Dimer)

Example 19

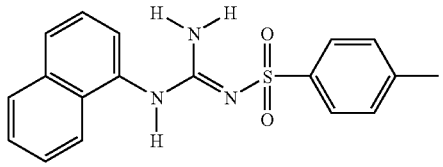

N-[amino-(naphthalin-1-yl-amino)-methylene]-4-methyl-benzenesulfonamide (19)

The compound of Example 19 was prepared according to the accompanying synthesis procedure from 0.5 ml of N-[(3,5-dimethylpyrazol-1-yl)-iminomethyl]-4-methylbenzenesulfonamide solution (0.2 M, acetonitrile) with 19 mg of methanesulfonic acid and 0.5 ml of 1-naphthylamine solution (1.0 M, acetonitrile) and filed in a substance databank. Calculated mol. wt. 339.41; found mol. wt. (M+H) 340.3; 679.1 (Dimer)

Example 20

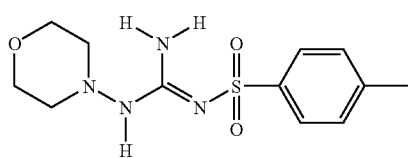

N-[amino-(morpholin-4-yl-amino)-methylene]-4-methyl-benzenesulfonamide (20)

The compound of Example 20 was prepared according to the accompanying synthesis procedure from 0.5 ml of N-[(3,5-dimethylpyrazol-1-yl)-iminomethyl]-4-methylbenzenesulfonamide solution (0.2 M, acetonitrile) with 19 mg of methanesulfonic acid and 0.5 ml of N-aminomorpholine solution (1.0 M, acetonitrile) and filed in a substance databank. Calculated mol. wt. 298.11; found mol. wt. (M+H) 299.3; 597.1 (Dimer)

Example 21

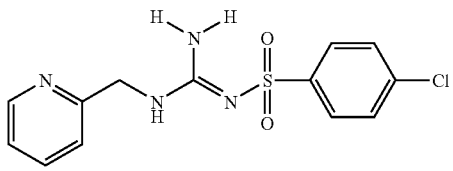

N-{amino-[(pyridin-2-yl-methyl)-amino]-methylene}-4-chlorobenzenesulfonamide (21)

The compound of Example 21 was prepared according to the accompanying synthesis procedure from 0.5 ml of N-[(3,5-dimethylpyrazol-1-yl)-iminomethyl]-4-chlorobenzenesulfonamide solution (0.2 M, acetonitrile) with 19 mg of methanesulfonic acid and 0.5 ml of 2-picolylamine solution (1.0 M, acetonitrile) and filed in a substance databank. Calculated mol. wt. 327.79; found mol. wt. (M+H) 328.3; 655.6 (Dimer)

Example 22

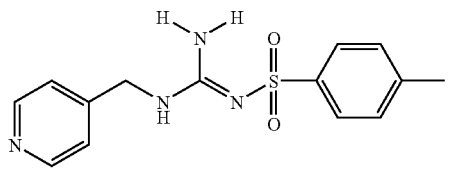

N-{amino-[(pyridin-4-yl-methyl)-amino]-methylene}-4-methylbenzenesulfonamide (22)

The compound of Example 22 was prepared according to the accompanying synthesis procedure from 0.5 ml of N-[(3,5-dimethylpyrazol-1-yl)-iminomethyl]-4-chlorobenzenesulfonamide solution (0.2 M, acetonitrile) with 19 mg of methanesulfonic acid and 0.5 ml of 4-picolylamine solution (1.0 M, acetonitrile) and filed in a substance databank. Calculated mol. wt. 304.37; found mol. wt. (M+H) 305.2; 609.1 (Dimer)

Example 23

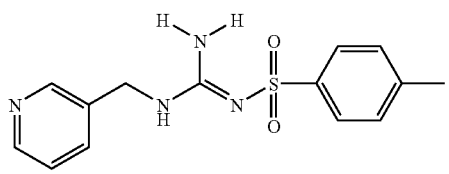

N-{amino-[(pyridin-3-yl-methyl)-amino]-methylene}-4-methylbenzenesulfonamide (23)

The compound of Example 23 was prepared according to the accompanying synthesis procedure from 0.5 ml of N-[(3,5-dimethylpyrazol-1-yl)-iminomethyl]-4-chlorobenzenesulfonamide solution (0.2 M, acetonitrile) with 19 mg of methanesulfonic acid and 0.5 ml of 3-picolylamine solution Example 24

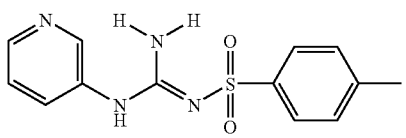

N-[amino-(pyridin-3-yl-amino)-methylene]-4-methyl-benzenesulfonamide (24)

The compound of Example 24 was prepared according to the accompanying synthesis procedure from 0.5 ml of N-[(3,5-dimethylpyrazol-1-yl)-iminomethyl]-4-methylbenzene-sulfonamide solution (0.2 M, acetonitrile) with 19 mg of methanesulfonic acid and 0.5 ml of 3-aminopyridine solution (1.0 M, acetonitrile) and filed in a substance databank. Calculated mol. wt. 290.34; found mol. wt. (M+H) 291.1; 580.9 (Dimer)

Example 25

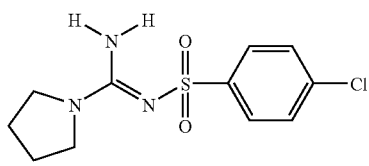

N-(aminopyrrolidin-1-yl-methylene)-4-chlorobenzene-sulfonamide (25)

The compound of Example 25 was prepared according to the accompanying synthesis procedure from 0.5 ml of N-[(3,5-dimethylpyrazol-1-yl)-iminomethyl]-4-chlorobenzene-sulfonamide solution (0.2 M, acetonitrile) with 19 mg of methanesulfonic acid and 0.5 ml of pyrrolidine solution (1.0 M, acetonitrile) and filed in a substance databank. Calculated mol. wt. 287.77; found mol. wt. (M+H) 288.3; 574.8 (Dimer)

Example 26

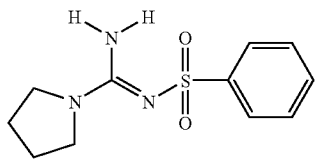

N-(aminopyrrolidin-1-yl-methylene)-benzene-sulfonamide (26)

The compound of Example 26 was prepared according to the accompanying synthesis procedure from 0.5 ml of N-[(3,5-dimethylpyrazol-1-yl)-iminomethyl]-benzenesulfonamide solution (0.2 M, acetonitrile) with 19 mg of methanesulfonic acid and 0.5 ml of pyrrolidine solution (1.0 M, acetonitrile) and filed in a substance databank. Calculated mol. wt. 253.32; found mol. wt. (M+H) 254.3; 506.9 (Dimer)

Example 27

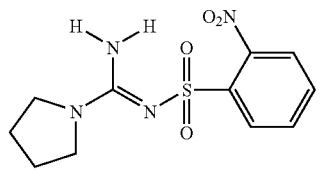

N-(aminopyrrolidin-1-yl-methylene)-2-nitrobenzene-sulfonamide (27)

The compound of Example 27 was prepared according to the accompanying synthesis procedure from 0.5 ml of N-[(3,5-dimethylpyrazol-1-yl)-iminomethyl]-2-nitrobenzene-sulfonamide solution (0.2 M, acetonitrile) with 19 mg of methanesulfonic acid and 0.5 ml of pyrrolidine solution (1.0 M, acetonitrile) and filed in a substance databank. Calculated mol. wt. 298.32; found mol. wt. (M+H) 299.3; 596.8 (Dimer)

Example 28

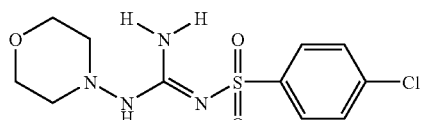

N-[amino-(morpholin-4-yl-amino)-methylene]-4-chlorobenzenesulfonamide (28)

The compound of Example 28 was prepared according to the accompanying synthesis procedure from 0.5 ml of N-[(3,5-dimethylpyrazol-1-yl)-iminomethyl]-4-chlorobenzene-sulfonamide solution (0.2 M, acetonitrile) with 19 mg of methanesulfonic acid and 0.5 ml of N-aminomorpholine solution (1.0 M, acetonitrile) and filed in a substance databank. Calculated mol. wt. 318.78; found mol. wt. (M+H) 319.3; 637.0 (Dimer)

Example 29

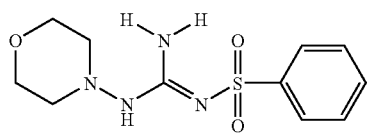

N-[amino-(morpholin-4-yl-amino)-methylene]-benzene-sulfonamide (29)

The compound of Example 29 was prepared according to the accompanying synthesis procedure from 0.5 ml of N-[(3,5-dimethylpyrazol-1-yl)-iminomethyl]-benzenesulfonamide solution (0.2 M, acetonitrile) with 19 mg of methanesulfonic acid and 0.5 ml of N-aminomorpholine solution (1.0 M, acetonitrile) and filed in a substance databank. Calculated mol. wt. 284.34; found mol. wt. (M+H) 285.3; 569.1 (Dimer)

Example 30

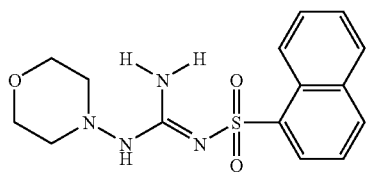

Naphthalene-1-sulfonic acid amino-(morpholin-4-yl-amino)-methylene amide (30)

The compound of Example 30 was prepared according to the accompanying synthesis procedure from 0.5 ml of N-[(3,5-dimethylpyrazol-1-yl)-iminomethyl]-naphthol-1-sulfonamide solution (0.2 M, acetonitrile) with 19 mg of methanesulfonic acid and 0.5 ml of N-aminomorpholine solution (1.0 M, acetonitrile) and filed in a substance databank. Calculated mol. wt. 334.39; found mol. wt. (M+H) 335.3; 669.1 (Dimer)

Examples 31 to 63

The compounds of Examples 31 to 63 were prepared according to variants of the synthesis processes already described in the foregoing general process and examples.

Example 31

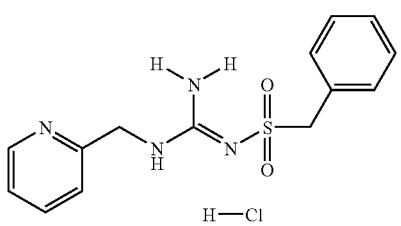

Example 31

N-{amino-[(pyridin-2-yl-methyl)-amino]-methylene}-C-phenylmethanesulfonamide; hydrochloride (31)

Example 32

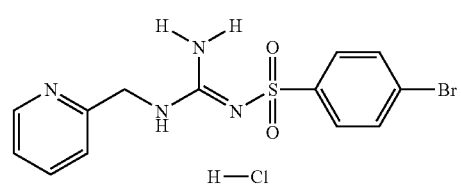

Example 32

N-{amino[(pyridin-2-yl-methyl)-amino]-methylene}-4-bromobenzenesulfonamide; hydrochloride (32)

Example 33

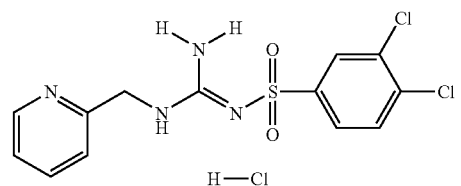

Example 33

N-{amino[(pyridin-2-yl-methyl)-amino]-methylene}-3,4-dichlorobenzenesulfonamide; hydrochloride (33)

Example 34

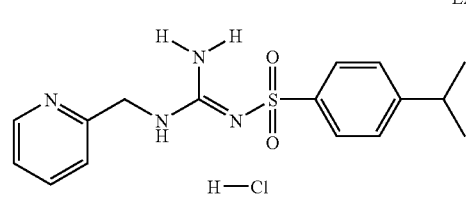

Example 34

37

N-{amino[(pyridin-2-yl-methyl)-amino]-methylene}-4-isopropylbenzenesulfonamide; hydrochloride (34)

Example 35

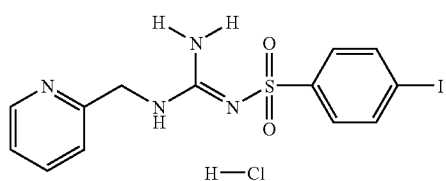
Example 35

N-{amino[(pyridin-2-yl-methyl)-amino]-methylene}-4-iodobenzenesulfonamide; hydrochloride (35)

Example 36

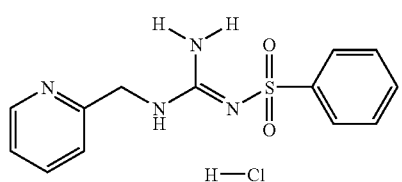
Example 36

N-{amino[(pyridin-2-yl-methyl)-amino]-methylene}-benzenesulfonamide; hydrochloride (36)

Example 37

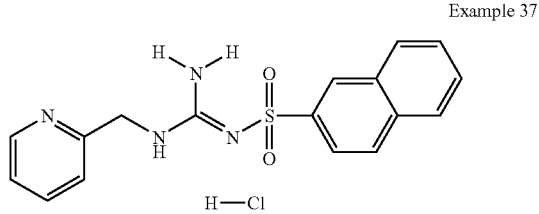
Example 37

Naphthalene-2-sulfonic acid amino-[(pyridin-2-yl-methyl)-amino]-methylene amide; hydrochloride (37)

Example 38

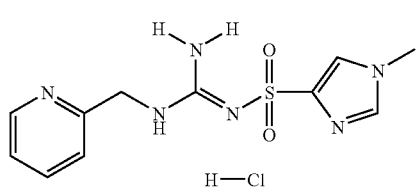
Example 38

38

1-methyl-1H-imidazole-4-sulfonic acid amino-[(pyridin-2-yl-methyl)-amino]-methylene amide; hydrochloride (38)

Example 39

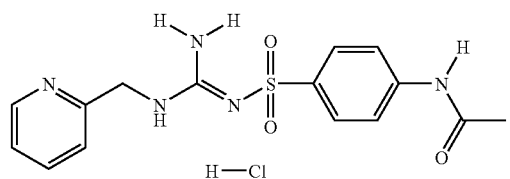
Example 39

N-[4-({amino-[(pyridin-2-yl-methyl)-amino]-methylene}-sulfamoyl)-phenyl]-acetamide; hydrochloride (39)

Example 40

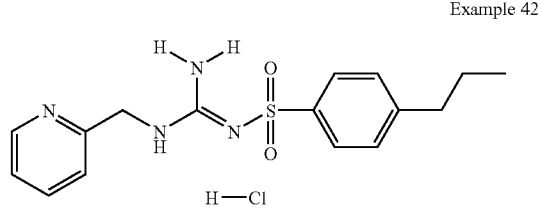
Example 40

N-{amino[(pyridin-2-yl-methyl)-amino]-methylene}-4-fluorobenzenesulfonamide; hydrochloride (40)

Example 41

Example 41

N-{amino[(pyridin-2-yl-methyl)-amino]-methylene}-2,4,6-trimethylbenzenesulfonamide; hydrochloride (41)

Example 42

Example 42

N-{amino[(pyridin-2-yl-methyl)-amino]-methylene}-4-propylbenzenesulfonamide; hydrochloride (42)

Example 43

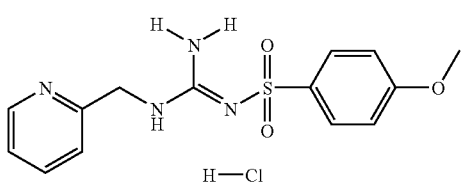

N-{amino[(pyridin-2-yl-methyl)-amino]-methylene}-4-methoxybenzenesulfonamide; hydrochloride (43)

Example 44

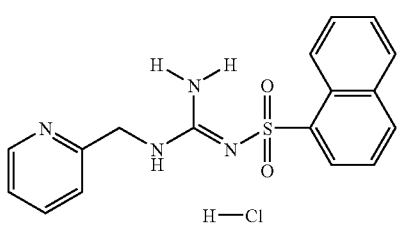

Naphthalene-1-sulfonic acid amino-[(pyridin-2-yl-methyl)-amino]-methylene amide; hydrochloride (44)

Example 45

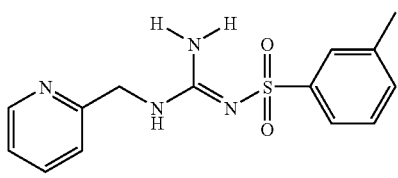

N-{amino[(pyridin-2-yl-methyl)-amino]-methylene}-3-methylbenzenesulfonamide (45)

Example 46

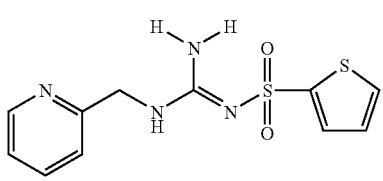

Thiophene-2-sulfonic acid amino-[(pyridin-2-yl-methyl)-amino]-methylene amide (46)

Example 47

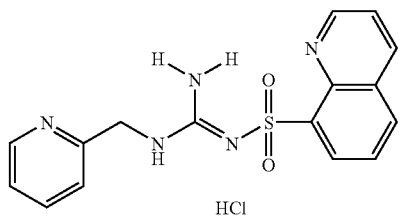

Quinoline-8-sulfonic acid amino-[(pyridin-2-yl-methyl)-amino]-methylene amide (47)

Example 48

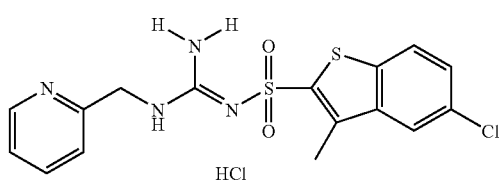

5-chloro-3-methylbenzo[b]thiophene-2-sulfonic acid amino-[(pyridin-2-yl-methyl)-amino]-methylene amide (48)

Example 49

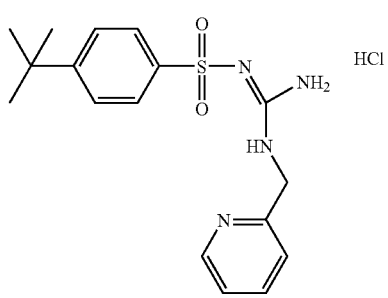

N-{amino[(pyridin-2-yl-methyl)-amino]-methylene}-4-tert.-butylbenzenesulfonamide; hydrochloride (49)

Example 50

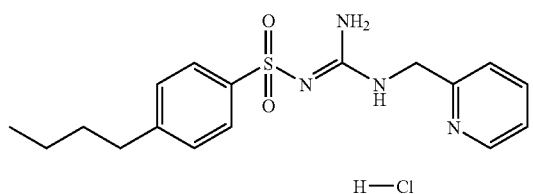

41

N-{amino[(pyridin-2-yl-methyl)-amino]-methyl-ene}-4-butylbenzenesulfonamide; hydrochloride (50)

Example 51

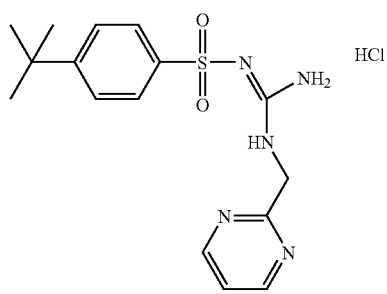

Example 51

N-{amino[pyrimidin-2-yl-methyl)-amino]-methyl-ene}-4-tert.-butylbenzenesulfonamide; hydrochloride (51)

Example 52

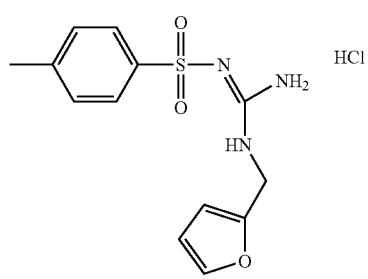

Example 52

N-{amino[(furan-2-yl-methyl)-amino]-methylene}-4-butylbenzenesulfonamide; hydrochloride (52)

Example 53

42

N-{amino[(furan-2-yl-methyl)-amino]-methylene}-4-methylbenzenesulfonamide; hydrochloride (53)

Example 54

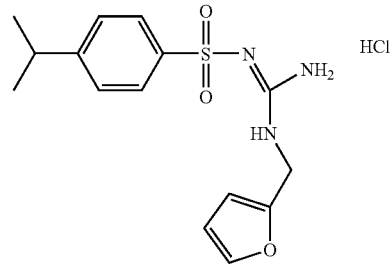

Example 54

N-{amino[(furan-2-yl-methyl)-amino]-methylene}-4-isopropylbenzenesulfonamide; hydrochloride (54)

Example 55

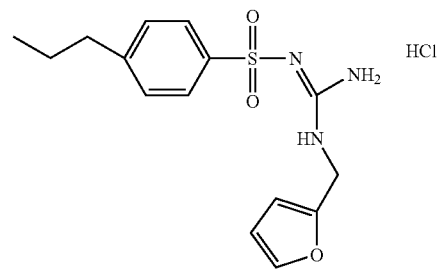

Example 55

N-{amino[(furan-2-yl-methyl)-amino]-methylene}-4-propylbenzenesulfonamide; hydrochloride (55)

Example 56

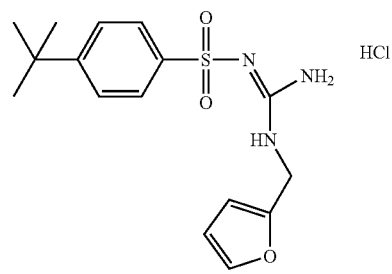

Example 53

Example 56

43

N-{amino[(furan-2-yl-methyl)-amino]-methylene}-4-tert.-butylbenzenesulfonamide; hydrochloride (56)

Example 57

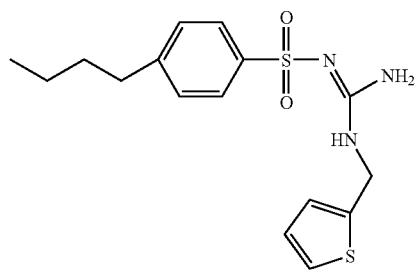

N-{amino[(thiophen-2-yl-methyl)-amino]-methylene}-4-butylbenzenesulfonamide; hydrochloride (57)

Example 58

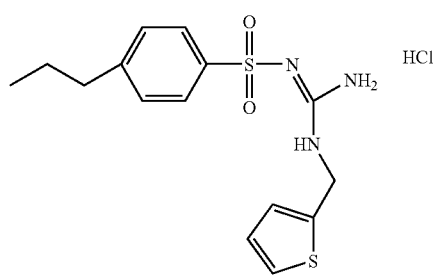

N-{amino[(thiophen-2-yl-methyl)-amino]-methylene}-4-propylbenzenesulfonamide; hydrochloride (58)

Example 59

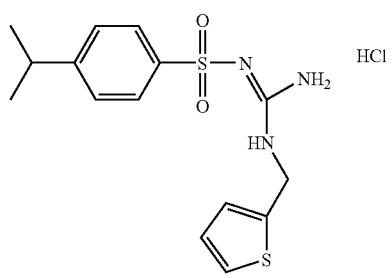

44

N-{amino[(thiophen-2-yl-methyl)-amino]-methylene}-4-isopropylbenzenesulfonamide; hydrochloride (59)

Example 60

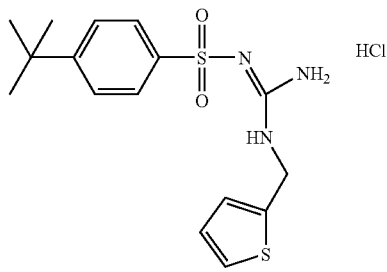

N-{amino[(thiophen-2-yl-methyl)-amino]-methylene}-4-tert.-butylbenzenesulfonamide; hydrochloride (60)

Example 61

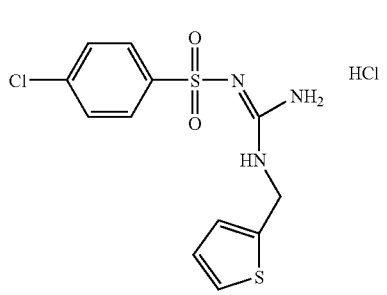

N-{amino[(thiophen-2-yl-methyl)-amino]-methylene}-4-chlorobenzenesulfonamide; hydrochloride (61)

Example 62

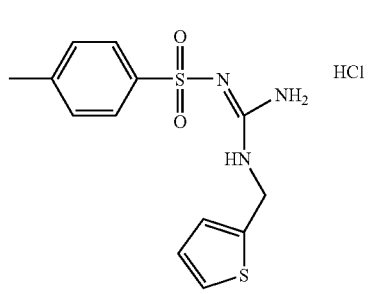

N-{amino[(thiophen-2-yl-methyl)-amino]-methyl-ene}-4-methylbenzenesulfonamide; hydrochloride (62)

Example 63

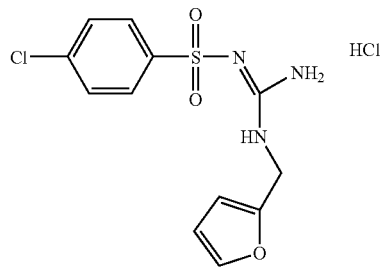

Example 63

N-{amino[(furan-2-yl-methyl)-amino]-methylene}-4-chlorobenzenesulfonamide hydrochloride (63)

Figure 2:
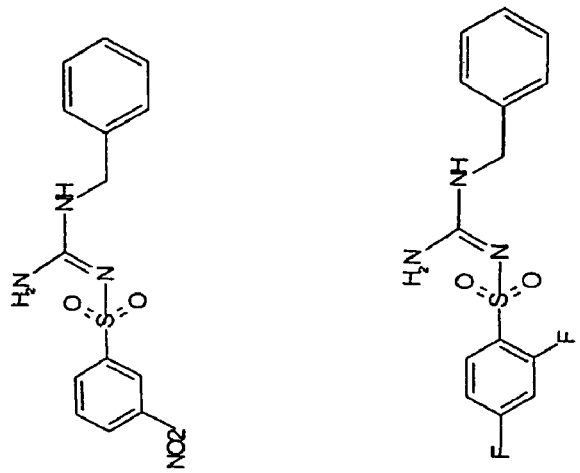
Figure 2:
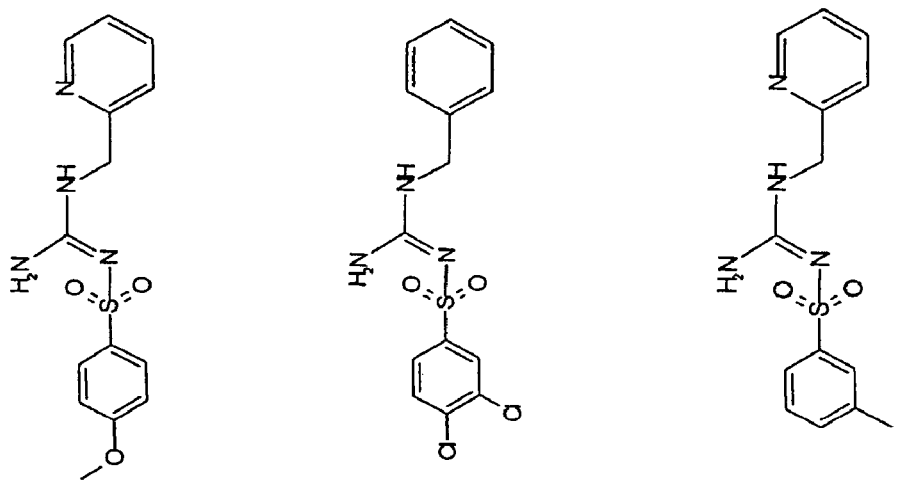
Figure 2:
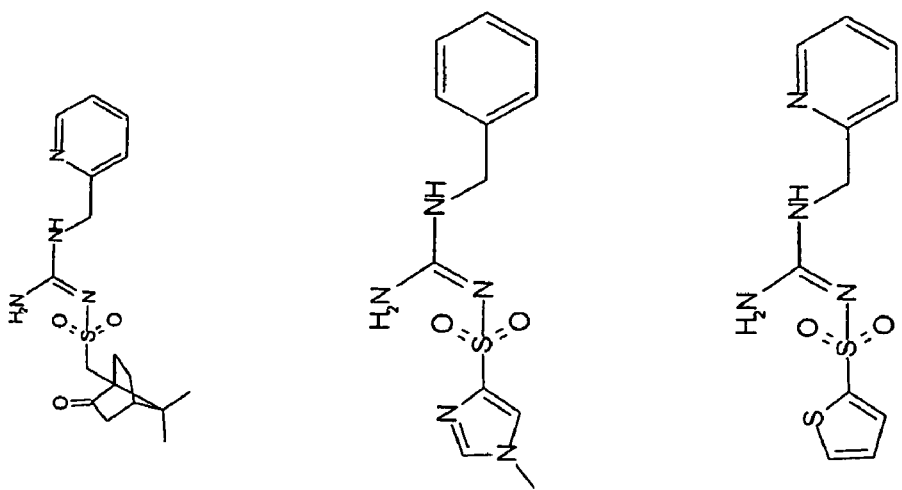
Figure 3:
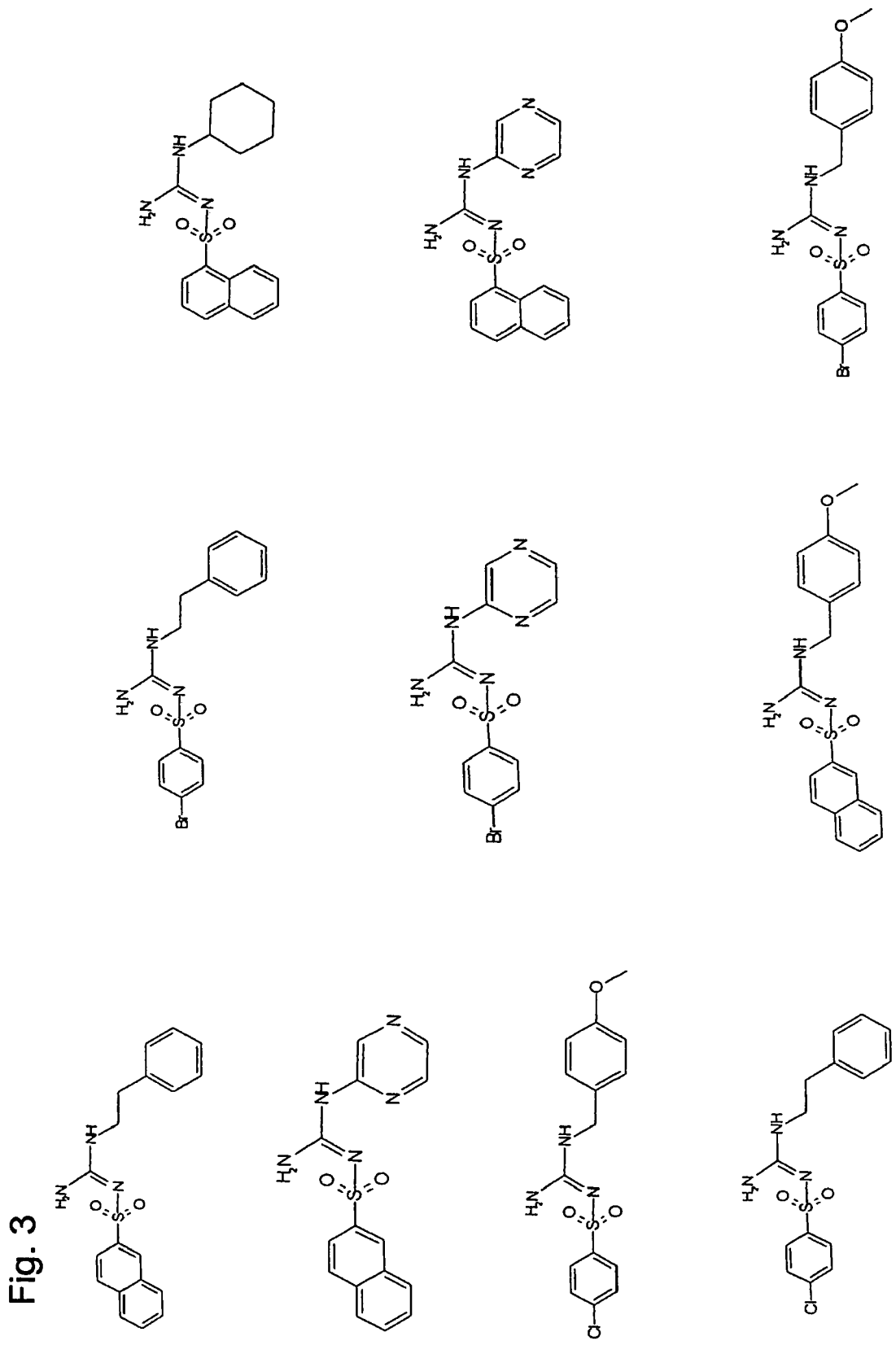
Figure 4:
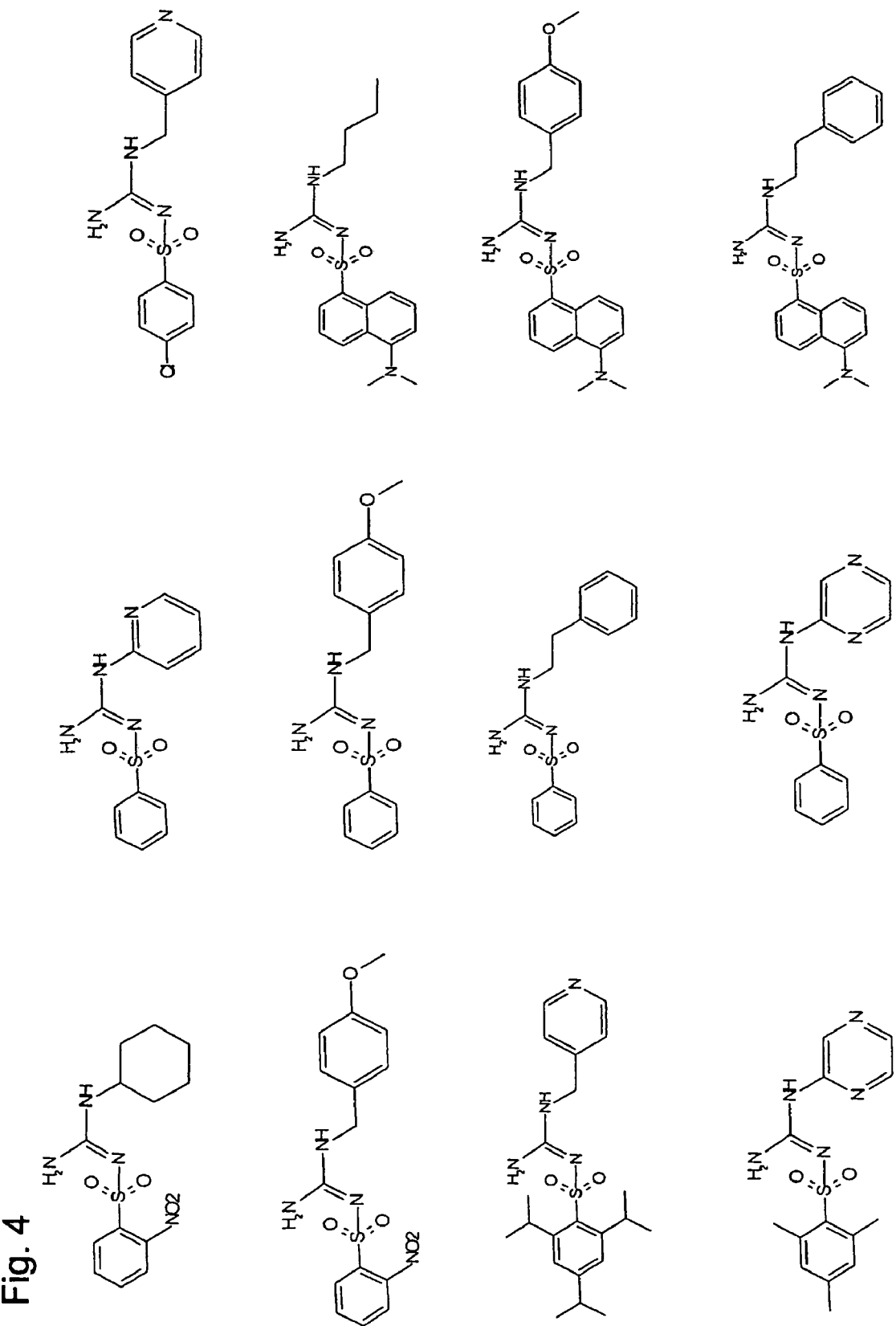
Figure 5:
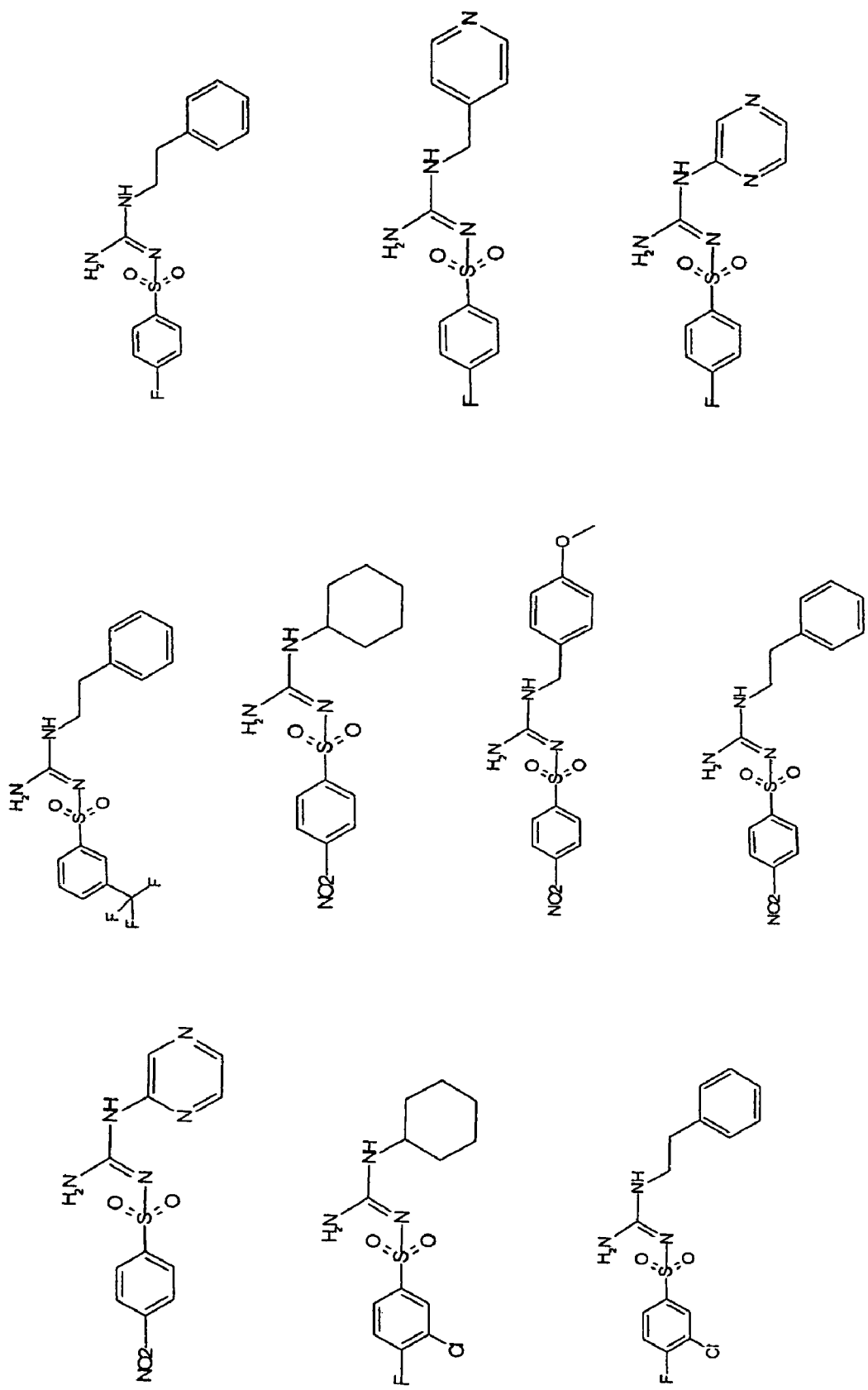
Figure 6:
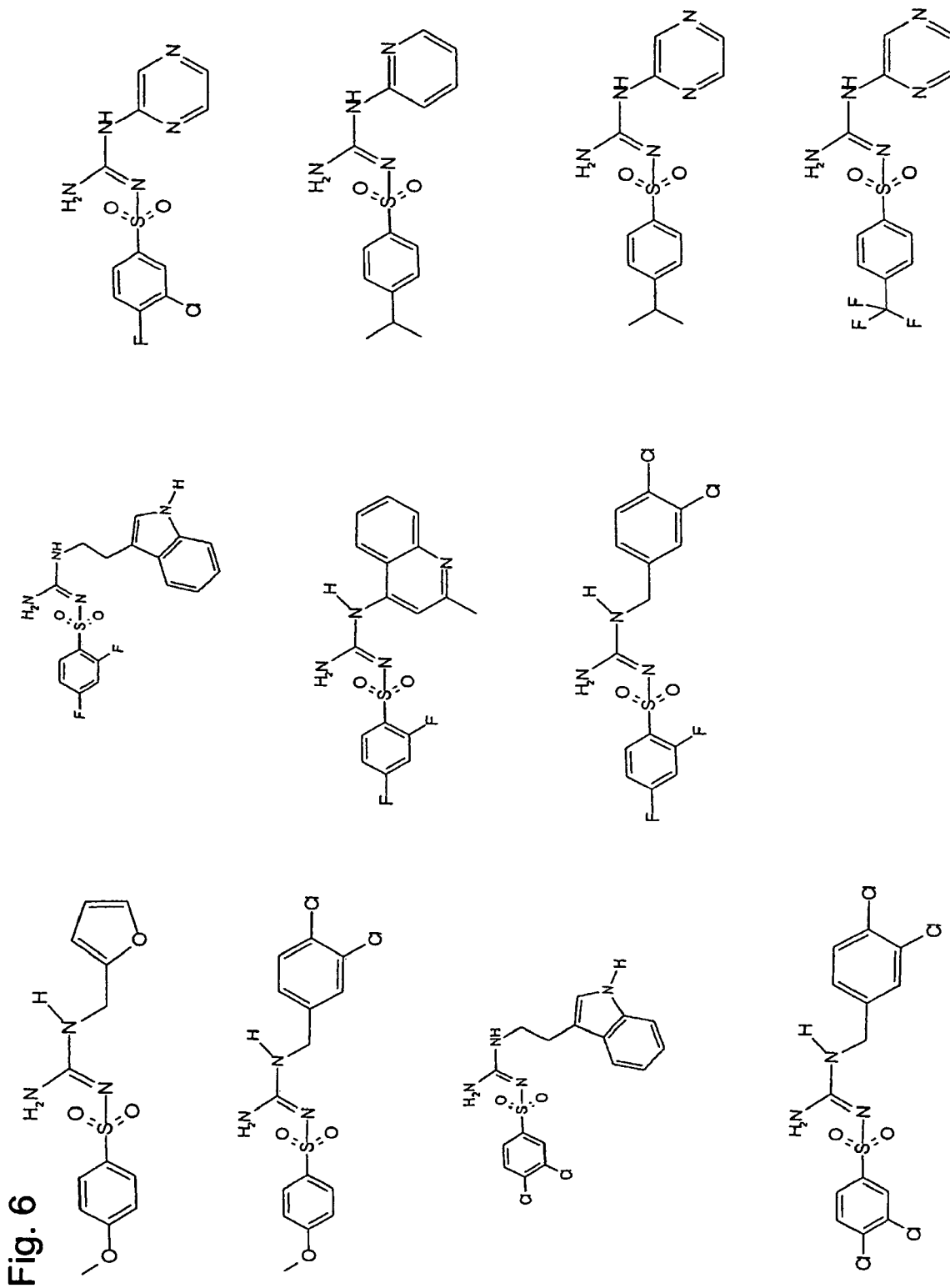
Figure 7:
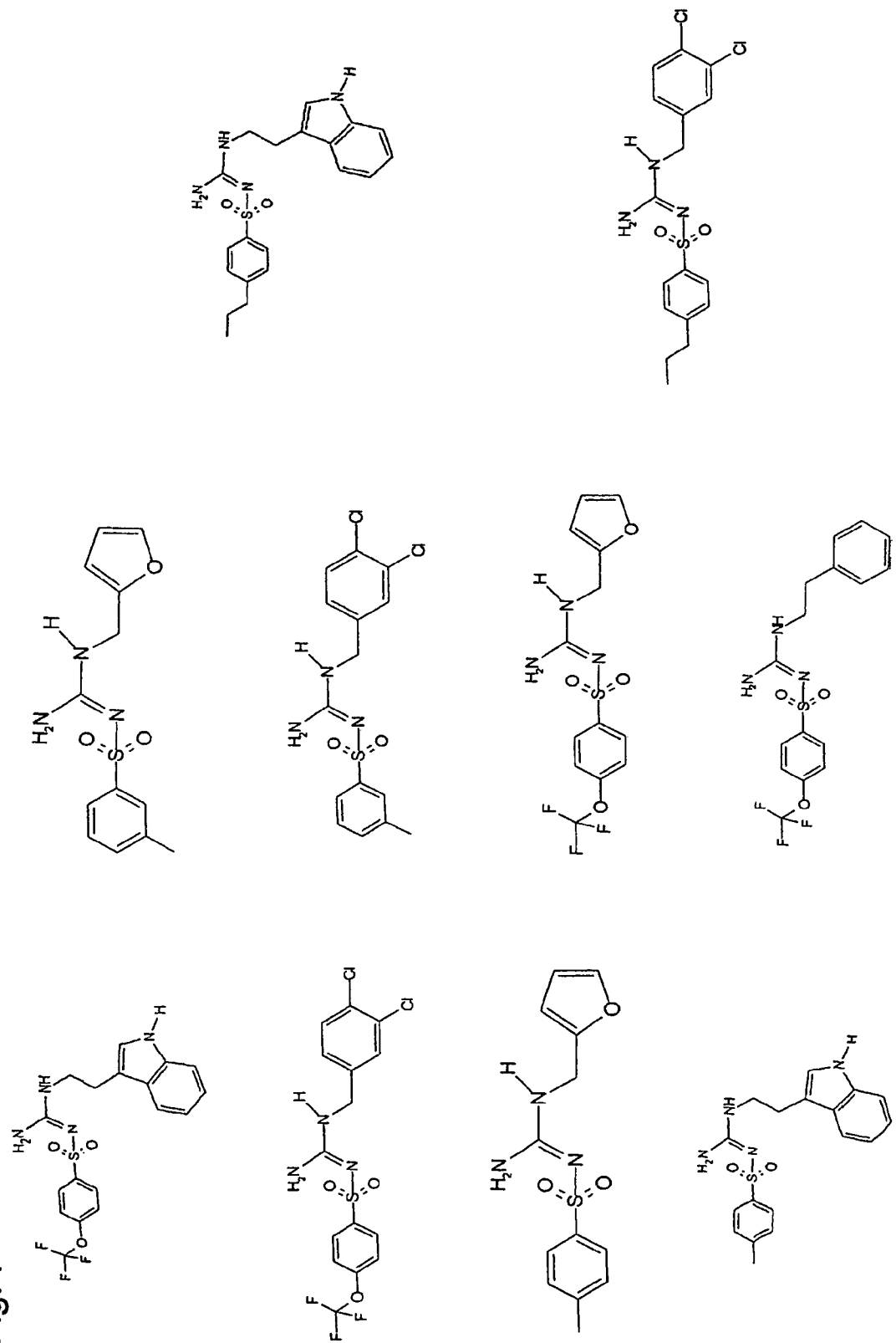
Figure 8:
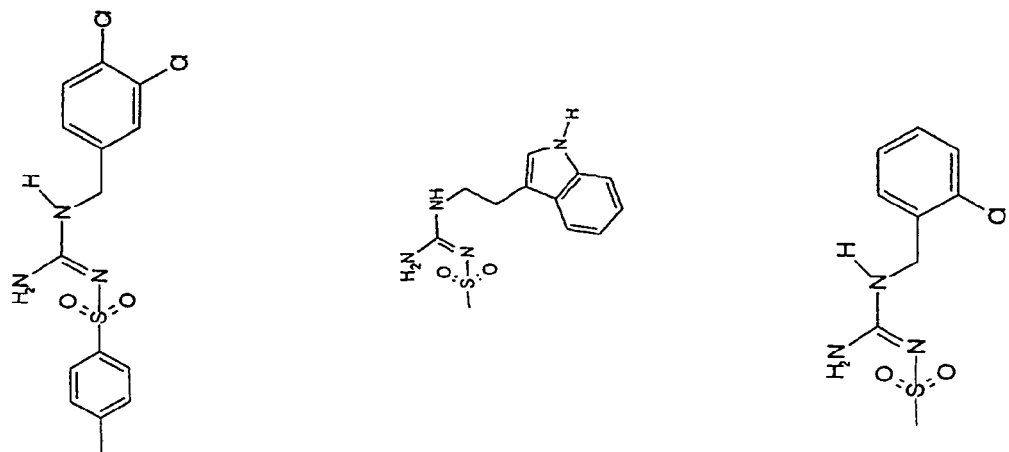
Figure 8:
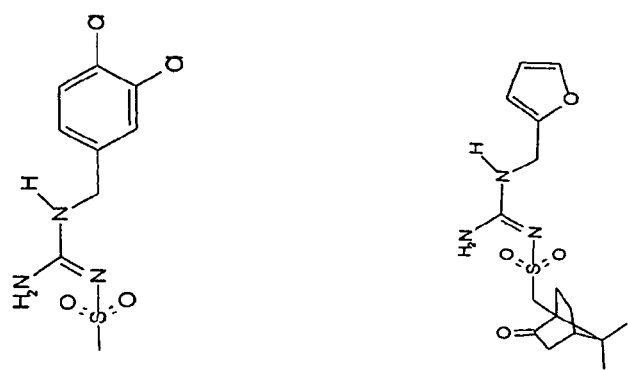
Figure 8:
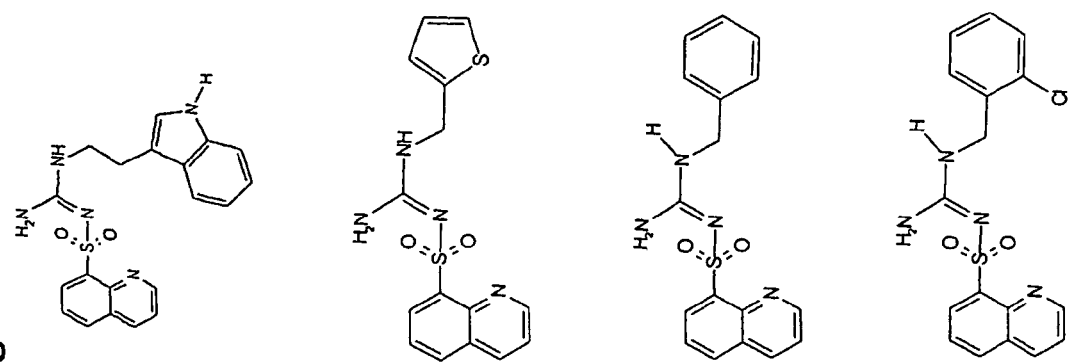
Figure 9:
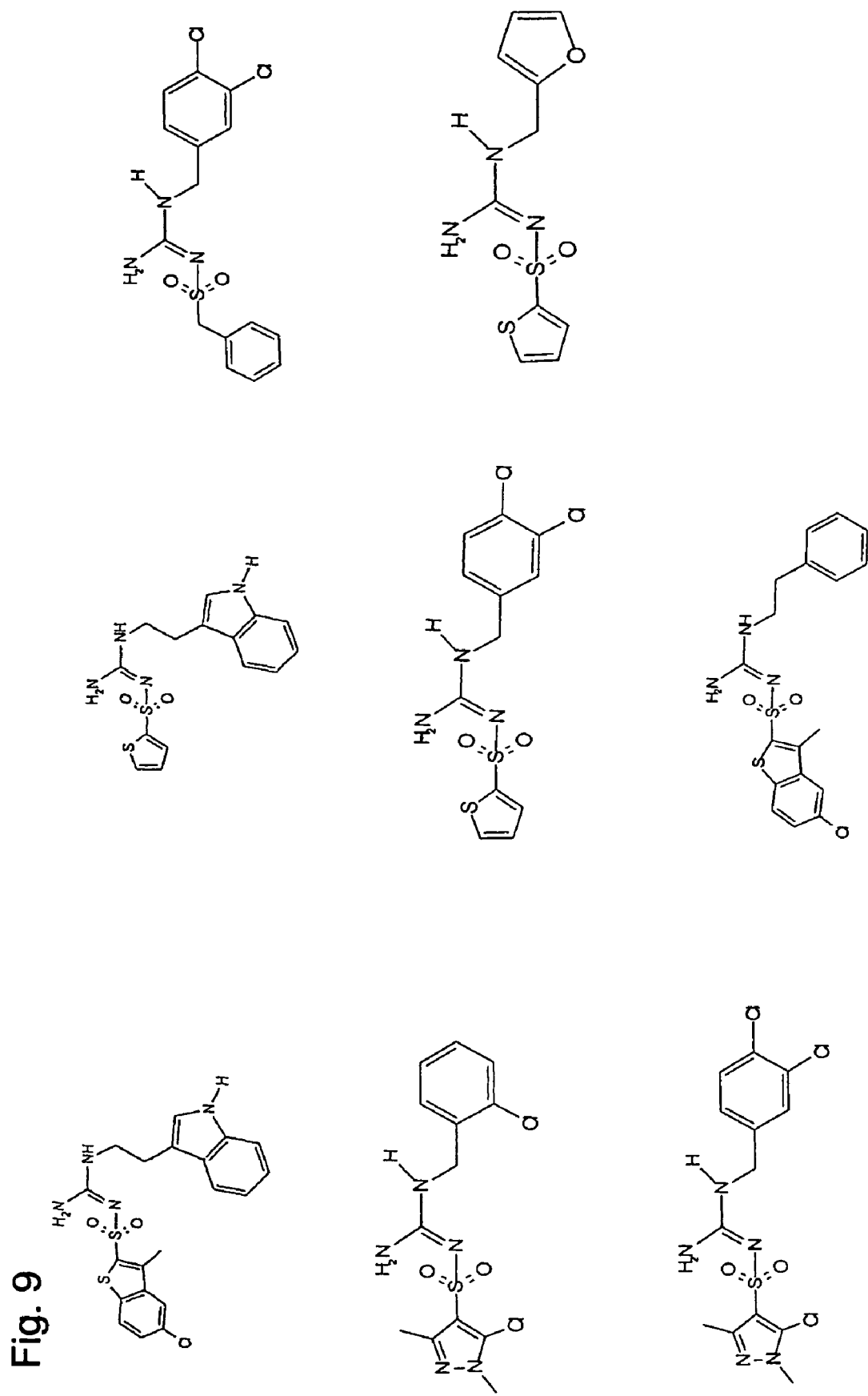
Figure 10:
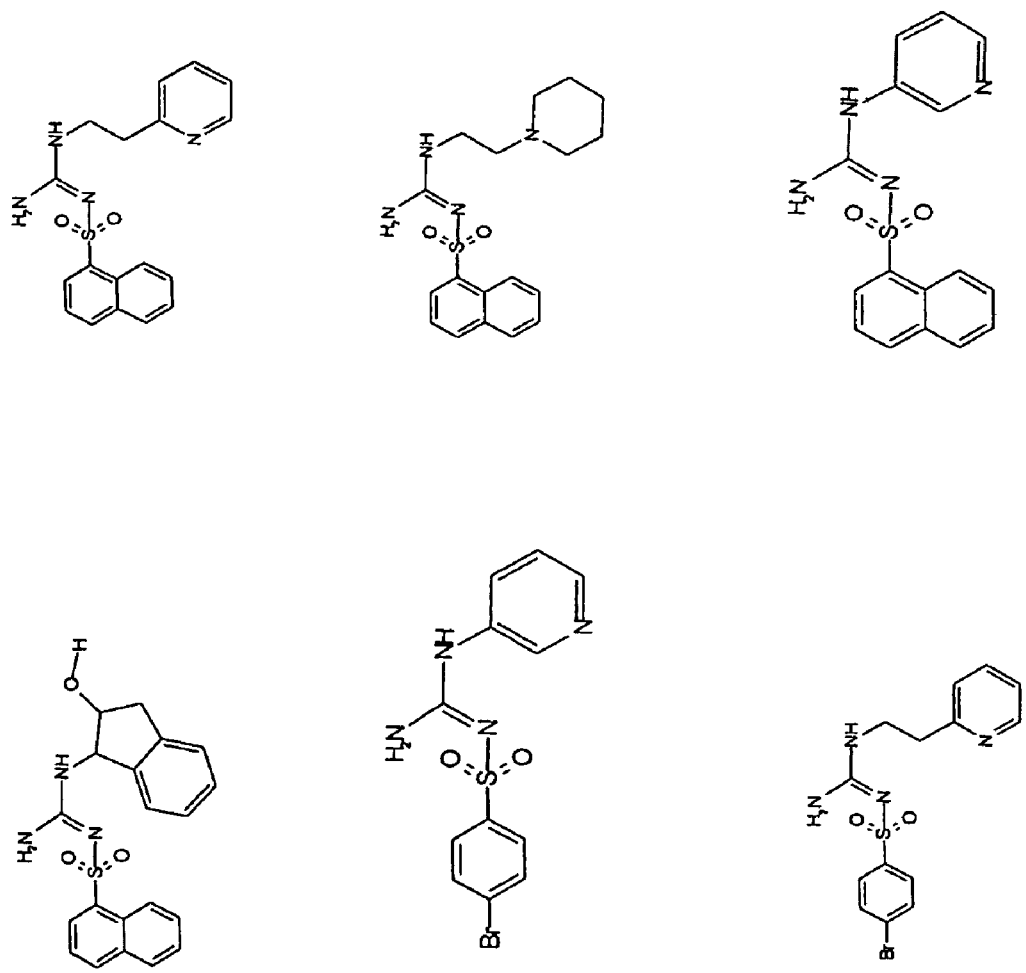
Figure 11:
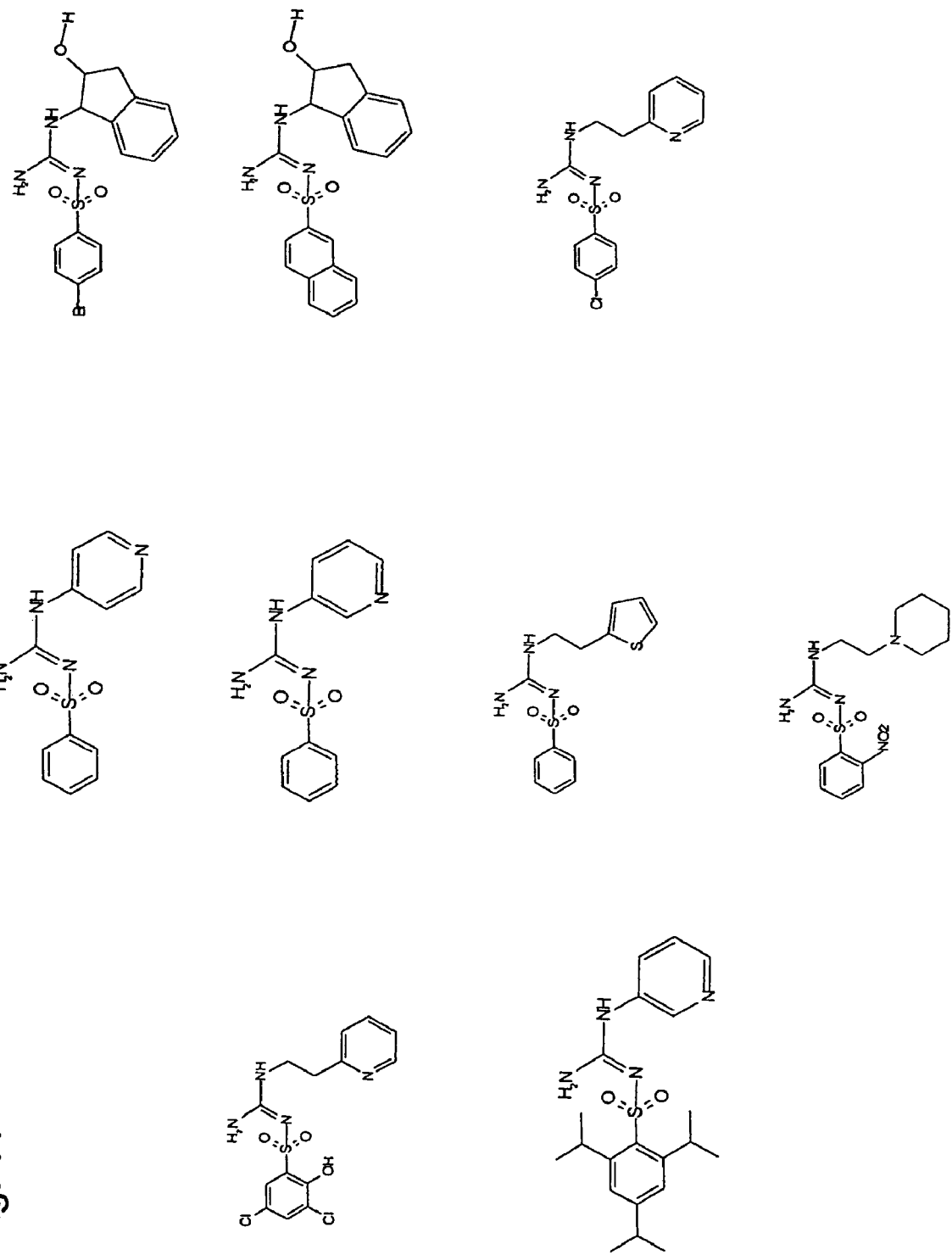
Figure 12:
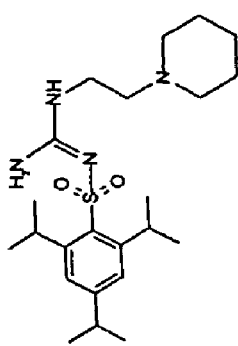
Figure 12:
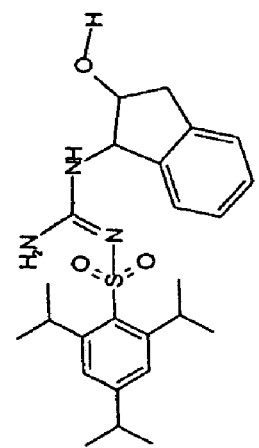
Figure 12:
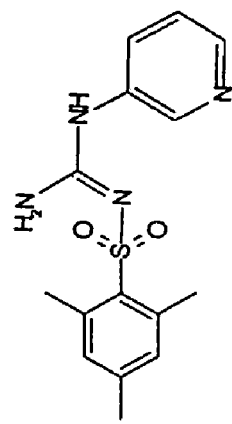
Figure 12:
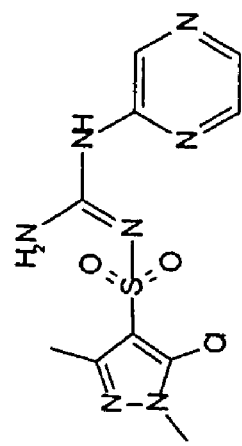
Figure 12:
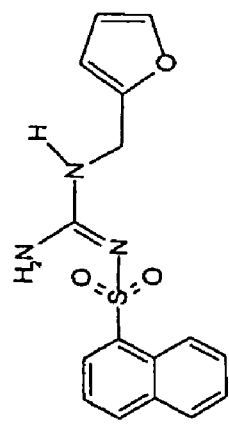
Figure 13:
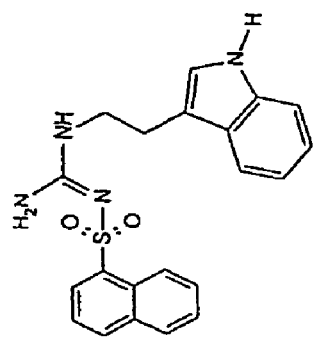
Figure 13:
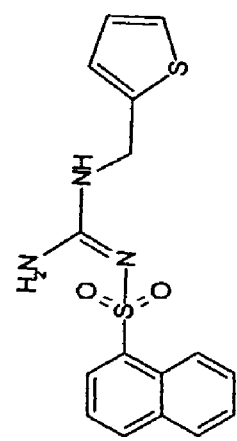
Figure 13:
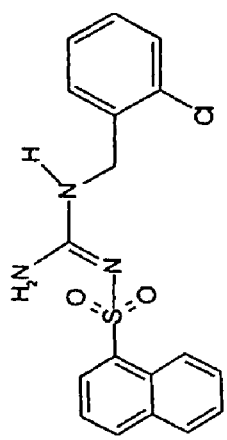
Figure 13:
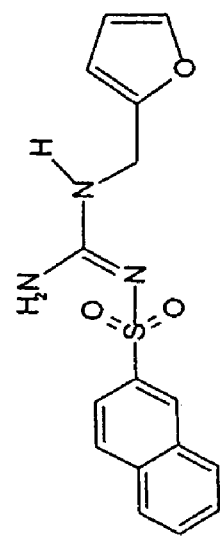
Figure 13:
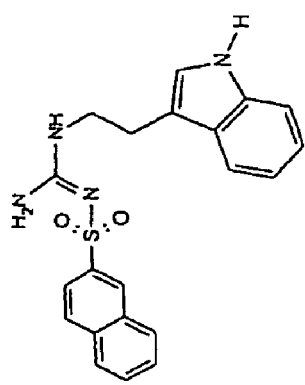
Figure 13:
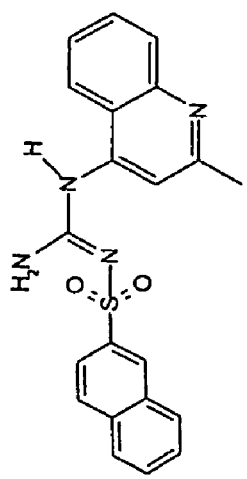
Figure 14:
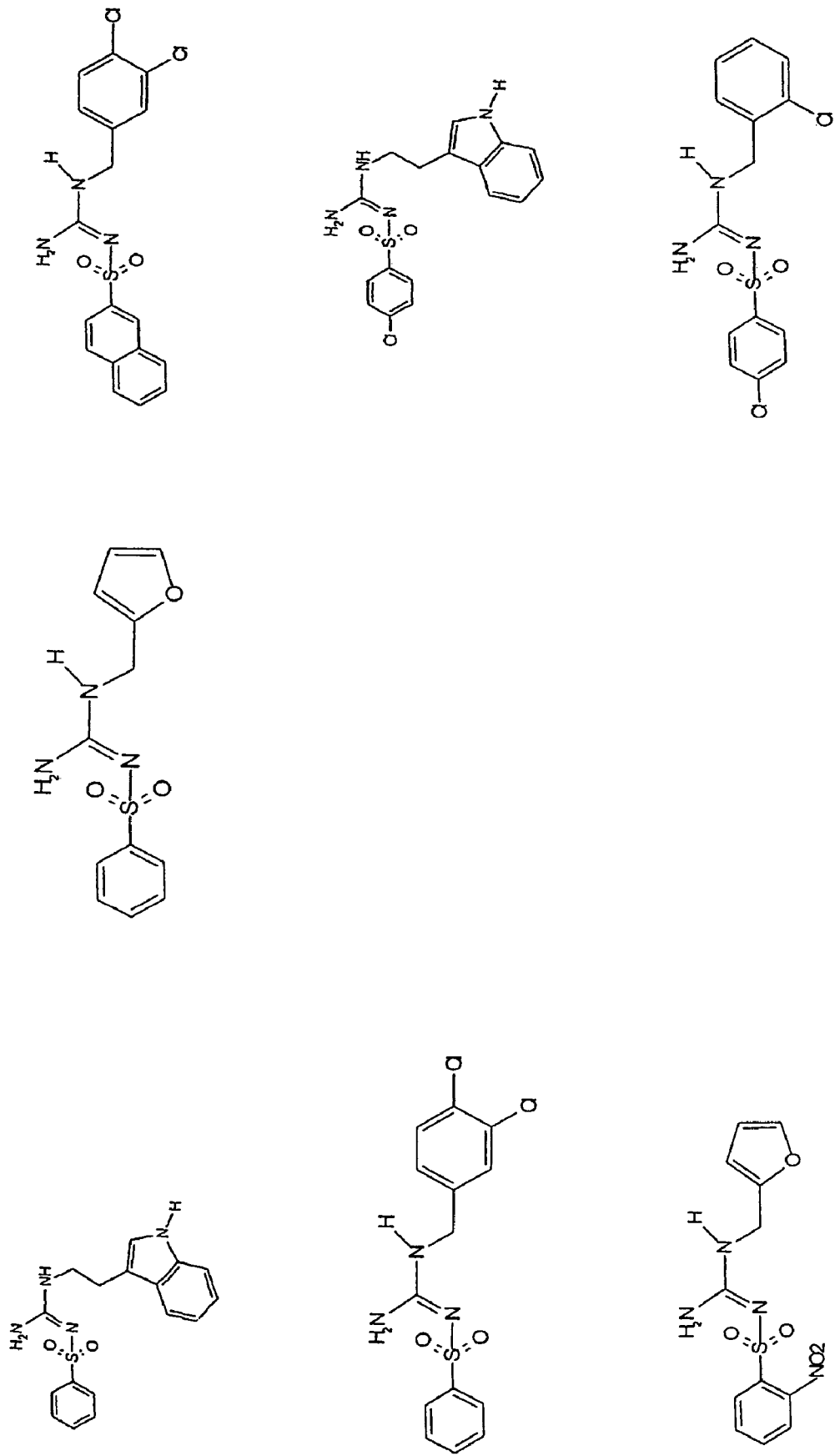
Figure 15:
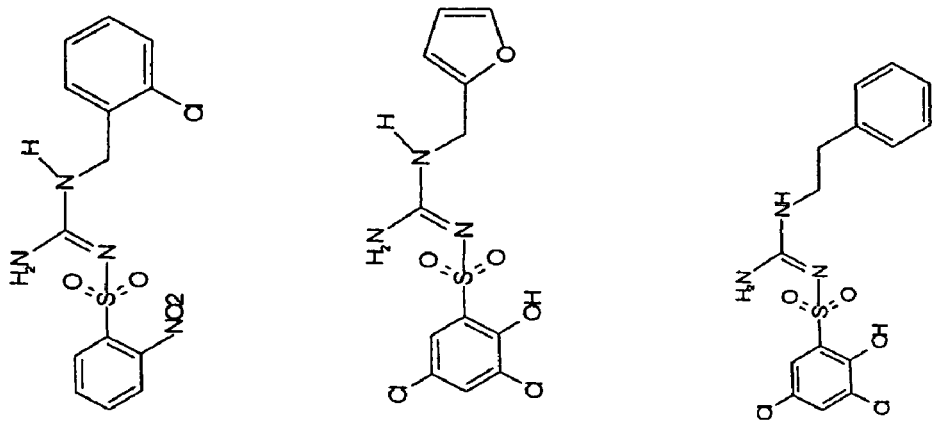
Figure 15:
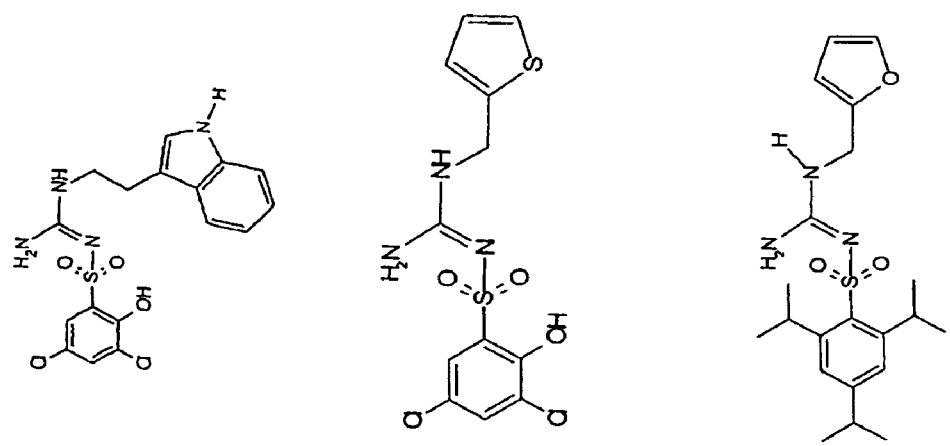
Figure 15:
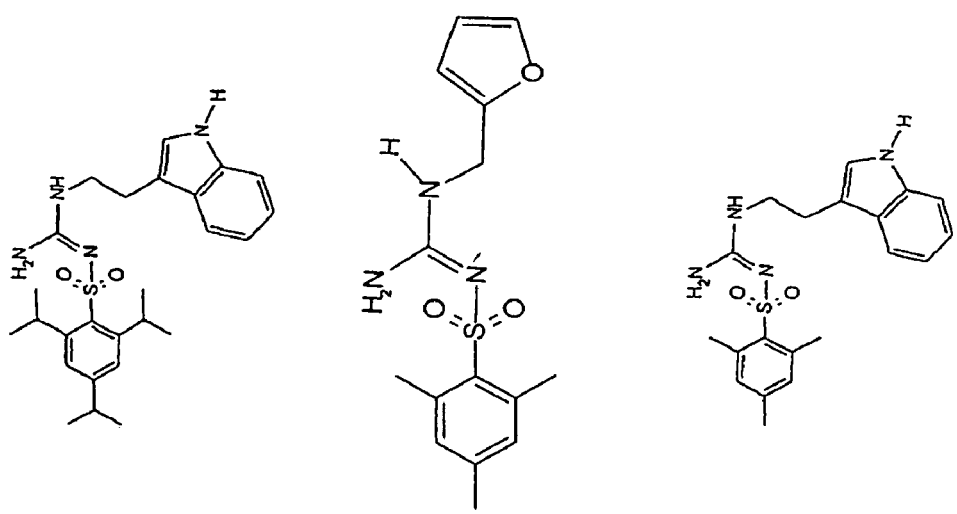
Figure 16:
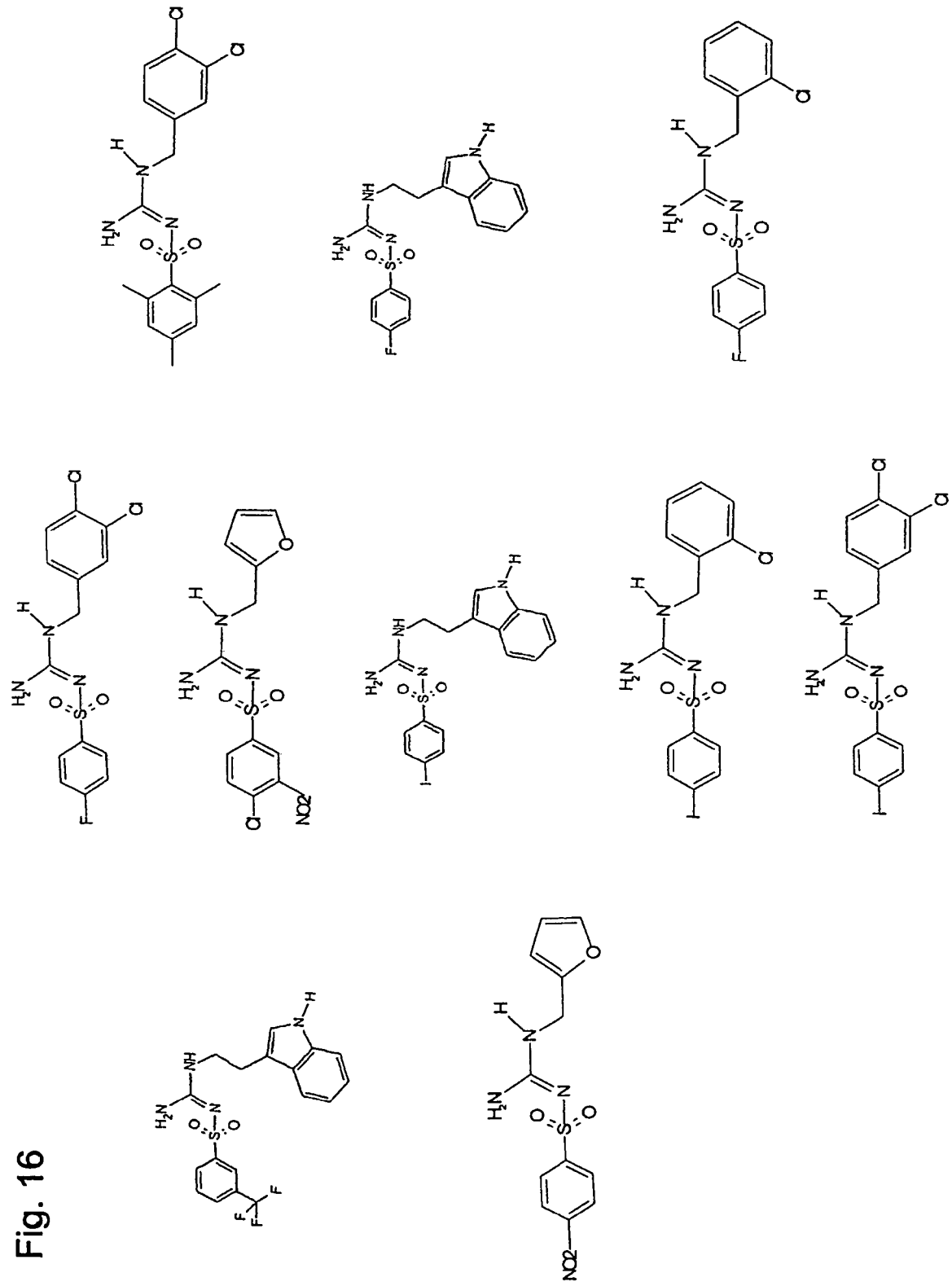
Figure 17:
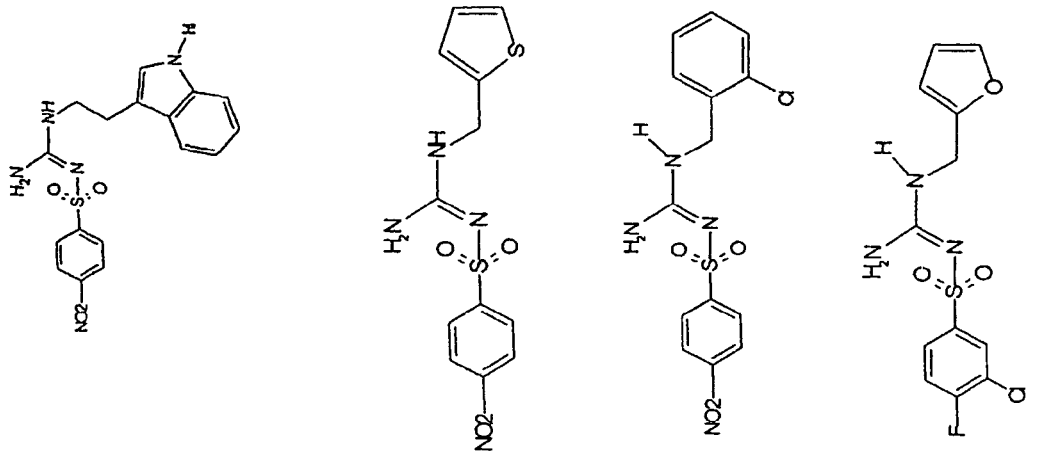
Figure 17:
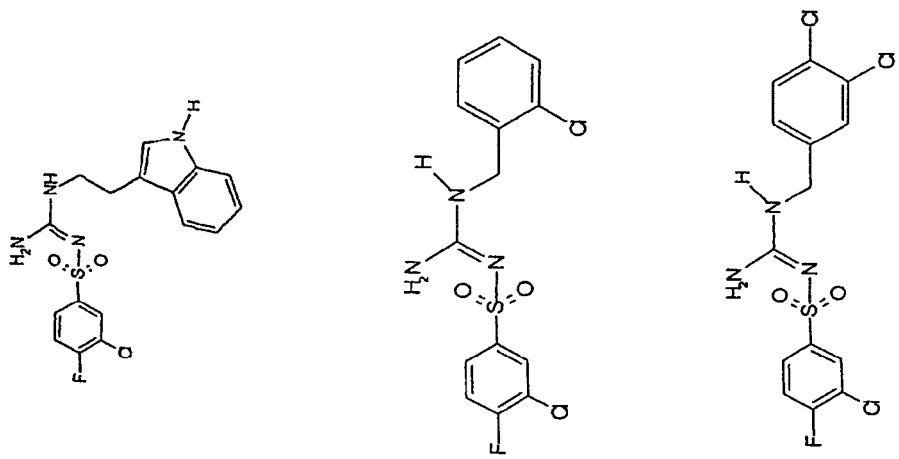
Figure 17:
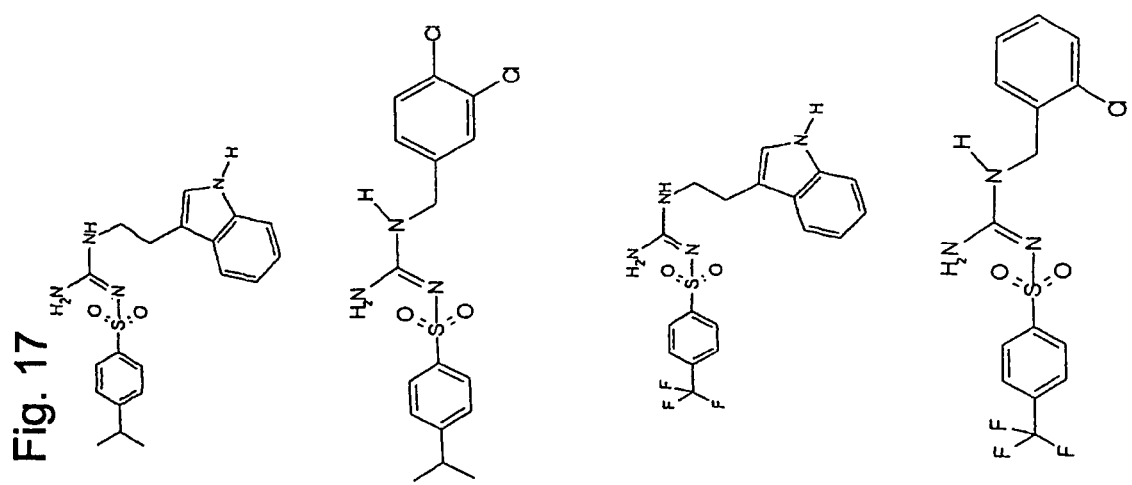
Figure 18:
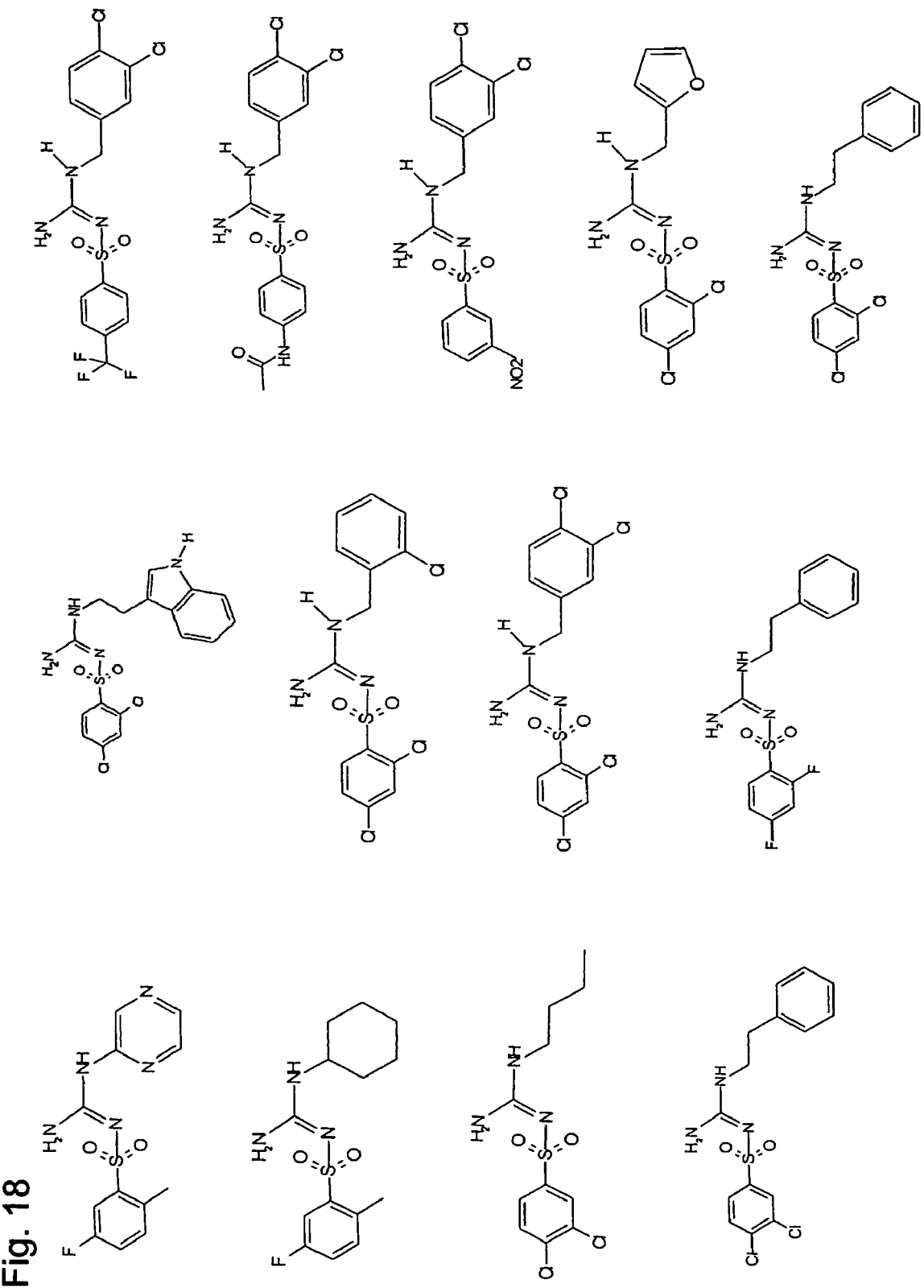
Figure 19:
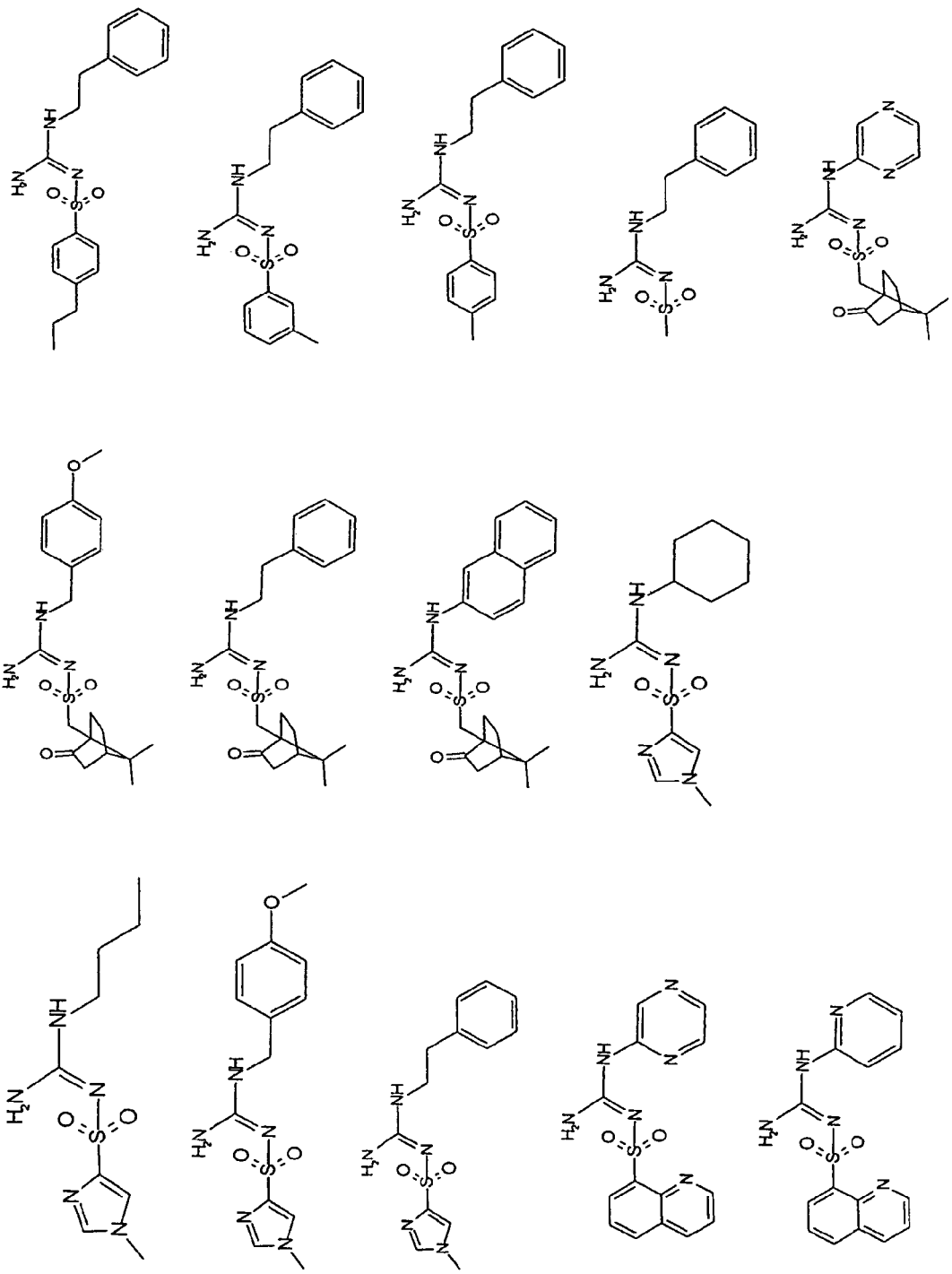
Figure 20:
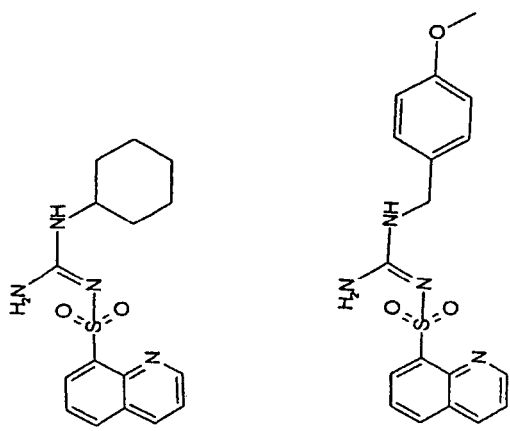
Figure 20:
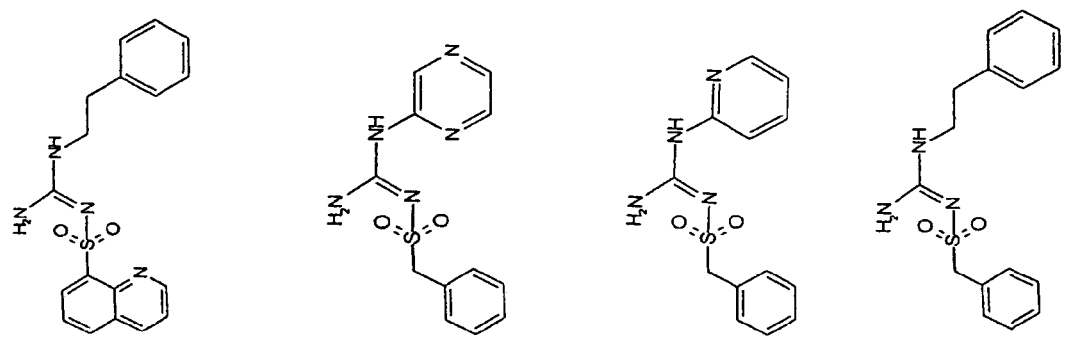
Figure 20:
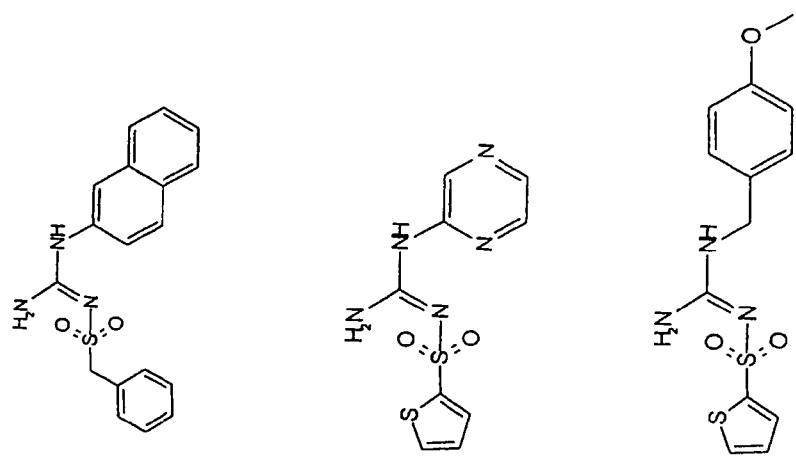
Figure 21:
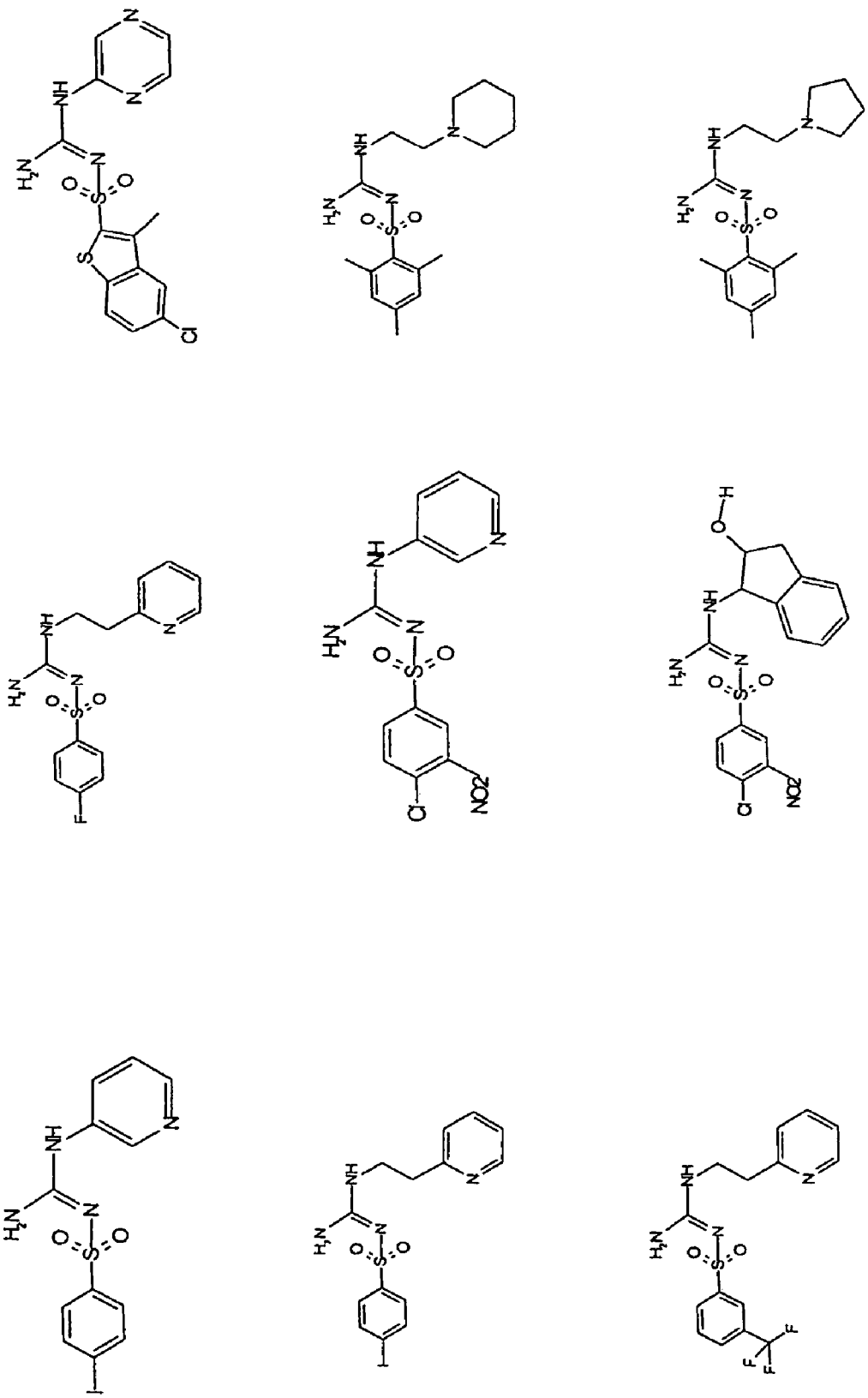
Figure 22:
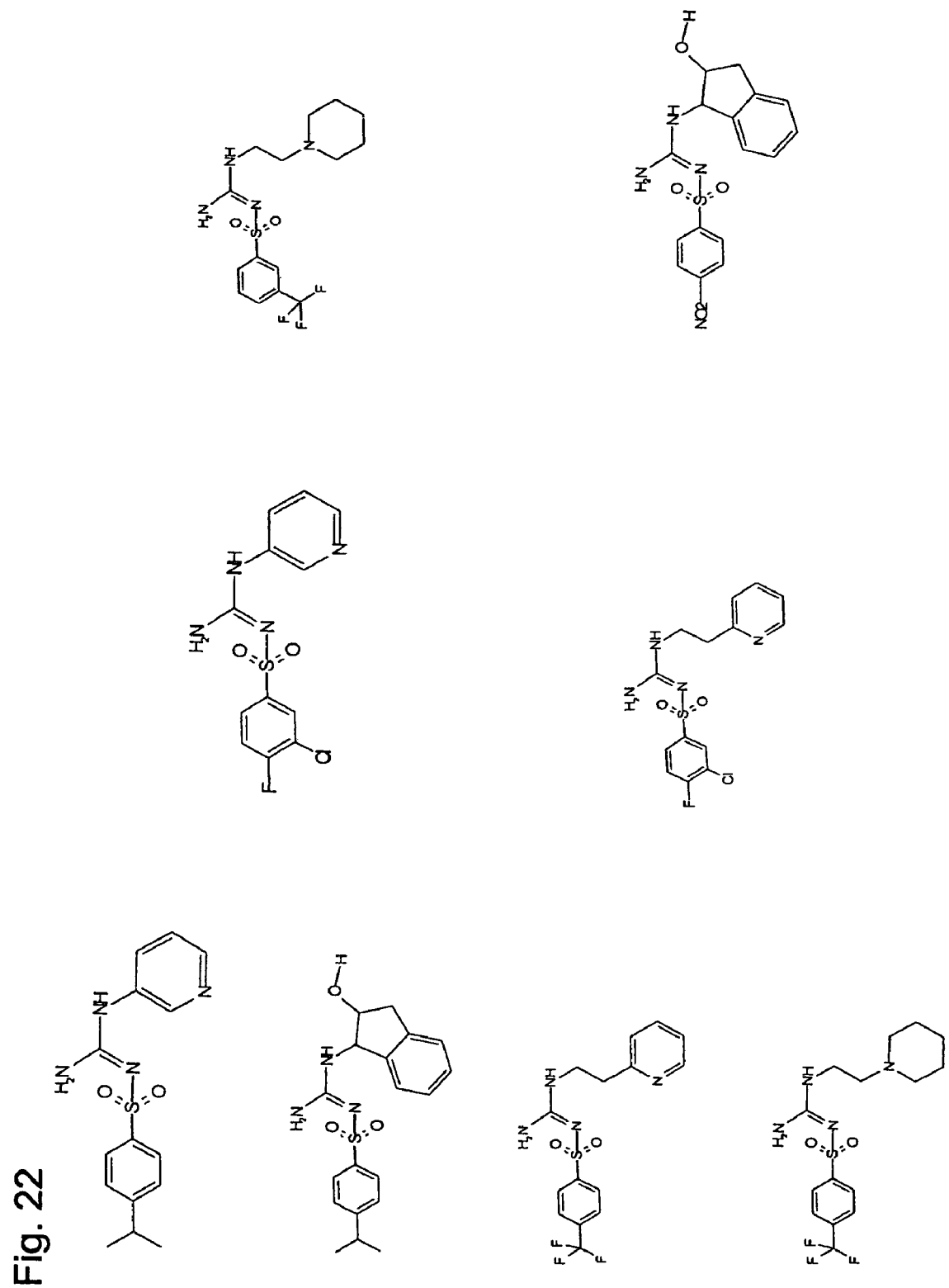
Figure 23:
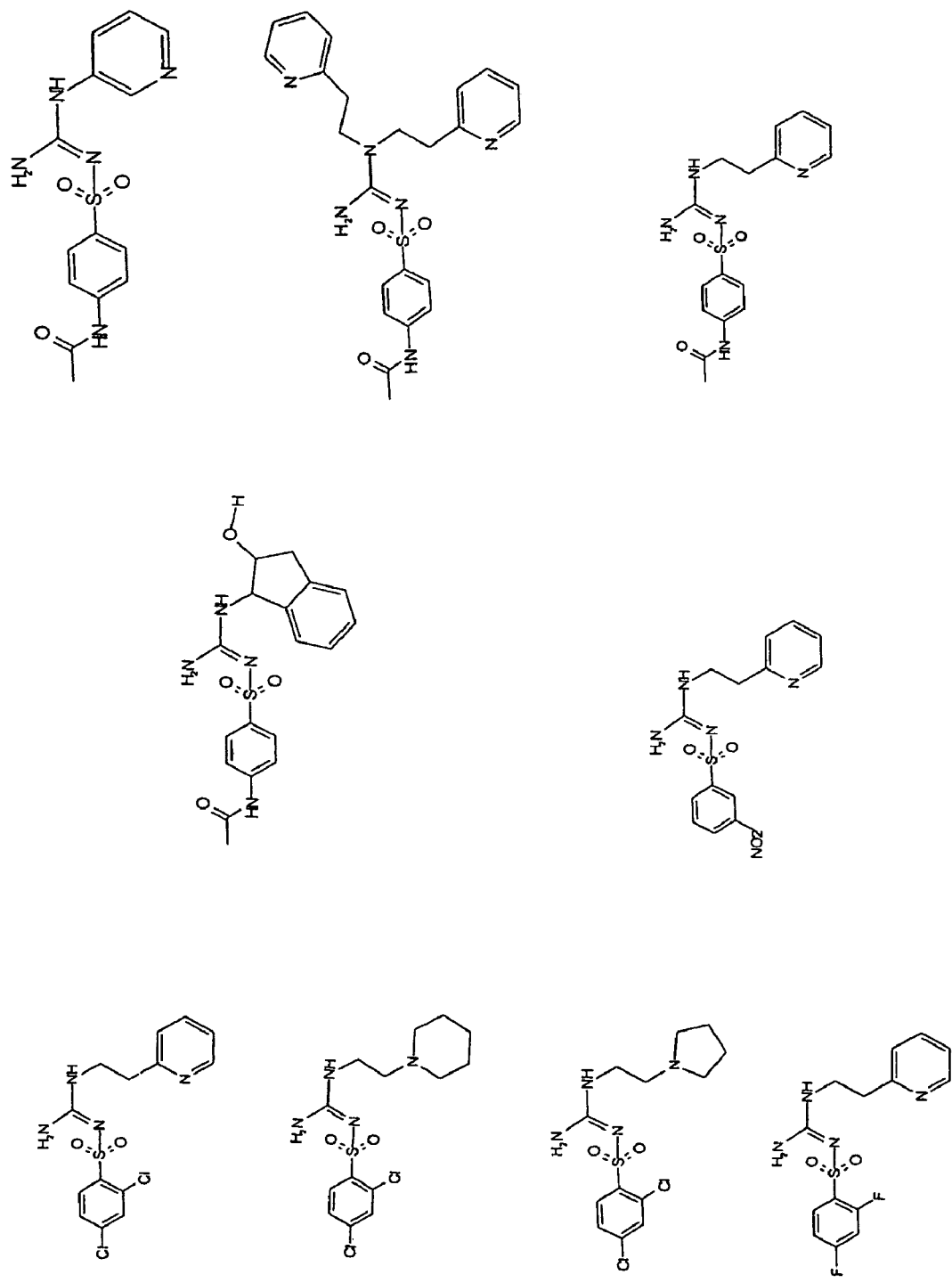
Figure 24:
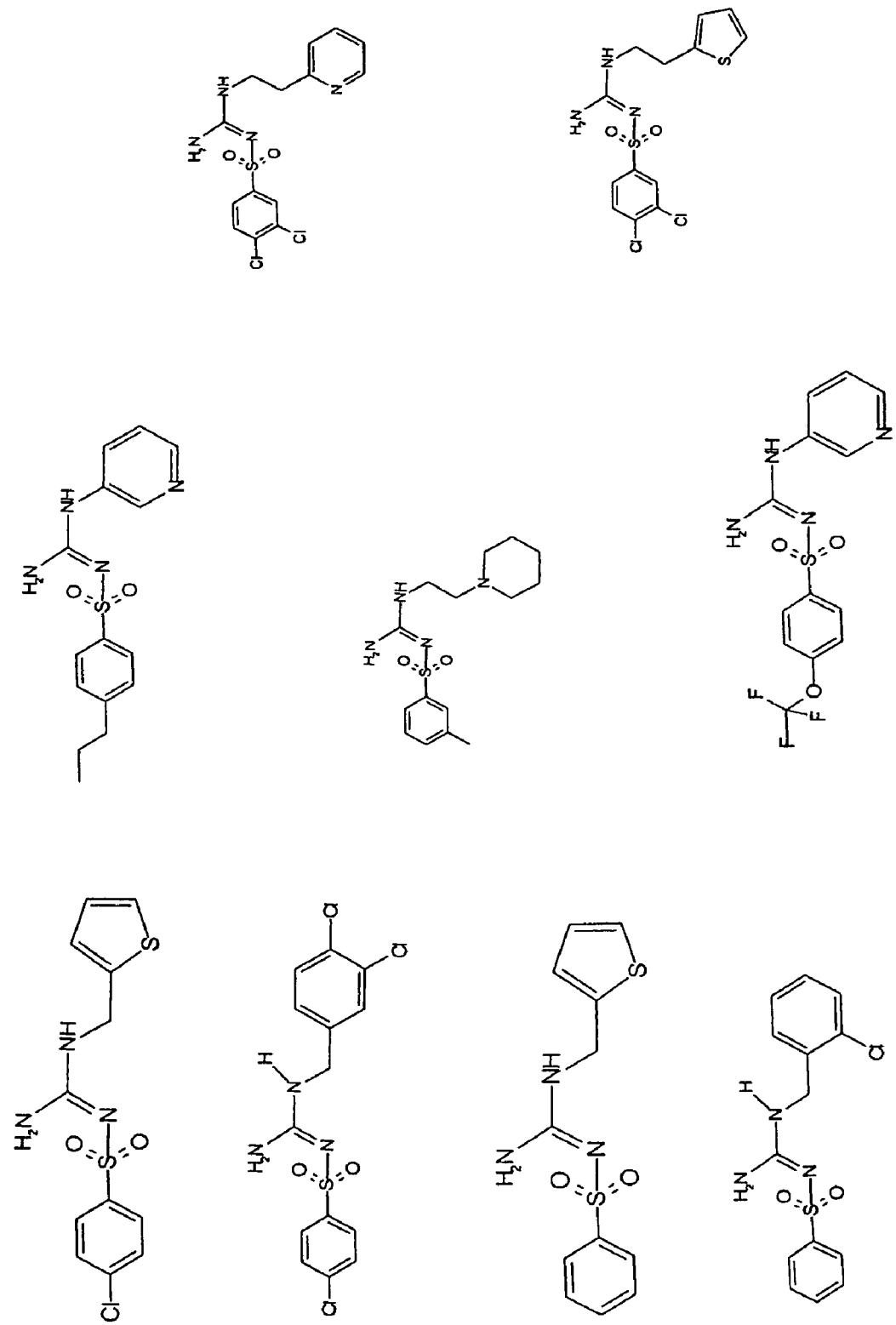
Figure 25:
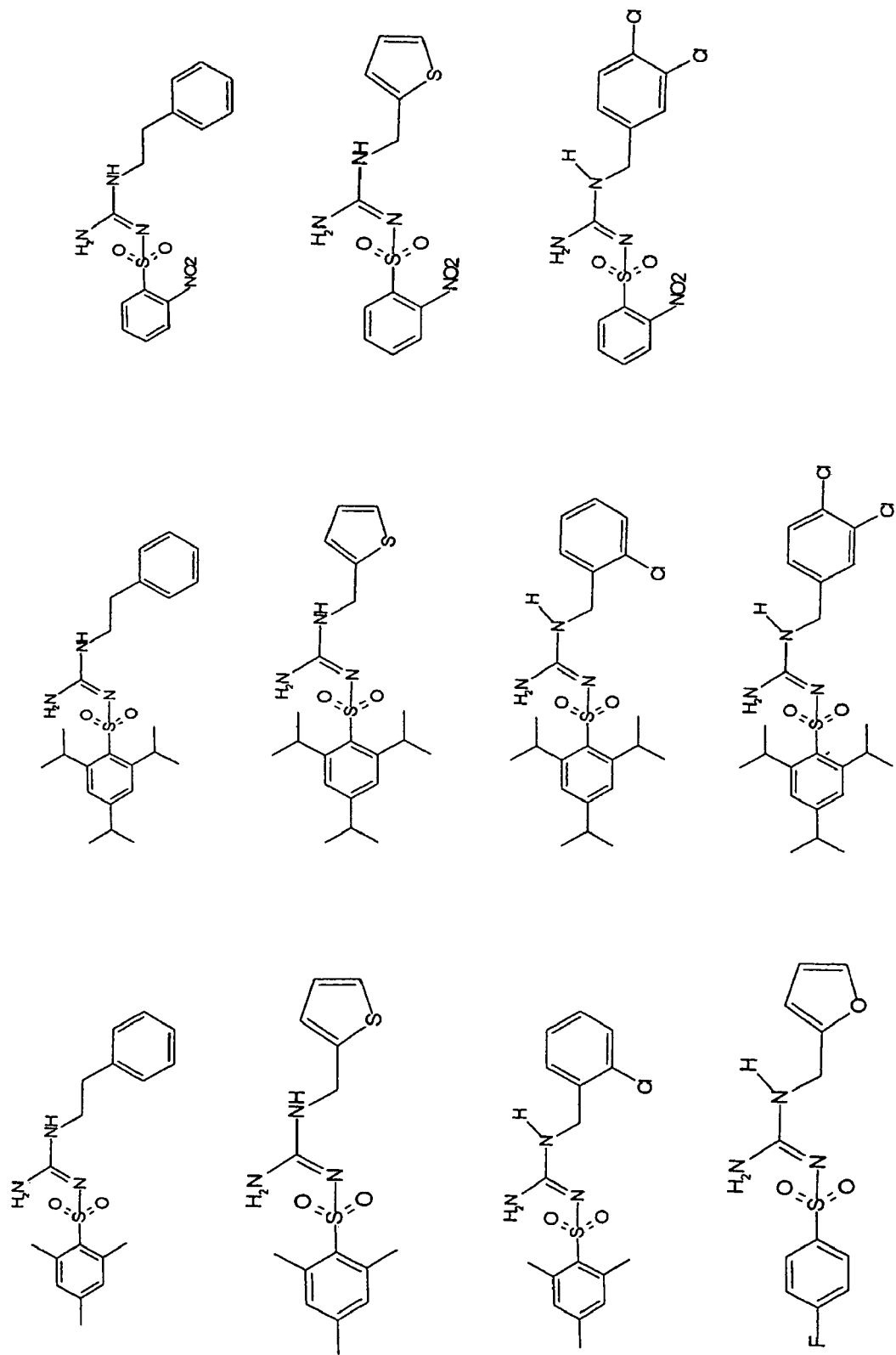
Figure 26:
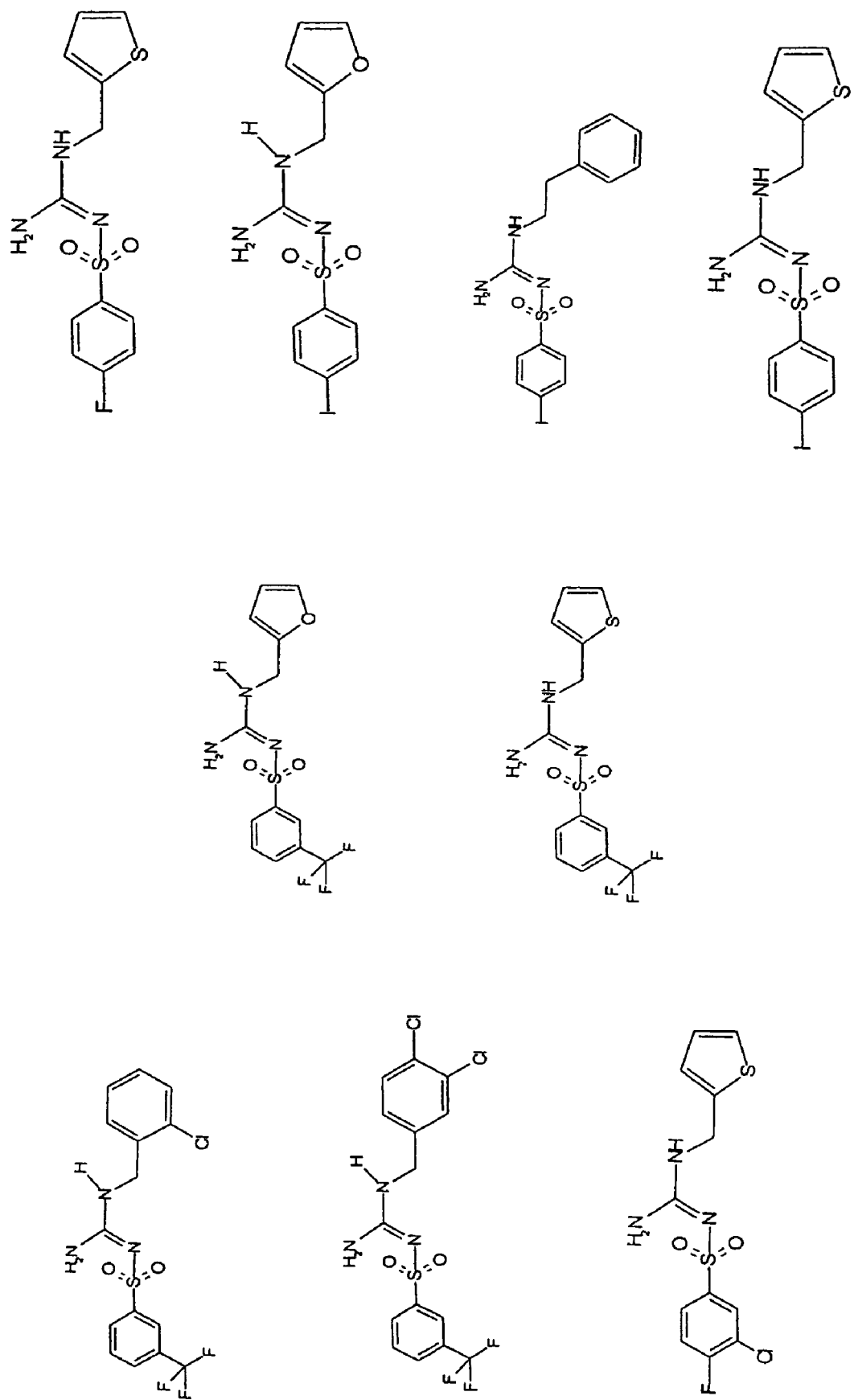
Figure 27:
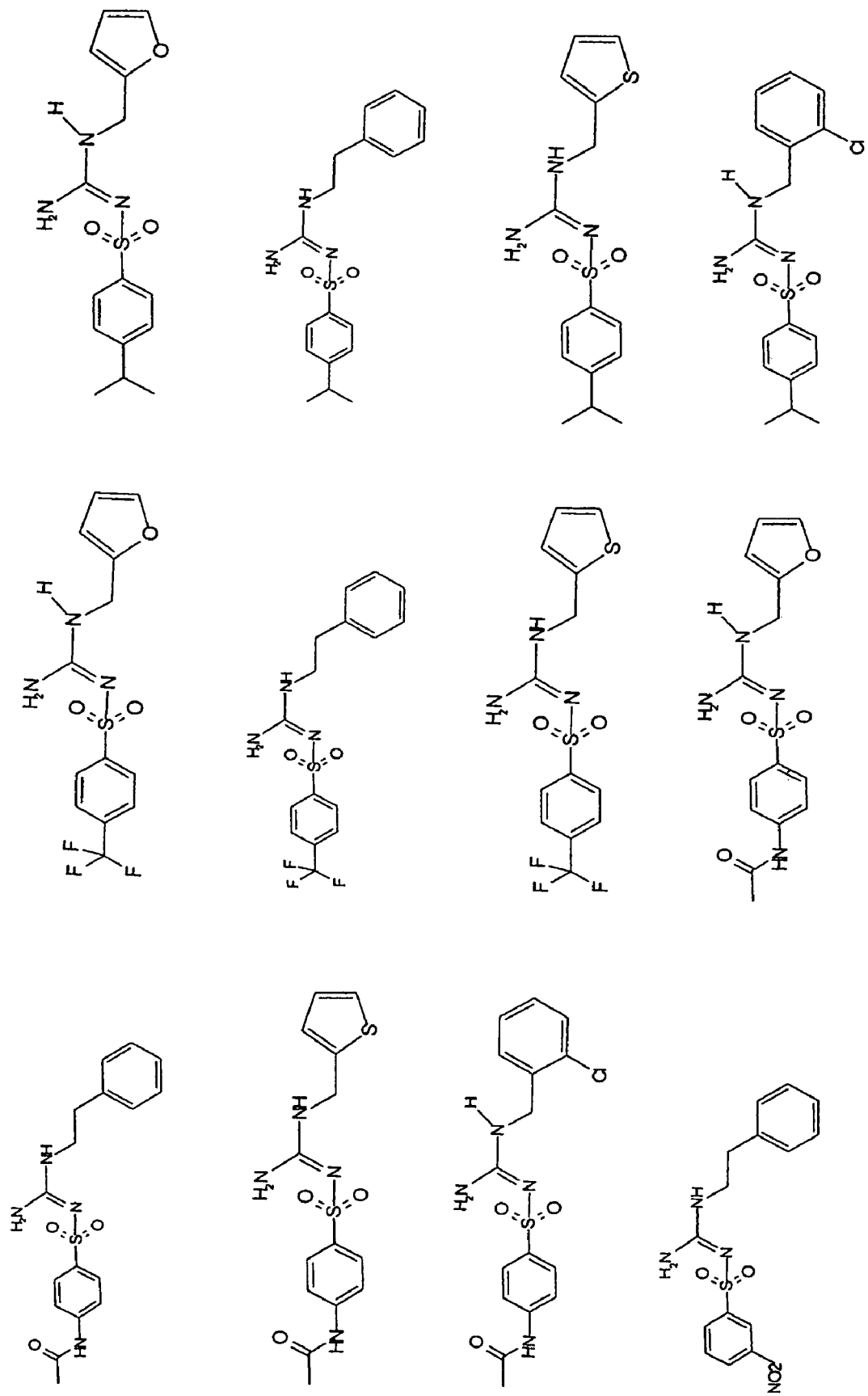
Figure 28:
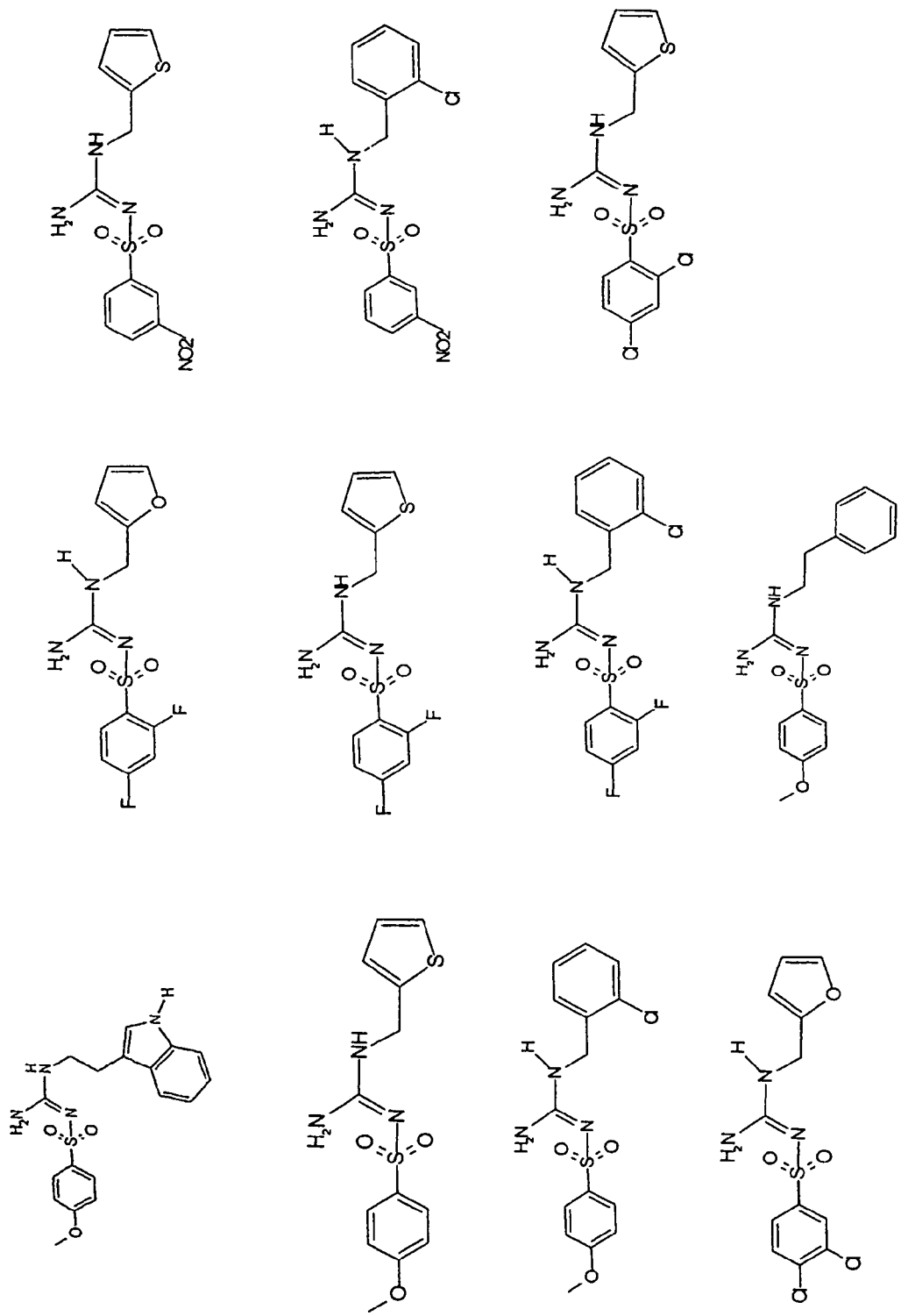
Figure 29:
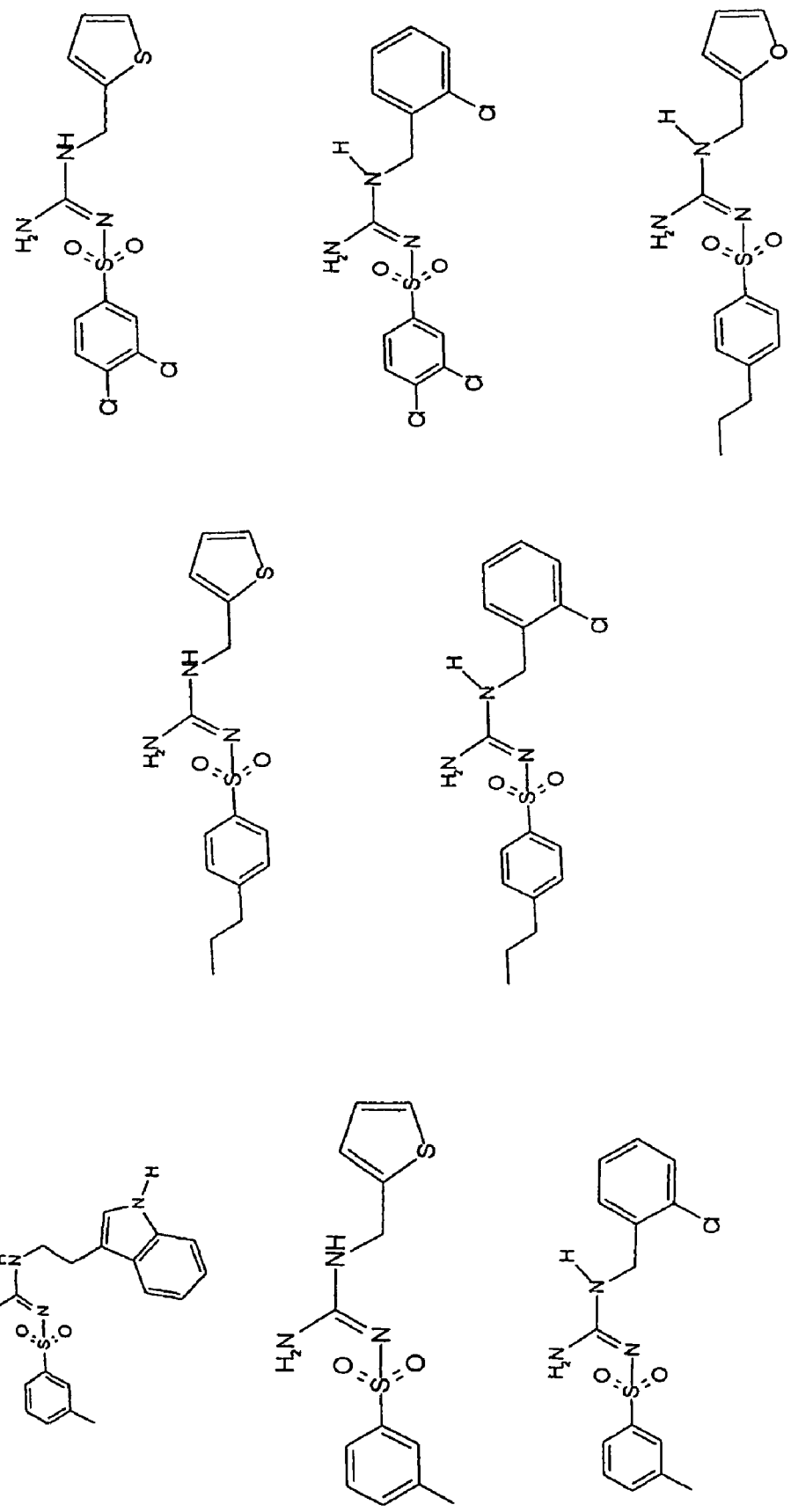
Figure 30:
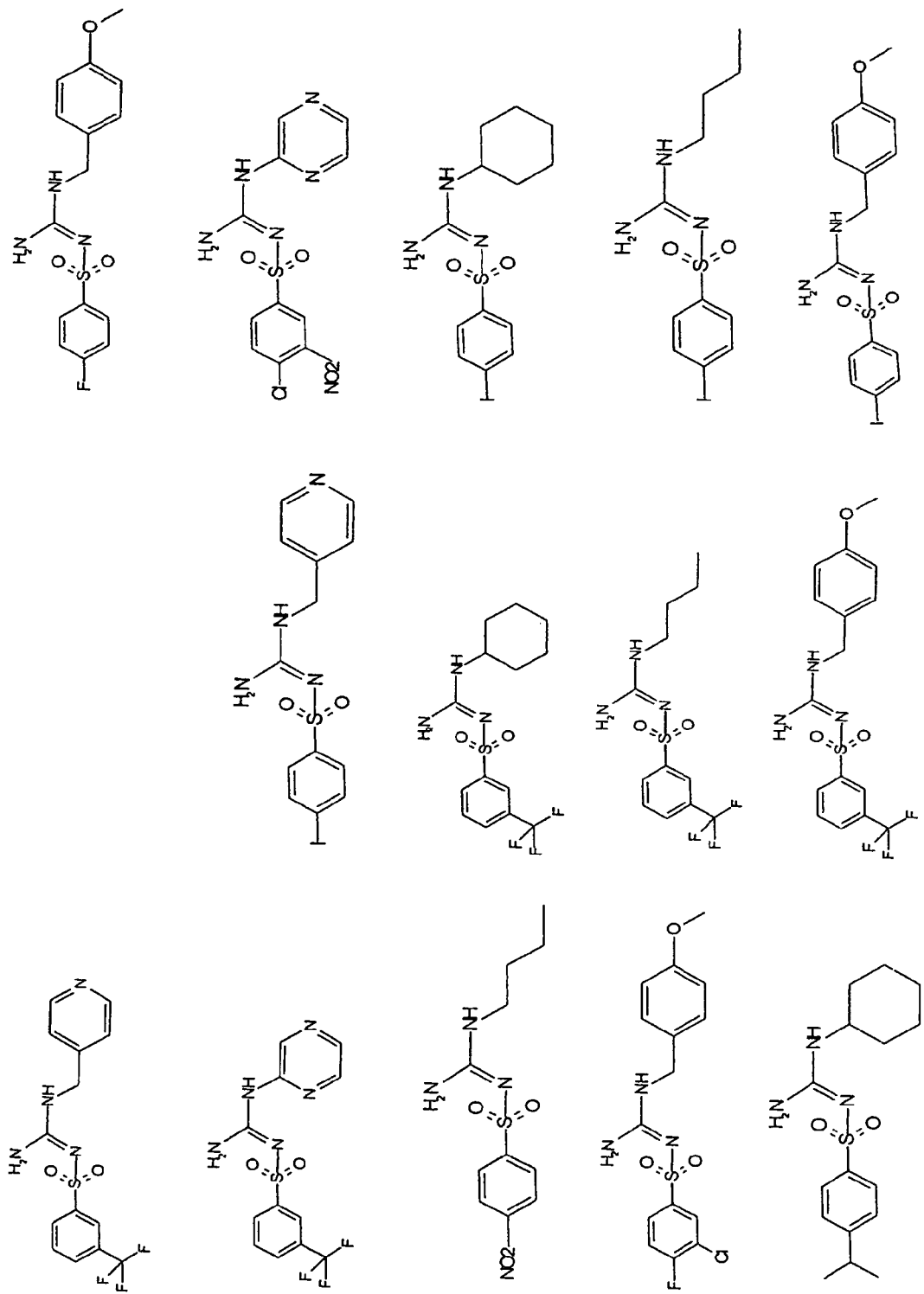
Figure 31:
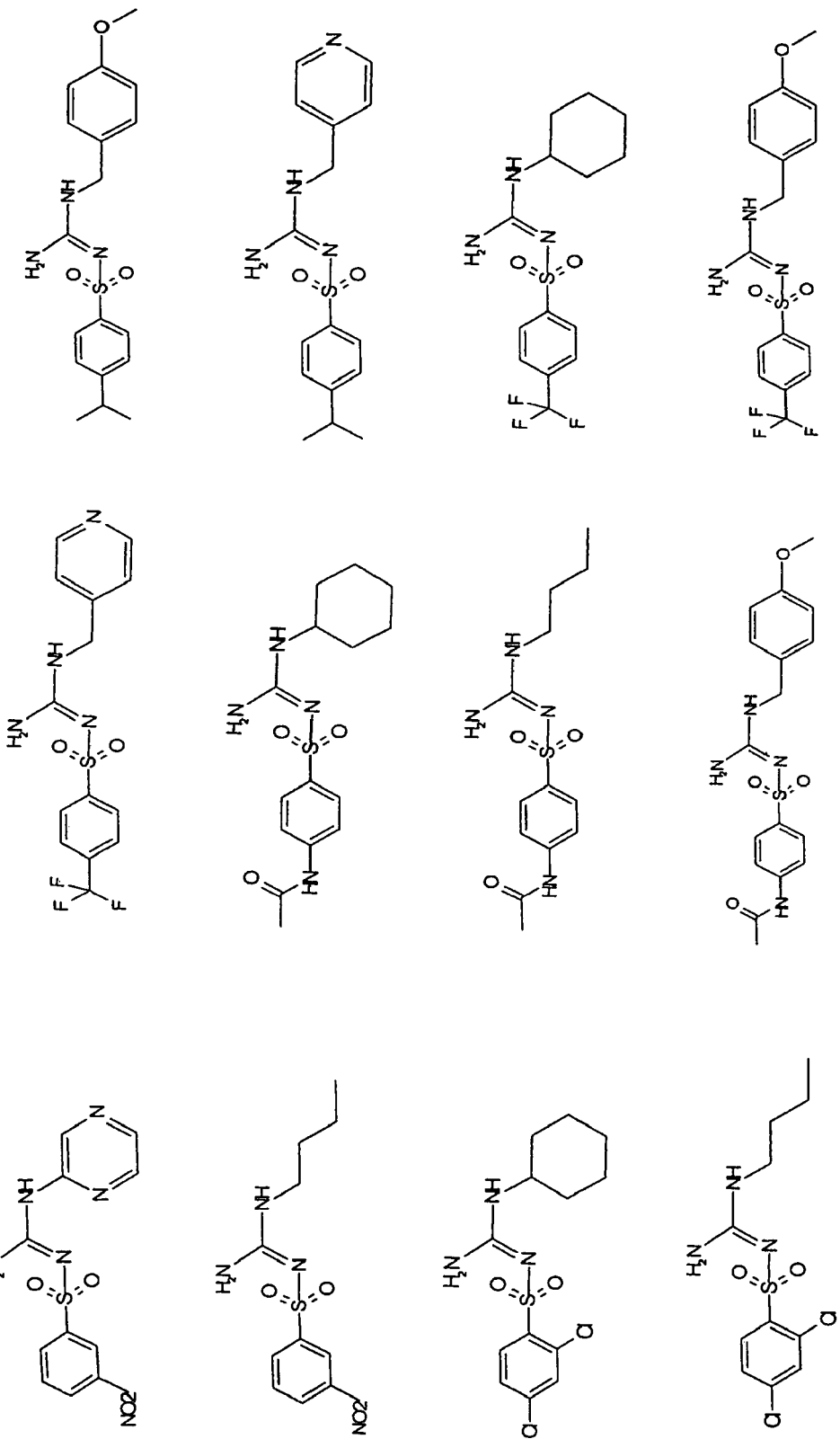
Figure 32:
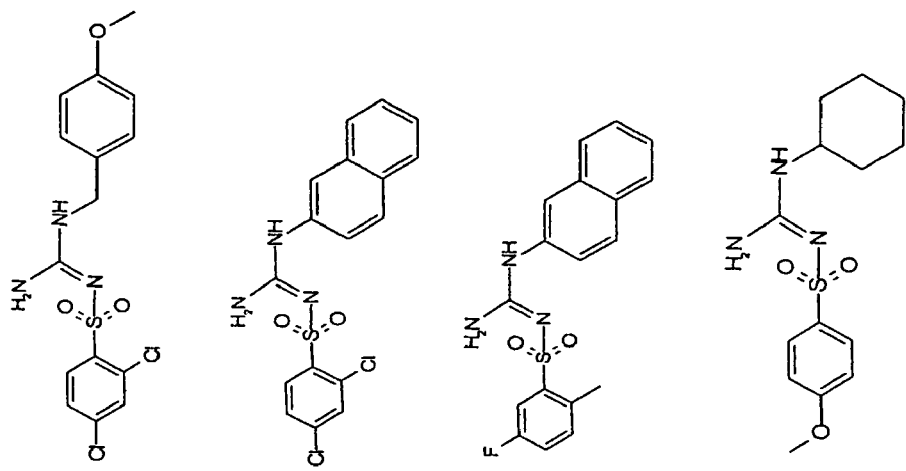
Figure 32:
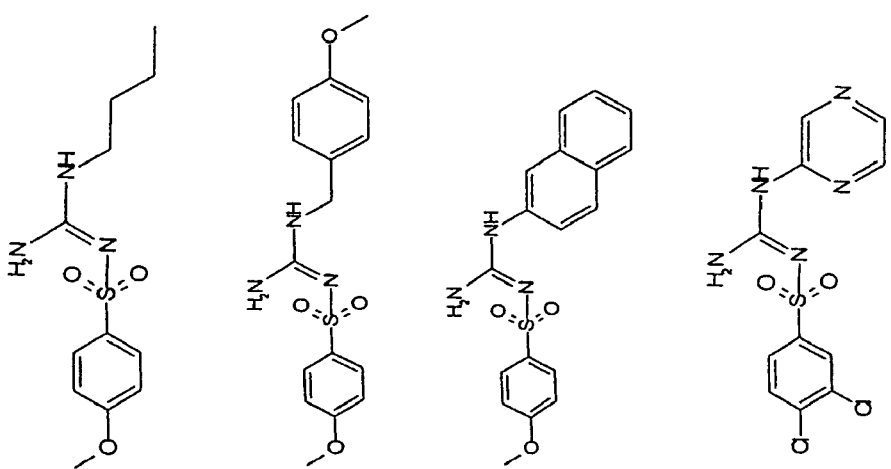
Figure 32:
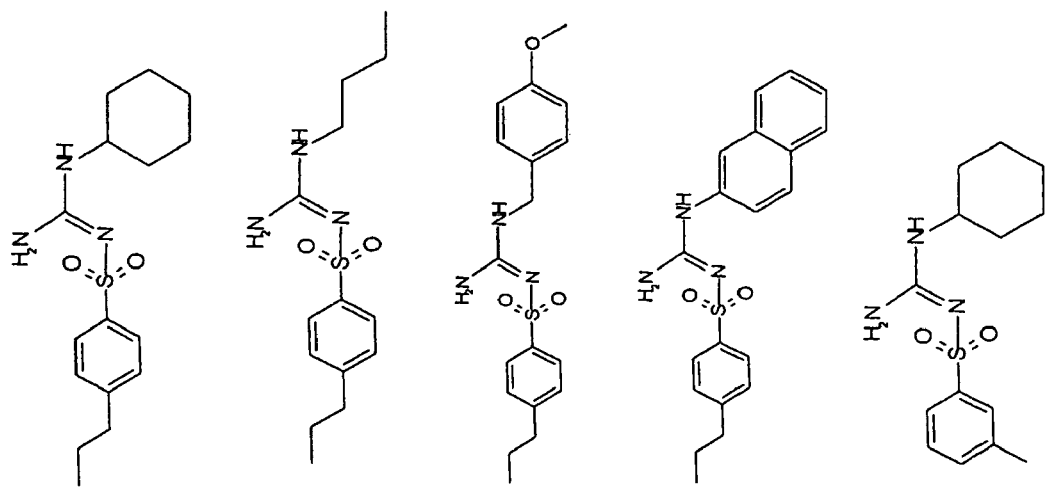
Figure 33:
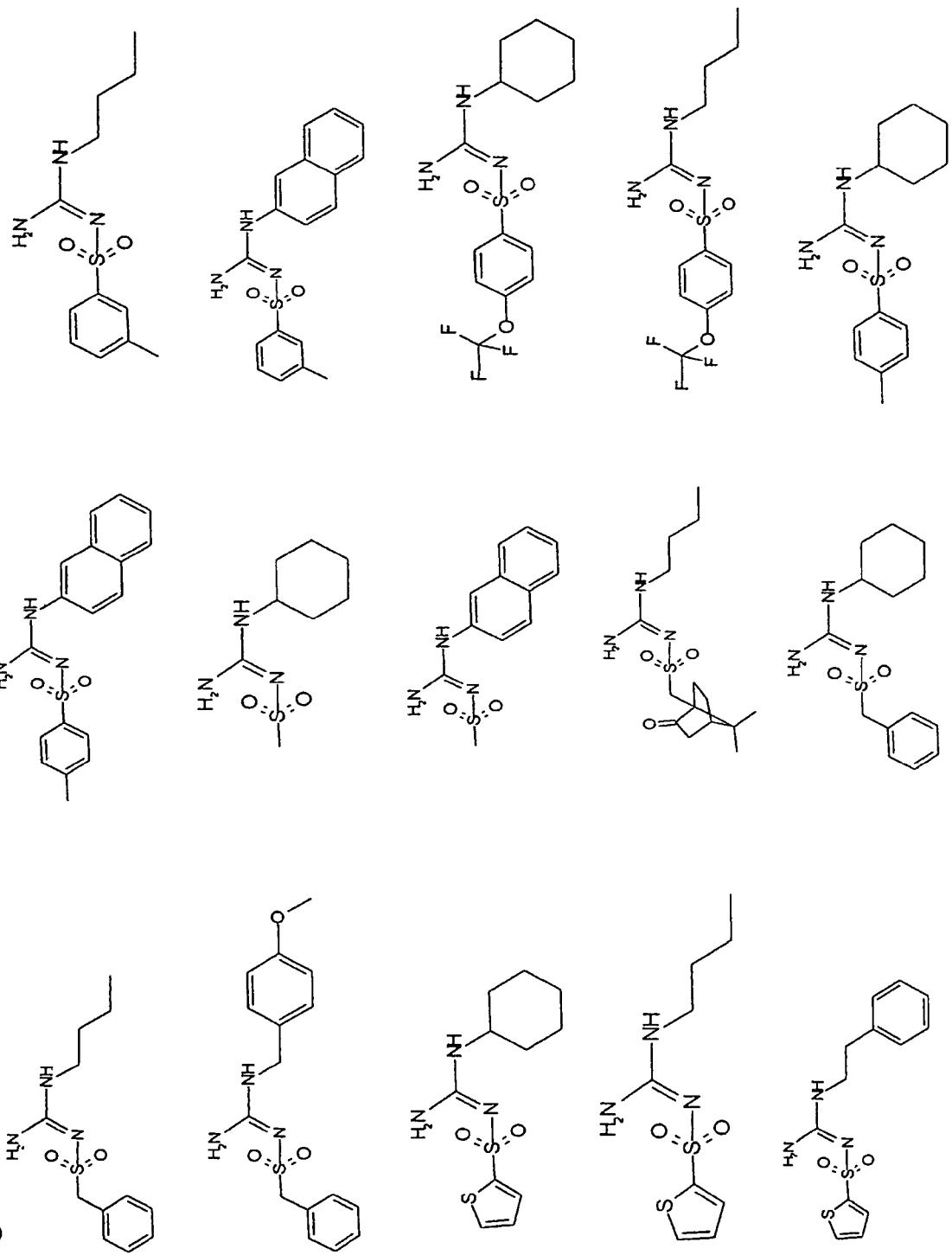
Figure 34:
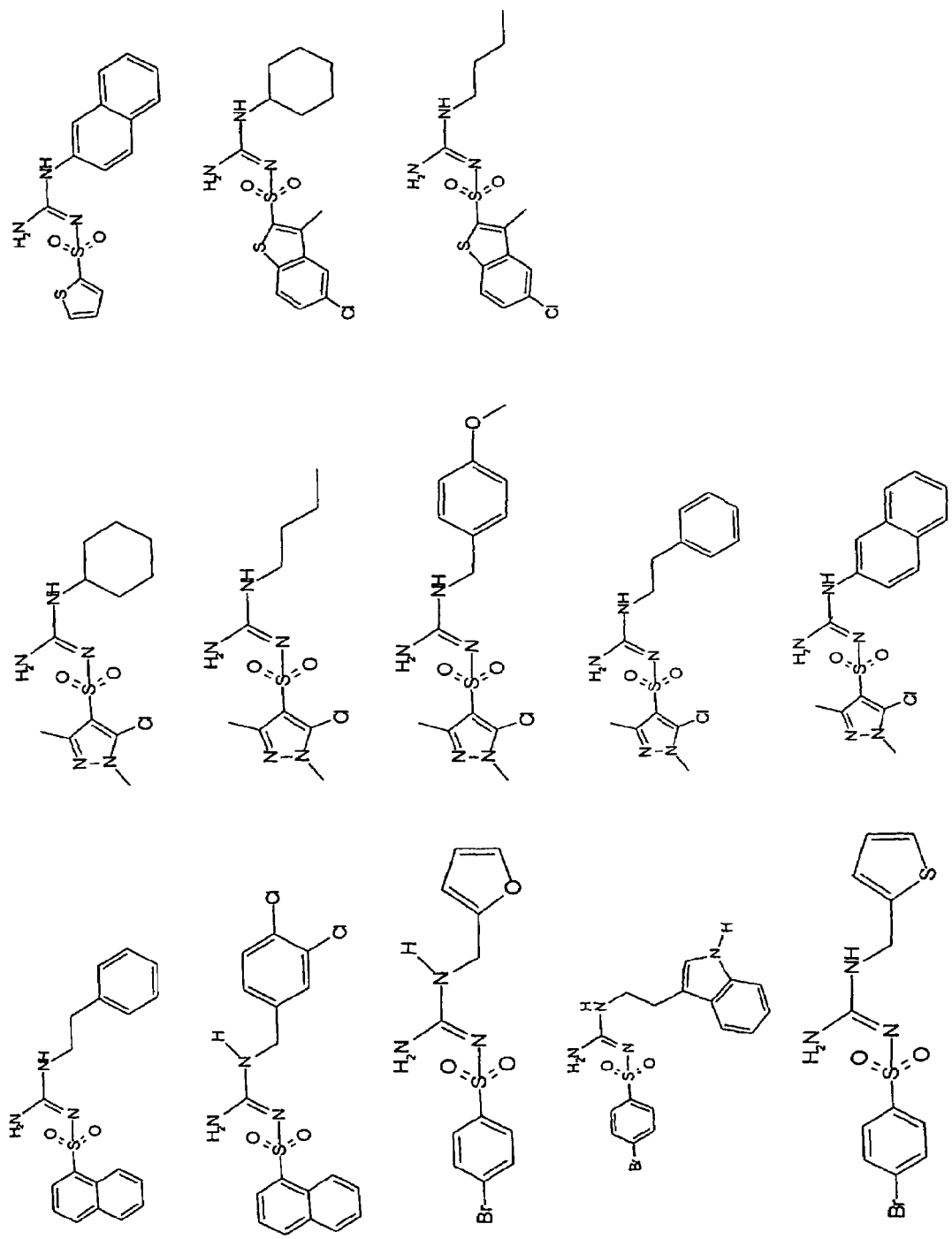
Figure 35:
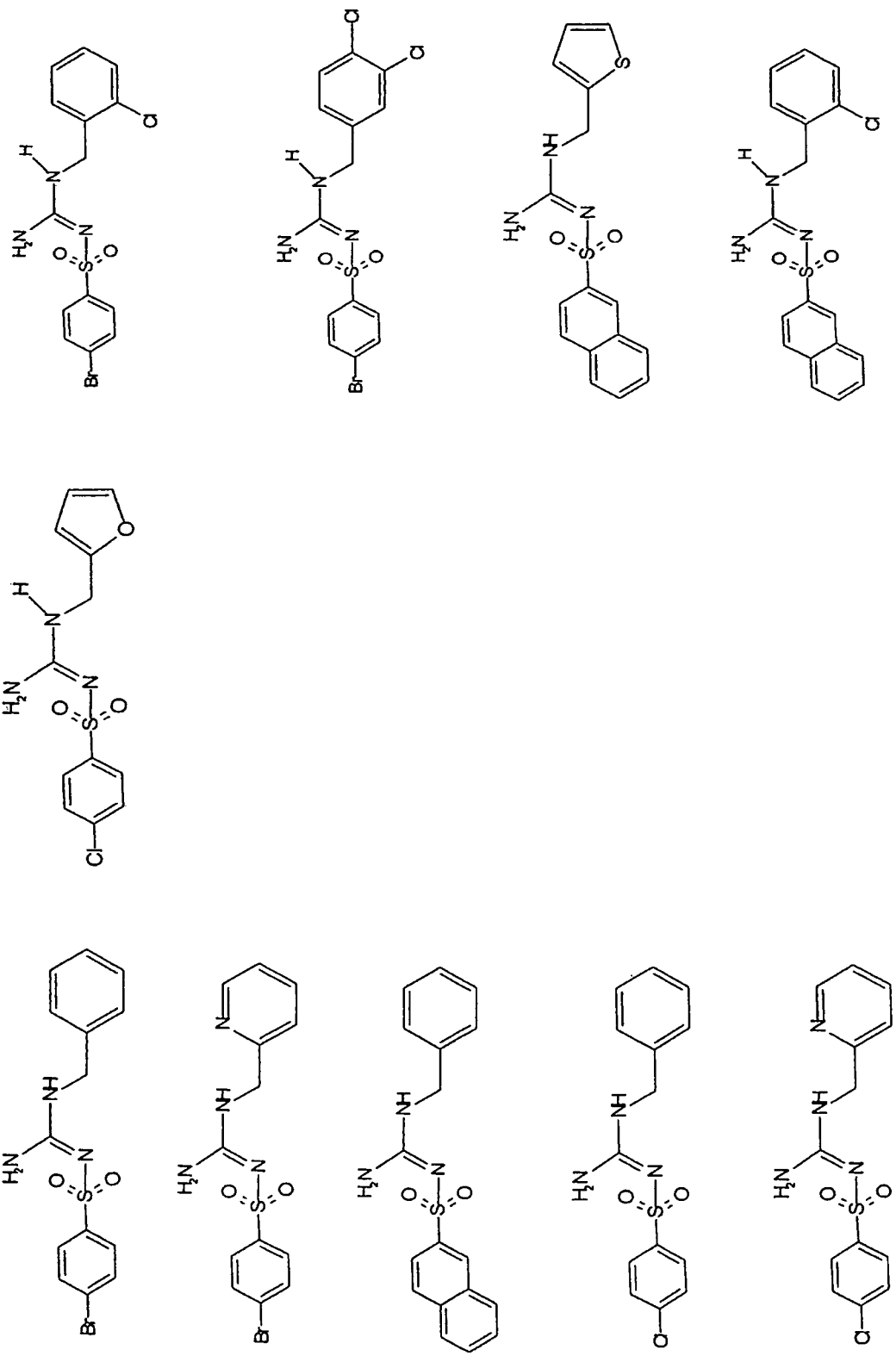
Figure 36:
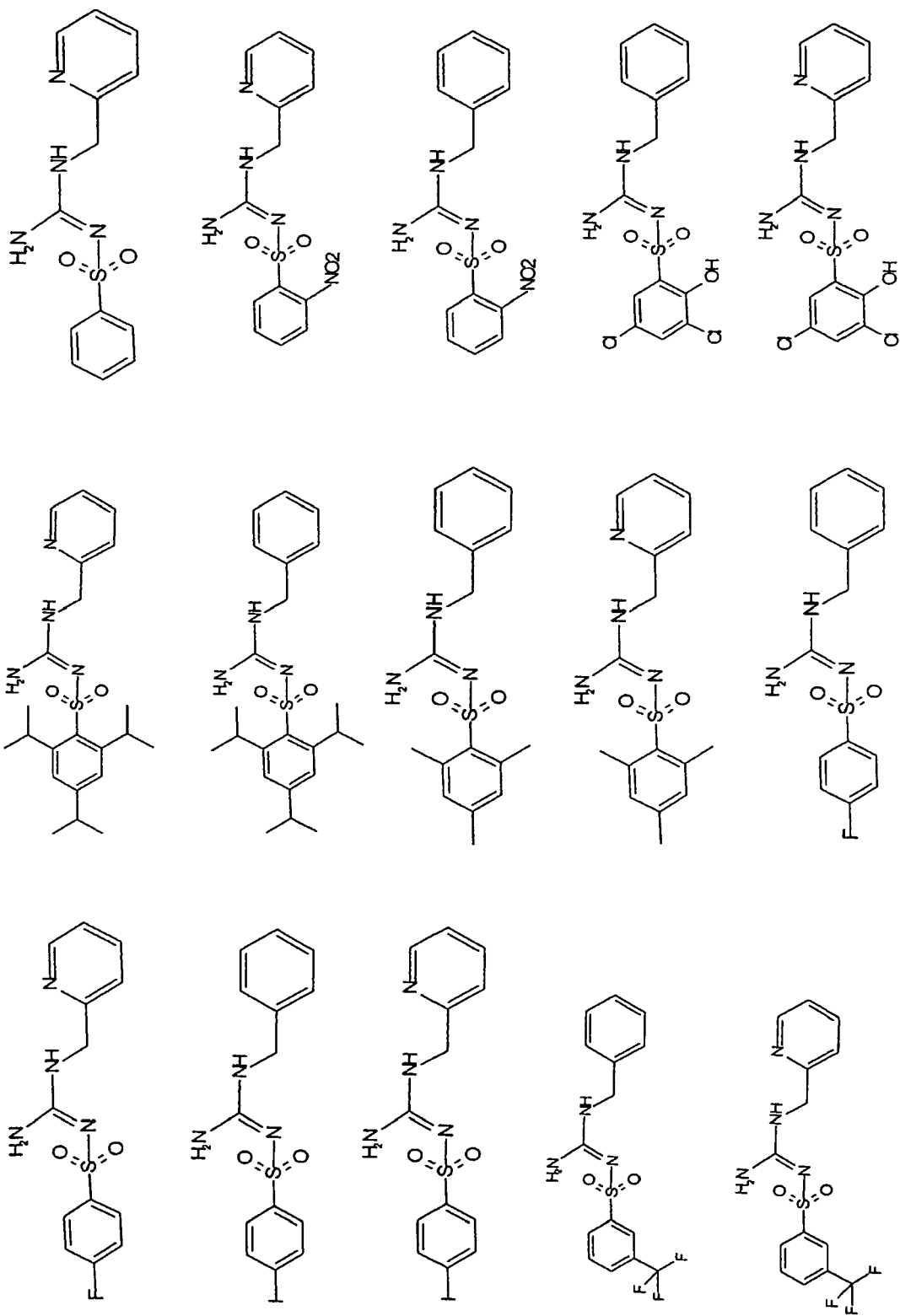
Figure 37:
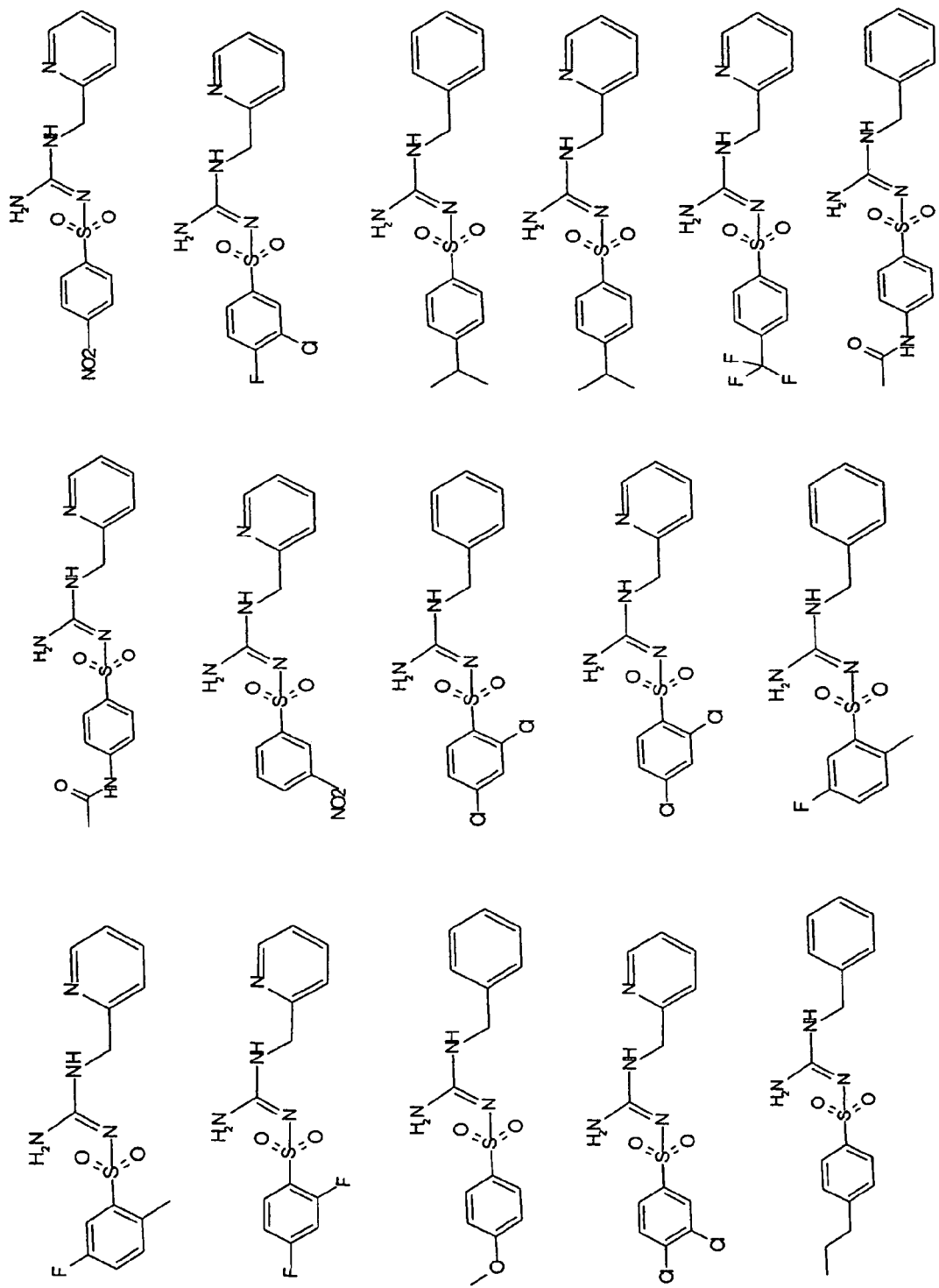
Figure 38:
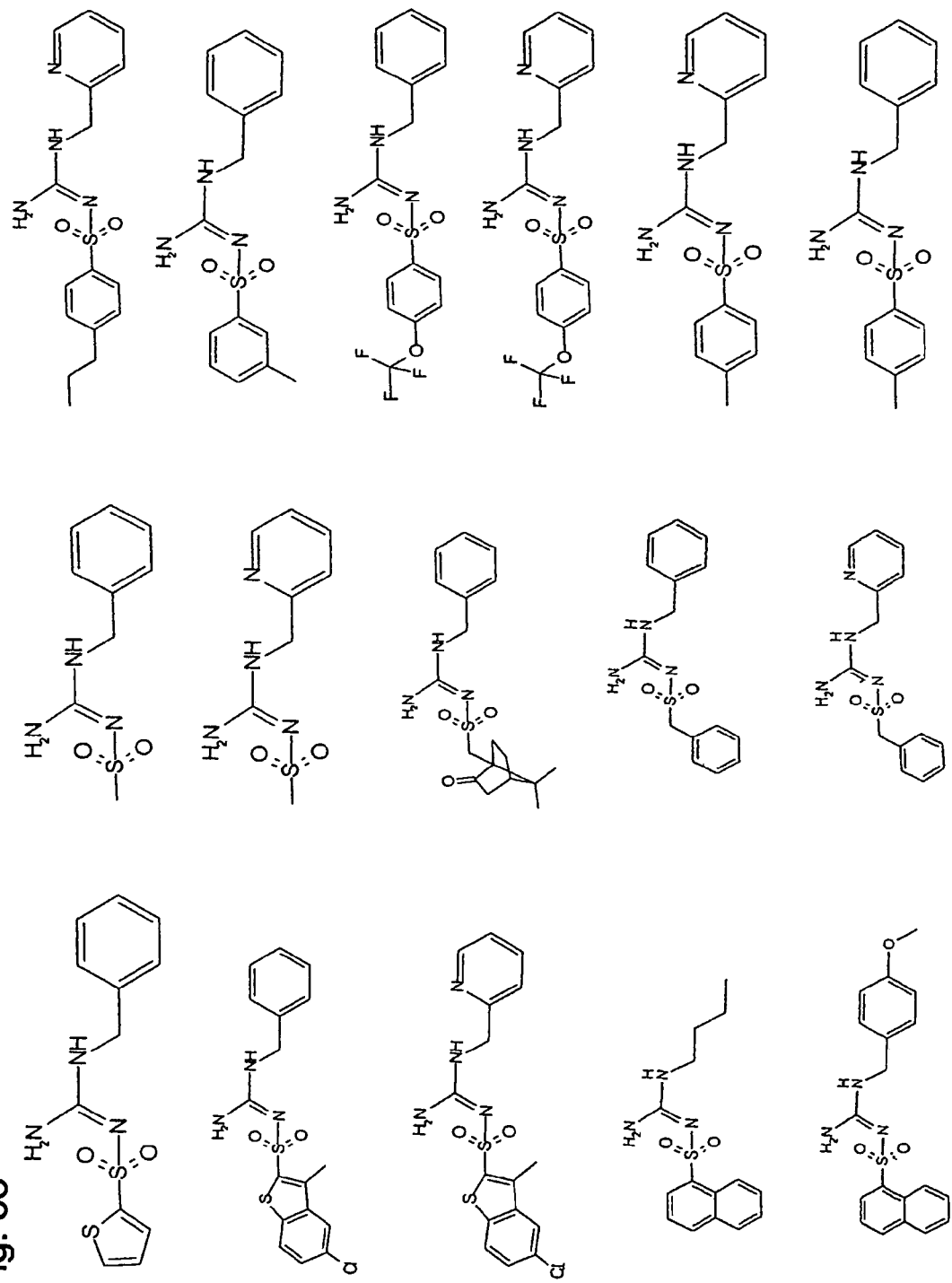
Figure 39:
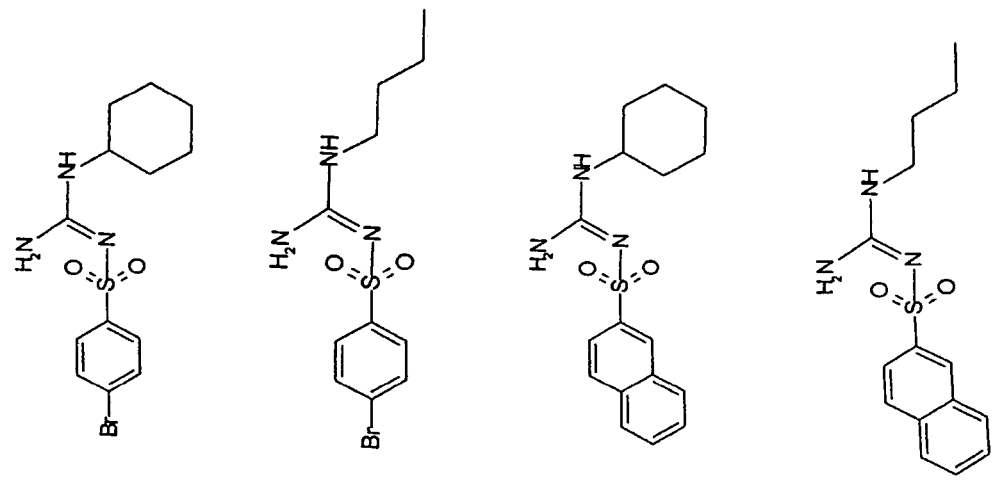
Figure 39:
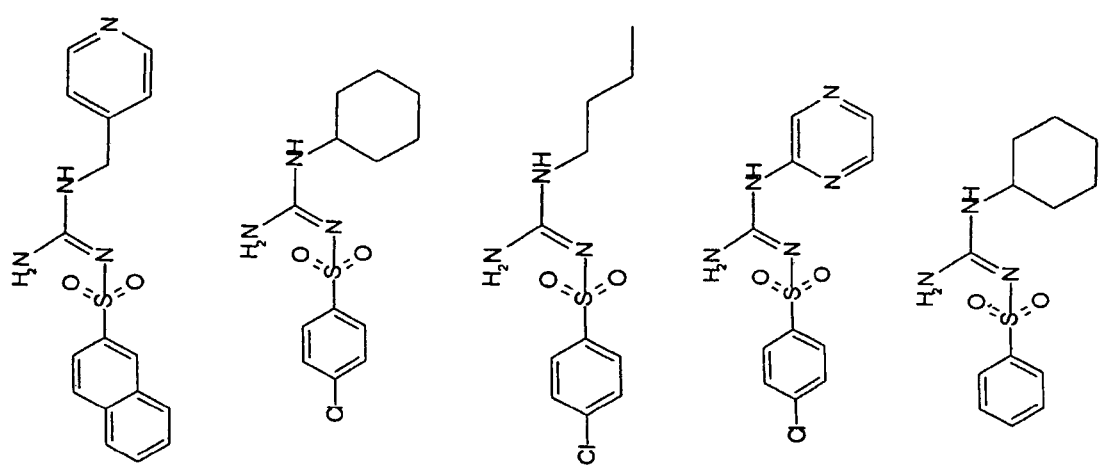
Figure 39:
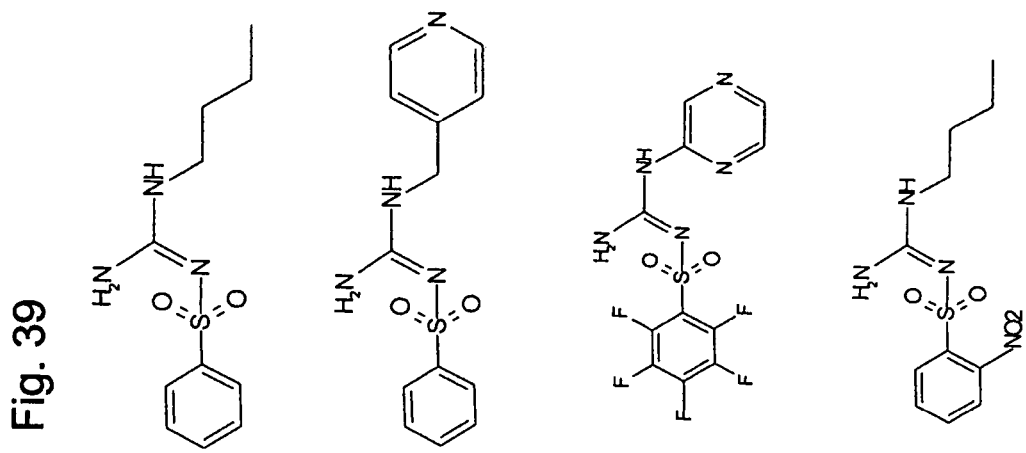
Figure 40:
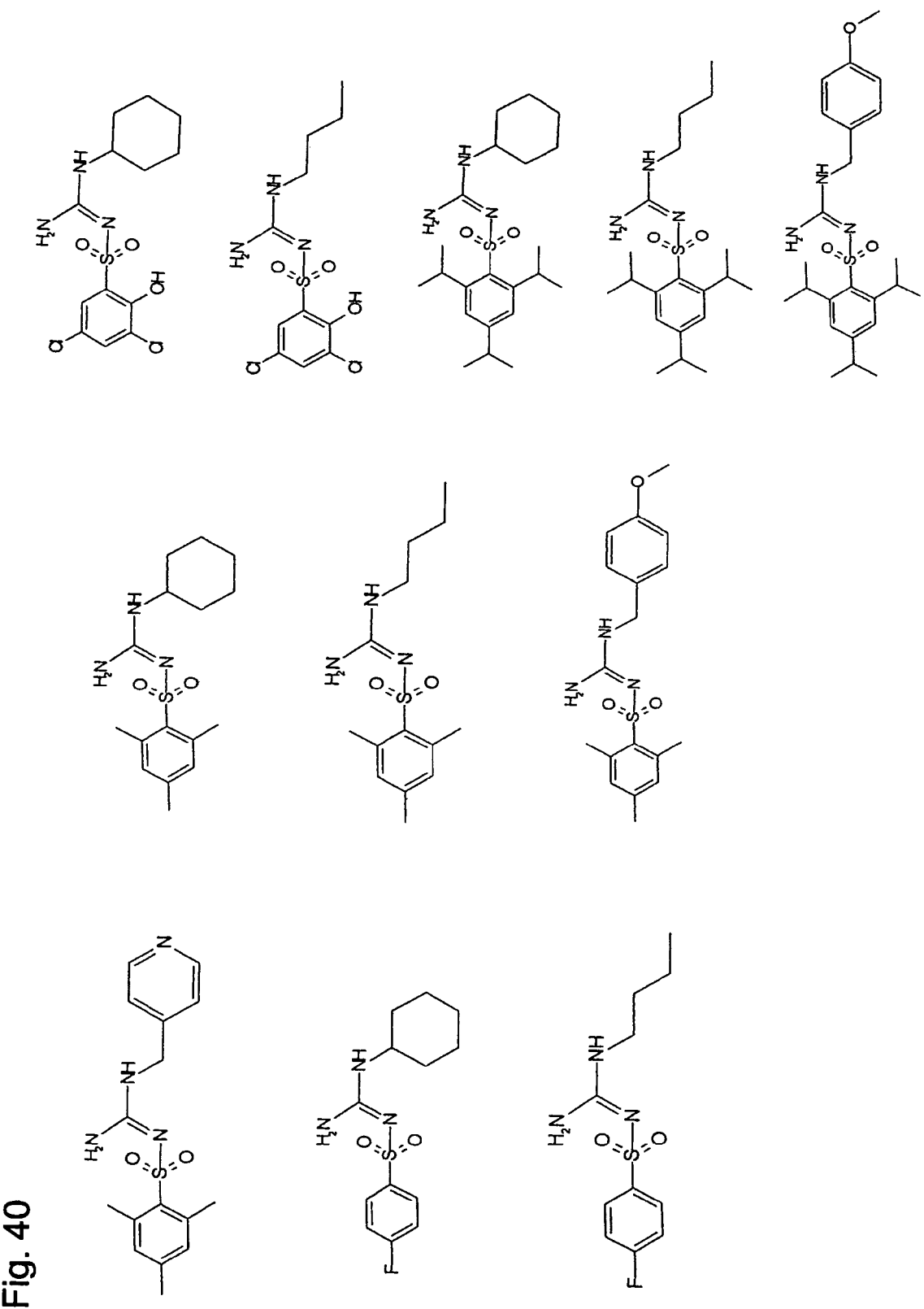

A considerable number of further compounds were synthesised according to the aforementioned processes, in particular according to the basic process 1, which are represented as structural formulas in the accompanying FIGS. 1 to 40. The compounds in these examples are compounds according to the invention and/or compounds that can be used according to the invention because of their activity profile.

Pharmacological Investigations

Example 64

Binding Assay

Gabapentin was used in a binding assay in order to check the binding and affinities of the selected compounds. The affinity of the compounds according to the invention was measured via the displacement of gabapentin from its binding site. If the selected compounds replace gabapentin from its binding site, then it may be expected that they will exhibit pharmacological properties comparable to those of gabapentin, for example as an agent to control pain or epilepsy. The compounds according to the invention exhibit a good inhibition/displacement of gabapentin in this assay. Furthermore, the investigated compounds exhibited in this biochemical assay an affinity for the hitherto unknown gabapentin binding site.

TABLE 1

| Example | Inhibition $10^{-5}$ [μM] | $IC_{50}$ [nM] |
| --- | --- | --- |
| 1 | 82% | 421 |
| 2 | 69.7% | |
| 3 | | |
| 4 | | |
| 5 | | |
| 6 | | |
| 7 | | |
| 8 | | |
| 9 | | |
| 10 | | |
| 11 | | |
| 12 | | |
| 13 | | |
| 14 | | |

TABLE 1-continued

| Example | Inhibition $10^{-5}$ [μM] | $IC_{50}$ [nM] |
| --- | --- | --- |
| 15 | | |
| 16 | | |
| 17 | | |
| 18 | | |
| 20 | | |
| 21 | 75% | 779 |
| 22 | | |
| 23 | | |
| 24 | | |
| 25 | | |
| 26 | | |
| 27 | | |
| 28 | | |
| 29 | | |
| 30 | | |
| 31 | n.a. | |
| 32 | | 218 |
| 33 | | 1100 |
| 34 | | 33 |
| 35 | | 50 |
| 36 | 17% | |
| 37 | | 122 |
| 38 | n.a. | |
| 39 | 27% | |
| 40 | 21% | |
| 41 | | 438 |
| 42 | | 27 |
| 43 | | 634 |
| 44 | | 5300 |
| 45 | 35% | |
| 46 | 36% | |
| 47 | | 2800 |
| 48 | | 136 |
| 49 | | 90 |
| 50 | | 170 |
| 51 | 5% | |
| 52 | 47% | |
| 53 | 26% | |
| 54 | | 3510 |
| 55 | | 3200 |
| 56 | 49% | |
| 57 | 41% | |
| 58 | | 1820 |
| 59 | | 970 |
| 60 | | 5690 |
| 61 | 24% | |
| 62 | 29% | |
| 63 | 23.5% | | n.a. denotes an insufficient measurement signal.

Example 65

In Vivo Experiments According to Chung

In male Sprague-Dawley rats spinal nerve ligatures were applied according to Kim and Chung (1992) to the left L5/L6 spinal nerves. At the same time spinal catheters were implanted according to Pogatzki et al.[6] (2000). 4 to 6 days after the operation the tactile threshold baseline (withdrawal thresholds) was measured on the ipsilateral and contra lateral rear paw by an electronic vonFrey anaesthesiometer (IITC Life Science, USA). The correct position of the spinal catheters was confirmed by administering lidocaine (10 μl, 2%), which resulted in a brief paralysis of the bilateral rear member. After the test and baseline measurement, gabapentin and substances according to the invention were administered. The tactile withdrawal thresholds were measured 30 minutes after administration. The results are expressed as $ED_{50}$ and % maximal possible effect (% MPE; % of the maximal possible effect) on the ipsilateral side, in which the baseline is taken as 0% and the withdrawal threshold of a control group is taken as 100% MPE.

The substance according to Example 1 showed a 50% effect at a dose of 25 mg/kg, roughly corresponding to the $ED_{50}$, and gabapentin exhibited an $ED_{50}$ of 92.6 mg/kg. Both substances acted for at least 30 hours. Accordingly, the substance according to Example 1 is superior to gabapentin in this model by a factor of 4.

Also in a further investigation, the substances according to Example 1 and according to Example 21 show an effect in the Chung test. Both substances act for at least 30 hours and are superior in their effect to gabapentin ($ED_{50}$=92.6 mg/kg).

TABLE 2

Analgesia testing in rats according to Chung:

| Example No. | Formalin Test on Mice - $ED_{50}$ |
|---|---|
| 21 | 13.3 mg/kg |
| 1 | 10-20 mg/kg |

Literature:
Kim, S. H.; Chung, J. M. (1992) An experimental model for peripheral mononeuropathy produced by segmental spinal nerve ligation in the rat. Pain 50, 355-363.

Pogatzki, E. M.; Zahn, P. K.; Brennan, T. J. (2000) Lumbar catheterization of the subarachnoid space with a 32-gauge polyurethane catheter in the rat. Eur. J. Pain 4, 111-113.

Example 66

Formalin Test on Mice

The investigations to determine the antinociceptive action of the compounds according to the invention were carried out by the formalin test on male albino mice (NMRI, 25-35 g, Iffa Credo, Belgium).

In the formalin test the first (early) phase (0-15 minutes after the formalin injection) and the second (late) phase (15-60 minutes after the formalin injection) differ (D. Dubuisson et al., Pain, Vol. 4, pp. 161-174 (1977)). The early phase, being a direct reaction to the formalin injection, constitutes a model for acute pain, whereas the late phase is regarded as a model for persistent (chronic) pain (T. J. Coderre et al., Pain, Vol. 52, pp. 259-285 (1993)).

The compounds according to the invention were investigated in the second phase of the formalin test in order to obtain information on the effects of substances in chronic/inflammatory pain. By means of a single subcutaneous formalin injection (20 µl, 1% aqueous solution) into the dorsal side of the right-hand rear paw, a nociceptive reaction was induced in unconstrained experimental animals, manifested in a noticeable licking and biting of the affected paw.

The nociceptive behavior for the test period in the second (late) phase of the formalin test was continuously monitored by observing the animals. The pain reaction was quantified by totaling the time in seconds during which the animals continued to lick and bite the affected paw during the investigation period. After injecting substances that have an antinociceptive effect in the formalin test, the aforedescribed behavior pattern of the animals is reduced or possibly even cancelled.

Corresponding to the substance tests, in which the animals had been injected with the test substance before formalin, the control animals were injected with a vehicle, i.e. solvent (e.g. 0.9% NaCl solution) before the formalin injection. The behavior of the animals after administration of the substance (n=10 per substance dose) was compared with a control group (n=10).

Based on the quantification of the pain reaction, the effect of the substance in the formalin test was determined as the change in the control in percentage terms. The $ED_{50}$ calculations were carried out by means of regression analysis. The application time before the formalin injection (intraperitoneally: 15 minutes, intravenously: 5 minutes) was chosen depending on the type of application of the compounds according to the invention.

The compound of Example 21 according to the invention exhibited an inhibition of the formalin-induced nociception. The corresponding results in the formalin test on mice are shown in the following Table 2. Gabapentin has an $ED_{50}$ value of 79 mg/kg (i.v.).

TABLE 2

Analgesia investigation in the formalin test on mice

| Example No. | Formalin Test on Mice - $ED_{50}$ |
|---|---|
| 21 | 97 mg/kg |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A sulfonylguanidine compound selected from the group consisting of:
N-{amino-[pyridin-2-yl-methyl)-amino]-methylene}-4-methylbenzenesulfonamide (1)
N-[amino-(benzylaminomethylene)]-4-methylbenzene-sulfonamide (2)
N-[(amino-4-methoxybenzylamino)-methylene]-4-methylbenzene-sulfonamide (6)
N-[aminophenethylaminomethylene]-4-methylbeuzene-sulfonamide (14)
N-{amino-[(pyridin-2-yl-methyl)-amino]-methylene}-4-chlorobenzenesulfonamide (21)
N-{amino-[(pyridin-4-yl-methyl)-amino]-methylene}-4-methylbenzenesulfonamide (22)
N-{amino-[(pyridin-3-yl-methyl)-amino]-methylene}-4-ethylbenzenesulfonamide (23)
N-{amino[(pyridin-2-yl-methyl)-amino]-methylene}-4-bromobenzenesulfonamide (32)
N-{amino[(pyridin-2-yl-methyl)-amino]-methylene}-3,4-dichlorobenzenesulfonamide (33)
N-{amino[(pyridin-2-yl-methyl)-amino]-methylene}-4-isopropylbenzenesulfonamide (34)
N-{amino[(pyridin-2-yl-methyl)-amino]-methylene}-4-iodobenzenesulfonamide (35)
N-{amino[(pyridin-2-yl-methyl)-amino]-methylene}-benzenesulfonamide (36)
Naphthalene-2-sulfonic acid amino-[(pyridin-2-yl-methyl)-amino]-methylene amide (37)
1-methyl-1H-imidazole-4-sulfonic acid amino-[(pyridin-2-yl-methyl)-amino]-methylene amide (38)
N-[4-({amino-[(pyridin-2-yl-methyl)-amino]-methylene}-sulfamoyl)-phenyl]-acetamide (39)

N-{amino[(pyridin-2-yl-methyl)-amino]-methylene}-4-fluorobenzenesulfonamide (40)
N-{amino[(pyridin-2-yl-methyl)-amino]-methylene}-2,4,6-trimethylbenzenesulfonamide (41)
N-{amino[(pyridin-2-yl-methyl)-amino]-methylene}-4-propylbenzenesulfonamide (42)
N-{amino[(pyridin-2-yl-methyl)-amino]-methylene}-4-methoxybenzenesulfonamide (43)
Naphthalene-1-sulfonic acid amino-[(pyridin-2-yl-methyl)-amino]-methylene amide (44)
N-{amino[(pyridin-2-yl-methyl)-amino]-methylene}-3-methylbenzenesulfonamide (45)
Thiophene-2-sulfonic acid amino-[(pyridin-2-yl-methyl)-amino]-methylene amide (46)
Quinoline -8-sulfonic acid amino-[(pyridin-2-yl-methyl)-amino]-methylene amide (47)
5-chloro-3-methylbenzo[b]thiophene-2-sulfonic acid amino-[(pyridin-2-yl-methyl)-amino]-methylene amide (48)
N-{amino[(pyridin-2-yl-methyl)-amino]-methylene}-4-tert.-butylbenzenesulfonamide (49)
N-{amino[(pyridin-2-yl-methyl)-amino]-methylene}-4-butylbenzenesulfonamide (50)
N-{amino[(pyrimidin-2-yl-methyl)-amino]-methylene}-4-tert.-butylbenzenesulfonamide (51)
N-{amino[(furan-2-yl-methyl)-amino]-methylene}-4-butylbenzenesulfonamide (52)
N-{amino[(furan-2-yl-methyl)-amino]-methylene}-4-methylbenzenesulfonamide (53)
N-{amino[(furan-2-yl-methyl)-amino]-methylene}-4-isopropylbenzenesulfonamide (54)
N-{amino[(furan-2-yl-methyl)-amino]-methylene}-4-propylbenzenesulfonamide (55)
N-{amino[(furan-2-yl-methyl)-amino]-methylene}-4-tert.-butylbenzenesulfonamide (56)
N-{amino[(thiophen-2-yl-methyl)-amino]-methylene}-4-butylbenzenesulfonamide (57)
N-{amino[(thiophen-2-yl-methyl)-amino]-methylene}-4-propylbenzenesulfonamide (58)
N-{amino[(thiophen-2-yl-methyl)-amino]-methylene}-4-isopropylbenzenesulfonamide (59)
N-{amino[(thiophen-2-yl-methyl)-amino]-methylene}-4-tert.-butylbenzenesulfonamide (60)
N-{amino[(thiophen-2-yl-methyl)-amino]-methylene}-4-chlorobenzenesulfonamide (61)
N-{amino[(thiophen-2-yl-methyl)-amino]-methylene}-4-methylbenzenesulfonamide (62), and
N-{amino[(furan-2-yl-methyl)-amino]-methylene}-4-chlorobenzenesulfonamide (63), optionally in the form of a racemate, a pure enantiomer or diastereomer, or in the form of mixtures of the stereoisomers in an equimolar or nonequimolar mixing ratio; in the represented form or in the form of an acid or a base; or in the form of a physiologically compatible salt.

2. A compound according to claim 1, wherein said compound is present in the form of a salt.

3. A compound according to claim 1, wherein said compound is present in the form of a hydrochloride or sodium salt.

4. A compound according to claim 1, wherein said compound is present in the form of a base.

5. A compound according to claim 1, wherein said compound is present in the form of an acid.

6. A pharmaceutical composition comprising a pharmaceutically active sulfonylguanidine compound according to claim 1, and at least one pharmaceutical carrier, additive or auxiliary substance.

7. A pharmaceutical composition according to claim 6, further comprising a further pharmaceutically active compound.

8. A pharmaceutical composition according to claim 6, wherein the sulfonylguanidine compound is present as a pure diastereomer or a pure enantiomer.

9. A pharmaceutical composition according to claim 6, wherein the sulfonylguanidine compound is present as a non-equimolar mixture of diastereomers or enantiomers.

10. A pharmaceutical composition according to claim 6, wherein the sulfonylguanidine compound is present as a racemate or an equimolar mixture of diastereomers or enantiomers.

11. A method of treating a condition selected from the group consisting of pain and migraine; said method comprising administering to a patient in need thereof a pharmaceutically effective amount of a sulfonylguanidine compound according to claim 1.

12. A method according to claim 11, wherein said condition is selected from the group consisting of neuropathic pain, chronic pain and acute pain.

13. A method according to claim 11, wherein the sulfonylguanidine compound is present as a pure diastereomer or a pure enantiomer.

14. A method according to claim 11, wherein the sulfonylguanidine compound is present as a non-equimolar mixture of the diastereomers or enantiomers.

15. A method according to claim 11, wherein the sulfonylguanidine compound is present as a racemate or an equimolar mixture of diastereomers or enantiomers.

16. A method according to claim 11, wherein the sulfonylguanidine compound is present as an acid.

17. A method according to claim 11, wherein the sulfonylguanidine compound is present as a salt.

18. A method according to claim 11, wherein the sulfonylguanidine compound is present as a base.

* * * * *